(12) United States Patent
Yoo et al.

(10) Patent No.: US 11,412,709 B2
(45) Date of Patent: Aug. 16, 2022

(54) TREADMILL HAVING DEODORIZER

(71) Applicant: LG ELECTRONICS INC., Seoul (KR)

(72) Inventors: Hyunsun Yoo, Seoul (KR); Joo-Gyeom Kim, Seoul (KR); Jaehung Chun, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 511 days.

(21) Appl. No.: 16/690,448

(22) Filed: Nov. 21, 2019

(65) Prior Publication Data
US 2021/0153465 A1  May 27, 2021

(51) Int. Cl.
*A01K 15/02*  (2006.01)
*A63B 22/02*  (2006.01)
(Continued)

(52) U.S. Cl.
CPC .............. *A01K 15/027* (2013.01); *A61L 2/10* (2013.01); *A61L 2/26* (2013.01); *A61L 9/205* (2013.01);
(Continued)

(58) Field of Classification Search
CPC .... A01K 15/027; A01K 5/02; A63B 21/4035; A63B 22/025; A63B 22/0292;
(Continued)

(56) References Cited

U.S. PATENT DOCUMENTS

| 4,066,257 A | 1/1978 | Moller |
| 4,095,561 A | 6/1978 | Ruetenik |

(Continued)

FOREIGN PATENT DOCUMENTS

| CN | 104436539 | 3/2015 |
| CN | 106422175 | 2/2017 |

(Continued)

OTHER PUBLICATIONS

European Search Report dated Nov. 13, 2020 issued in EP Application No. 20151919.6.

(Continued)

*Primary Examiner* — Bao Q Truong
(74) *Attorney, Agent, or Firm* — Ked & Associates, LLP

(57) ABSTRACT

A treadmill may include two separate left and right belts rotating around two sets of rollers, four legs having an adjustable height via air suspension to customize an inclination of the treadmill, a thermoelectric assembly, a fragrance assembly having a rotating fragrance cartridge to emit various smells toward a user of the treadmill, a display on which exercise programs are played, and an attachment module having a dispensing tray on which treats are dispensed. A handle of the treadmill may have a sensor to sense a height and front-rear position, and a belt divider provided between the left and right belts may have position or proximity sensors to sense a left-right position. An inclination of the treadmill may be automatically adjusted according to positions detected by the sensors, and the fragrance assembly, attachment module, and inclination may be automatically operated in accordance with an exercise program played on the display.

20 Claims, 44 Drawing Sheets

(51) Int. Cl.
*A61M 21/02* (2006.01)
*A63B 24/00* (2006.01)
*A63B 71/00* (2006.01)
*A61L 9/22* (2006.01)
*A61L 9/20* (2006.01)
*A61L 2/10* (2006.01)
*A61L 2/26* (2006.01)
*A63B 21/00* (2006.01)
*A61M 21/00* (2006.01)
*A01K 5/02* (2006.01)

(52) U.S. Cl.
CPC .............. *A61L 9/22* (2013.01); *A61M 21/02* (2013.01); *A63B 21/4035* (2015.10); *A63B 22/025* (2015.10); *A63B 22/0292* (2015.10); *A63B 24/0087* (2013.01); *A63B 71/0036* (2013.01); *A01K 5/02* (2013.01); *A61L 2202/11* (2013.01); *A61M 2021/005* (2013.01); *A61M 2021/0016* (2013.01); *A61M 2021/0027* (2013.01); *A61M 2205/056* (2013.01); *A61M 2205/07* (2013.01); *A61M 2205/3673* (2013.01); *A61M 2209/10* (2013.01); *A61M 2250/00* (2013.01); *A63B 2208/14* (2013.01); *A63B 2210/50* (2013.01); *A63B 2220/833* (2013.01); *A63B 2225/093* (2013.01); *A63B 2225/096* (2013.01)

(58) Field of Classification Search
CPC ............ A63B 24/0087; A63B 71/0036; A63B 2208/14; A63B 2210/50; A63B 2220/833; A63B 2225/093; A63B 2225/096; A61L 2/10; A61L 2/26; A61L 9/205; A61L 9/22; A61L 2202/11; A61M 21/02; A61M 2021/0016; A61M 2021/0027; A61M 2021/005; A61M 2205/056; A61M 2205/07; A61M 2205/3673; A61M 2209/10; A61M 2250/00
See application file for complete search history.

(56) References Cited

U.S. PATENT DOCUMENTS

| | | |
|---|---|---|
| 4,205,628 A | 6/1980 | Null |
| 4,332,217 A | 6/1982 | Davis |
| 4,361,115 A | 11/1982 | Pike |
| 4,981,136 A | 1/1991 | Chance |
| 5,002,015 A | 3/1991 | Sampson et al. |
| 5,081,991 A | 1/1992 | Chance |
| 5,100,127 A | 3/1992 | Melnick et al. |
| 5,277,150 A | 1/1994 | Rhodes |
| 5,279,528 A | 1/1994 | Dalebout et al. |
| 5,372,560 A | 12/1994 | Chang |
| 5,672,140 A | 9/1997 | Watterson et al. |
| 5,676,624 A | 10/1997 | Watterson et al. |
| 5,772,560 A | 6/1998 | Watterson et al. |
| 5,775,263 A | 7/1998 | Richards |
| 6,058,888 A | 5/2000 | Nichols |
| 6,241,638 B1 | 6/2001 | Hurt |
| 6,347,603 B1 | 2/2002 | Felger |
| 6,609,478 B2 | 8/2003 | Del Valle |
| 6,676,569 B1 | 1/2004 | Radow |
| 6,722,316 B1 | 4/2004 | Joycey et al. |
| 6,837,186 B1* | 1/2005 | Terao ................. A01K 15/027 119/701 |
| D527,060 S | 8/2006 | Flick et al. |
| 7,097,593 B2 | 8/2006 | Chang |
| 7,654,229 B2 | 2/2010 | Smith |
| 7,736,273 B2 | 6/2010 | Cox et al. |
| 7,780,573 B1 | 8/2010 | Carmein |
| D624,975 S | 10/2010 | Flick et al. |
| D704,778 S | 5/2014 | Decommer |
| 9,622,686 B1 | 4/2017 | Berme et al. |
| 9,623,286 B1 | 4/2017 | Chen |
| 9,737,046 B1 | 8/2017 | Pugh |
| 10,335,632 B2 | 7/2019 | Baker |
| 10,376,734 B1 | 8/2019 | Razon |
| 11,310,997 B2* | 4/2022 | Yoo ................. A63B 24/0087 |
| 2002/0002103 A1 | 1/2002 | Watterson et al. |
| 2002/0157617 A1 | 10/2002 | Reinkensmeyer et al. |
| 2004/0002406 A1 | 1/2004 | Lopez-Santillana et al. |
| 2004/0097341 A1 | 5/2004 | Alessandri et al. |
| 2005/0148443 A1 | 7/2005 | Watterson et al. |
| 2005/0209059 A1 | 9/2005 | Crawford et al. |
| 2005/0209060 A1 | 9/2005 | Lull |
| 2005/0227820 A1 | 10/2005 | Dyer et al. |
| 2005/0233864 A1 | 10/2005 | Smith et al. |
| 2007/0022970 A1* | 2/2007 | Newman ............... A01K 15/027 119/700 |
| 2007/0123390 A1 | 5/2007 | Mathis |
| 2008/0287266 A1 | 11/2008 | Smith |
| 2009/0124938 A1 | 5/2009 | Brunner |
| 2010/0010668 A1 | 1/2010 | Udono |
| 2010/0175634 A1* | 7/2010 | Chang ................. A01K 15/027 119/700 |
| 2010/0210419 A1 | 8/2010 | Park |
| 2010/0248900 A1 | 9/2010 | Ashby et al. |
| 2010/0261579 A1 | 10/2010 | Rice |
| 2011/0065373 A1 | 3/2011 | Goldmann et al. |
| 2012/0024237 A1 | 2/2012 | Rice |
| 2012/0204806 A1* | 8/2012 | Sant'Anna ........... A01K 13/001 119/656 |
| 2013/0035208 A1 | 2/2013 | Dalebout et al. |
| 2013/0092096 A1* | 4/2013 | Rosenberg ........... A01K 15/027 119/703 |
| 2013/0237383 A1 | 9/2013 | Chen et al. |
| 2013/0274069 A1 | 10/2013 | Watterson et al. |
| 2013/0281241 A1 | 10/2013 | Watterson et al. |
| 2014/0243156 A1 | 8/2014 | Cohen |
| 2015/0306440 A1 | 10/2015 | Bucher et al. |
| 2016/0023081 A1 | 1/2016 | Popa-Simil et al. |
| 2016/0059068 A1 | 3/2016 | Olson |
| 2016/0213976 A1 | 7/2016 | So et al. |
| 2016/0296800 A1 | 10/2016 | Devor et al. |
| 2017/0056716 A1 | 3/2017 | Cutler |
| 2017/0136289 A1 | 5/2017 | Frank |
| 2017/0209734 A1 | 7/2017 | Huang |
| 2018/0056111 A1 | 3/2018 | Chiang et al. |
| 2018/0296157 A1 | 10/2018 | Bleich et al. |
| 2018/0311528 A1 | 11/2018 | Swarts |
| 2018/0345070 A1 | 12/2018 | Yakovenko et al. |
| 2019/0174719 A1 | 6/2019 | Perata |
| 2019/0240535 A1 | 8/2019 | Santra et al. |
| 2019/0289285 A1 | 9/2019 | Nashida et al. |
| 2021/0001678 A1 | 1/2021 | Koyama et al. |
| 2021/0046373 A1 | 2/2021 | Smith |
| 2021/0153463 A1 | 5/2021 | Yoo et al. |
| 2021/0153464 A1 | 5/2021 | Yoo et al. |
| 2021/0153466 A1 | 5/2021 | Yoo et al. |
| 2021/0154526 A1 | 5/2021 | Yoo et al. |

FOREIGN PATENT DOCUMENTS

| | | |
|---|---|---|
| CN | 109091807 | 12/2018 |
| DE | 202019105992 | 12/2019 |
| EP | 1 413 334 | 4/2004 |
| EP | 2 075 099 | 7/2009 |
| JP | 2006-129825 | 5/2006 |
| KR | 20-0315523 | 6/2003 |
| KR | 10-2003-0068099 | 8/2003 |
| KR | 20-0322201 | 8/2003 |
| KR | 20-0331594 | 11/2003 |
| KR | 20-0336953 | 12/2003 |
| KR | 20-0340328 | 2/2004 |
| KR | 20-0375742 | 3/2005 |
| KR | 10-2007-0043325 | 4/2007 |
| KR | 10-2008-0026235 | 3/2008 |
| KR | 10-2009-0129077 | 12/2009 |
| KR | 10-2010-0108926 | 10/2010 |
| KR | 10-2010-0113945 | 10/2010 |

(56) References Cited

FOREIGN PATENT DOCUMENTS

| KR | 10-2011-0107420 | 10/2011 |
|---|---|---|
| KR | 10-2012-0097119 | 9/2012 |
| KR | 10-2012-0129651 | 11/2012 |
| KR | 10-1433044 | 8/2014 |
| KR | 10-1461202 | 11/2014 |
| KR | 10-2016-0065677 | 6/2016 |
| KR | 10-2017-0141923 | 12/2017 |
| KR | 10-1850021 | 4/2018 |
| KR | 10-2018-0045575 | 5/2018 |
| KR | 10-2018-0058238 | 6/2018 |
| WO | WO 03/084614 | 10/2003 |
| WO | WO 2004/078272 | 9/2004 |
| WO | WO 2005/082105 | 9/2005 |
| WO | WO 2009/034307 | 3/2009 |
| WO | WO 2016/033370 | 3/2016 |
| WO | WO 2018/097440 | 5/2018 |

OTHER PUBLICATIONS

Korean Office Action dated Oct. 21, 2021 issued in KR Application No. 10-2020-0030409.
Korean Office Action dated Oct. 25, 2021 issued in KR Application No. 10-2020-0030410.
United States Notice of Allowance dated Jan. 5, 2022 issued in co-pending related U.S. Appl. No. 16/690,573.
European Search Report dated Aug. 28, 2020 issued in EP Application No. 20151919.6.
European Search Report dated Aug. 28, 2020 issued in EP Application No. 20151915.4.
European Search Report dated Aug. 28, 2020 issued in EP Application No. 20151899.0.
European Search Report dated Aug. 28, 2020 issued in EP Application No. 20151920.4.
European Search Report dated Aug. 28, 2020 issued in EP Application No. 20151926.1.
European Search Report dated Aug. 28, 2020 issued in EP Application No. 20151895.8.
European Search Report dated Aug. 31, 2020 issued in EP Application No. 20151908.9.
European Search Report dated Aug. 31, 2020 issued in EP Application No. 20151900.6.
European Search Report dated Sep. 2, 2020 issued in EP Application No. 20151909.7.
European Search Report dated Sep. 2, 2020 issued in EP Application No. 20151901.4.
European Search Report dated Sep. 2, 2020 issued in EP Application No. 20151897.4.
European Search Report dated Sep. 2, 2020 issued in EP Application No. 20151902.2.
European Search Report dated Sep. 7, 2020 issued in EP Application No. 20151918.8.
European Search Report dated Sep. 7, 2020 issued in EP Application No. 20151935.2.
U.S. Appl. No. 16/690,201, filed Nov. 21, 2019.
U.S. Appl. No. 16/690,239, filed Nov. 21, 2019.
U.S. Appl. No. 16/690,271, filed Nov. 21, 2019.
U.S. Appl. No. 16/690,312, filed Nov. 21, 2019.
U.S. Appl. No. 16/690,371, filed Nov. 21, 2019.
U.S. Appl. No. 16/690,448, filed Nov. 21, 2019.
U.S. Appl. No. 16/690,500, filed Nov. 21, 2019.
U.S. Appl. No. 16/690,573, filed Nov. 21, 2019.
U.S. Appl. No. 16/691,707, filed Nov. 22, 2019.
U.S. Appl. No. 16/691,718, filed Nov. 22, 2019.
U.S. Appl. No. 16/691,736, filed Nov. 22, 2019.
U.S. Appl. No. 16/691,743, filed Nov. 22, 2019.
U.S. Appl. No. 16/691,759, filed Nov. 22, 2019.
U.S. Appl. No. 16/691,779, filed Nov. 22, 2019.
U.S. Appl. No. 16/691,796, filed Nov. 22, 2019.
United States Office Action dated May 27, 2022 issued in co-pending related U.S. Appl. No. 16/691,718.
United States Office Action dated Jun. 1, 2022 issued in co-pending related U.S. Appl. No. 16/690,271.
United States Office Action dated Jun. 7, 2022 issued in co-pending related U.S. Appl. No. 16/690,312.
Korean Office Action dated Apr. 22, 2022 issued in KR Application No. 10-2020-0030410.

\* cited by examiner

TREADMILL HAVING DEODORIZER

BACKGROUND

1. Field

A treadmill for animals is disclosed herein.

2. Background

In recent years, the population of those raising a pet has increased in view of attachment and interest pets. Like most animals, exercise is important for a pet's physical and mental health. Ideally, pets should exercise four times or more daily. However, owners are often busy and unable to exercise their pets frequently. In addition, inclement weather may interfere with outdoor exercise even when an owner is home. Since pets are often left alone and since communication with their human owners is difficult, the demand for pet equipment which may allow a pet to use without an owner's help has increased.

U.S. Pat. Nos. 6,347,603, 4,332,217, 4,205,628, 4,095,561, 5,081,991, 4,361,115, 7,736,273, 6,609,478, 6,837,186, 6,722,316, 6,058,888, 5,775,263, 5,277,150, 5,002,015, and 4,981,136, and U.S. Publication Nos. 2013/0092096, 2012/0024237, and 2010/0175634 disclose treadmills for animals (hereinafter "related art.") However, such pet treadmills have various disadvantages, which the present disclosure solves. For example, the treadmills of the related art do not have many devices to stimulate a pet while a pet exercises autonomously on the treadmill. In addition, the treadmills of the related art are not easily customizable, adjustable, or portable.

The above references are incorporated by reference herein where appropriate for appropriate teachings of additional or alternative details, features and/or technical background.

DETAILED DESCRIPTION OF THE INVENTION

Figure 1:
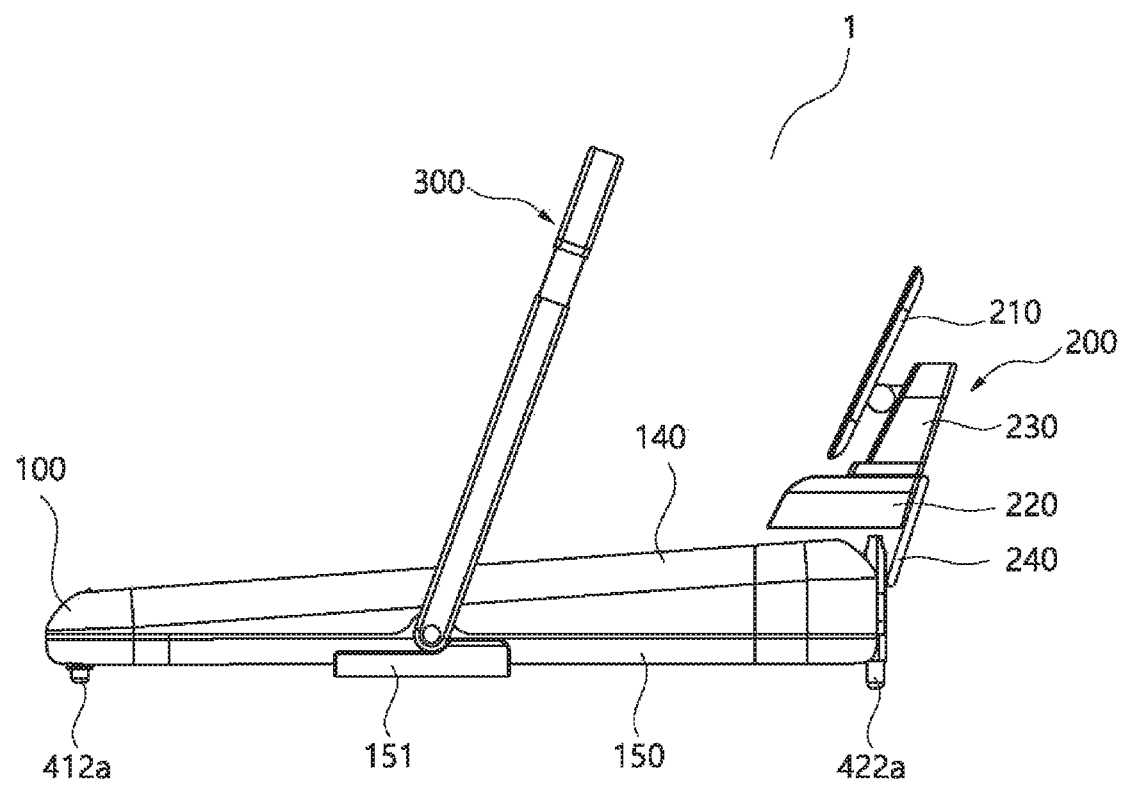
FIG. 1 is a side view of a treadmill according to an embodiment.

Referring to FIGS. 1-5, a treadmill 1 according to an embodiment may include a base 100 including rotating left and right belts 110 and 120 on which an animal or a pet (e.g., dog) may exercise (e.g., run, walk, or skip). The left and right belts 110 and 120 may rotate at different speeds to accommodate different stride lengths on left and right sides of a pet. The speeds of the left and right belts 110 and 120 may be configured to correspond to a linear speed of a typical pet walking alongside a human. As described in this specification, "left" and "right" may mean with respect from a view from a rear of the treadmill 1 (i.e., from a perspective while using the treadmill 1).

An attachment module 200 provided at a front of the treadmill 1 may play videos on a removable display 210 and dispense treats from a removable container 230 onto a removable dispensing tray 220. Treats may be dispensed onto the dispensing tray 220 from the container 230 to lure a pet to the treadmill 1, stimulate a pet during exercise, and reward a pet after exercise. The display 210 may play videos or sounds to both lure a pet to the treadmill 1 and stimulate a pet on the treadmill 1 in accordance with a pre-set exercise program.

The attachment module 200 may be easily removable or customizable, and the treadmill 1 may further include a handle 300 that folds down to surround the base 100 for easy storage and portability when the attachment module 200 is removed. When the handle 300 is not folded and is erected above the left and right belts 110 and 120, a user may lift the treadmill 1 by the handle 300 to reposition or move the treadmill 1. The handle 300 may include a handle sensor 331 (e.g., image sensor or camera) that detects a height of the pet, and a height of the handle 300 may be automatically adjusted based on the sensed height of the pet by the handle sensor 331. The handle sensor 331 may also sense a position of the pet in a frontward and backward direction, and speeds of the left and right belts 110 and 120 may be adjusted to maintain a safe position of the pet on the treadmill 1. The speeds of the left and right belts 110 and 120 may also be controlled according to a pre-set exercise program and may correspond to images on the display 210. When the left and right belts 110 and 120 are moving at slightly different speeds, the speeds of the left and right belts 110 and 120 may be increased or decreased by a same amount in response to a position of the pet sensed by the handle sensor 331.

Figure 6:
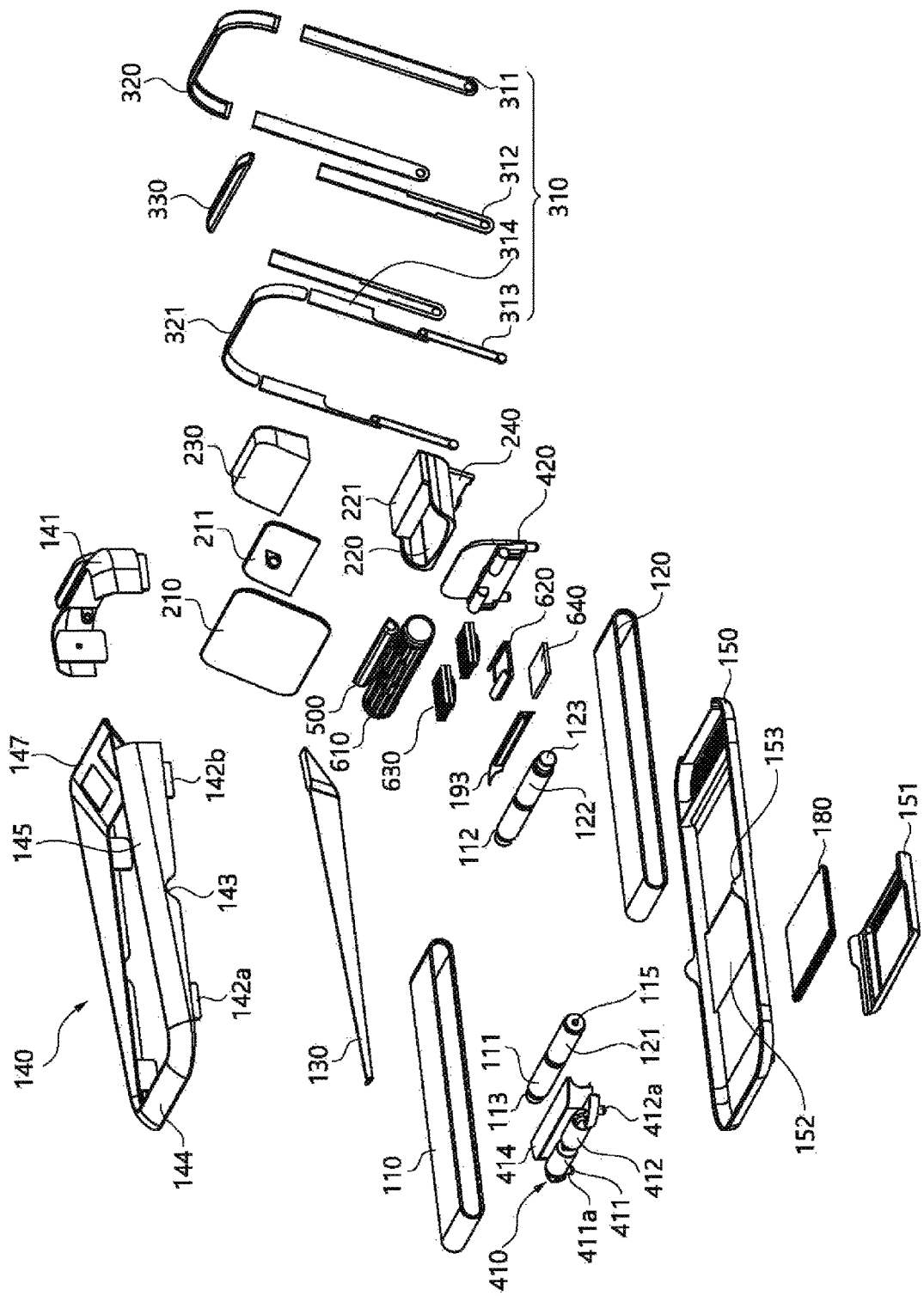
FIG. 6 is an exploded perspective view of a treadmill according to an embodiment.

A divider 130 may be provided between the left and right belts 110 and 120 and may be removed during storage. The divider 130 may include left and right proximity sensors 132 and 133 to sense a position of the pet in a left-right direction. The treadmill 1 may include adjustable legs 411a, 412a, 421a, and 422a that are each independently controlled by a height adjustment assembly having back and front height adjusters 410 and 420 (FIG. 6). Based on a position detected by the left and right proximity sensors 132 and 133, heights of the legs 411a, 412a, 421a, and 422a may be raised or lowered to adjust an inclination of the treadmill 1 at four separate corners. An inclination of the treadmill 1 may also be adjusted as part of a pre-set exercise program and correspond to images on the display 210.

The base 100 may include an upper frame or cover 140 coupled to a lower frame or cover 150. Sides of the base 100 may have a relatively low height as compared to a pet on the treadmill 1 so as to reduce anxiety. An upper surface of the upper frame 140 may have a height that is similar to or only a few inches above a height of upper surface of the first and second belts 110 and 120. The height of the upper frame 140 may increase from the rear of the base 100 to the front of the base 100. The left and right belts 110 and 120 may be exposed through the upper frame 140. The upper frame 140 may include openings 147 in which vents or vanes 146 may be provided. Cool or hot air may flow through the vents 146 to the pet on the left and right belts 110 and 120, and the vents 146 may be automatically opened and closed to control a flow of air through the vents 146. Scented air and/or deodorizing ions may also be blown through the vents 146 to the air around the pet.

Discharge holes 154 may be provided in the lower frame 150 of the base 100 to exhaust air from a blower 610 (FIG. 8) inside the treadmill 1. For example, during a cooling operation, hot air may be discharged through the discharge holes 154, while cool air may be blown by the blower 610 through the vents 146. During a heating operation, cool air may be discharged through the discharge holes 154, while hot or warm air may be blown by the blower 610 through the vents 146. A position of the blower 610 may be configured to blow air straight through the vents 146 or to blow air through the vents 146 at a predetermined angle.

Referring to FIGS. 6-10B, the blower 610 may be a radially bladed fan 610, e.g., tangential or cross-flow fan, to blow warm, cold, and/or scented air through the vents 146 to the pet. The radially bladed fan 610 may also disperse ions emitted or generated by a deodorizer 620 through the vents 146 to break apart pollutants and deodorize the air surrounding the treadmill 1. The left and right belts 110 and 120 may be further cleaned by first and second sterilizing lights 191 and 192 provided at the back and front ends of the treadmill 1 (FIGS. 21-22), respectively, that each emit ultraviolet (UV) radiation.

The treadmill 1 may include a fragrance assembly 500 that emits various scents, and the radially bladed fan 610 may disperse scent through the vents 146 to the pet. Scents may be emitted to both lure a pet to the treadmill 1 and stimulate a pet on the treadmill 1 in accordance with a pre-set exercise program and/or images played on the display 210.

The pet may be both lured to and stimulated on the treadmill 1 via a combination of treats dispensed on the dispensing tray 220, images and sounds played on the display 210, and scents emitted by the fragrance assembly 500 through the vents 146. As an example, a treat may be dispensed onto the dispensing tray 220 and pre-recorded sounds may be emitted by the display 210 to lure the pet onto the treadmill 1. Once it is determined that the pet is on the treadmill 1, the left and right belts 110 and 120 may rotate. An exercise program, e.g., a forest trail, may play on the display 210, and the fragrance assembly 500 may emit a forest or phytoncide scent. Speeds and inclinations of the left and right belts 110 and 120 may be adjusted in accordance with the exercise program played on the display 210 and also adjusted based on a position of the pet on the treadmill. Periodically, a treat may be dispensed onto the dispensing tray 220 to reward the pet for its exercise.

A debris remover 180 may be provided under the base 100 to catch pet fur or other debris on the left and right belts 110 and 120. The debris remover 180 may be covered by a removable bottom cover 151. The bottom cover 151 may be removed so that a user may periodically remove the debris remover 180 to discard caught debris. The treadmill 1 may therefore be kept clean by the debris remover 180 on bottom, the deodorizer 620 behind the vents 146, and the first and second sterilizing lights 191 and 192 (FIGS. 21 and 22) facing the left and right belts 110 and 120 at the back and front ends of the treadmill 1.

Referring to FIGS. 6-10 in more detail, the lower frame 150 of the base 100 may be provided under the left and right belts 110 and 120. An upper frame 140 may be coupled to the lower frame 150, and may have an upper opening through which the left and right belts 110 and 120 are exposed. The upper frame 140 may have a front frame or cover 141 provided at the front end of the base 100 to cover the fragrance assembly 500 and the blower 610 described later with reference to FIGS. 23-27. The upper frame 140 may further include a back frame or cover 144 provided at the back end of the base 100, and a pair of side walls or side frames 145 extending between the front and back frames 141 and 144. The left and right belts 110 and 120 may be exposed between the side frames 145 and the front and back frames 141 and 144.

The upper and lower frames 140 and 150 may be made of a plastic so that the treadmill 1 is lightweight, portable, and easy to manufacture. The side frames 145 may be bonded or welded to the front and back frames 144 and 141 to form the upper frame 140. The upper frame 140 may be pressed-fit or snap-fitted into the lower frame 150. Alternatively, the upper frame 140 may be secured to the lower frame 150 via magnetic coupling, adhesion, locking or latching, etc. The base 100 and left and right belts 110 and 120 may be configured to support a small to medium sized dog (e.g., 10 kg or 20 lbs or less), but embodiments disclosed herein are not limited thereto.

The left belt 110 may be a closed loop that rotates around left back and front rollers 111 and 112, and the right belt 120 may be a closed loop that rotates around right back and front rollers 121 and 122. The rollers 111, 112, 121, and 122 may be configured to grip a bottom surface of the belt belts 110 and 120 by a friction force or in a gear teeth configuration. The belts 110 and 120 may serve as the primary surfaces on which a pet exercises.

The back rollers 111 and 121 may be provided at a back end of the treadmill 1, and the front rollers 112 and 122 may be provided at a front end of the treadmill 1. Each of the rollers 111, 112, 121, and 122 may have a cylindrical or pipe shape having a longitudinal direction perpendicular to longitudinal directions of the treadmill 1 and the belts 110 and 120.

The front rollers 112 and 122 may rotate around and be supported by a front shaft 125 supporting the front rollers 112 and 122, and the back rollers 111 and 121 may rotate around and be supported by a back shaft 115. The front shaft 125 may extend between and couple to a front pair of roller frames 142b, and the back shaft 115 may extend between and couple to a back pair of roller frames 142a. The front and back roller frames 142b and 142a may extend downward from the side frames 145.

The front and back shafts 125 and 115 may remain fixed, while the left rollers 111 and 112 may rotate at a different speed than the right rollers 121 and 122. The front left and right rollers 112 and 122 may not be coupled to each other to facilitate independent rotation and separate left and right speeds, and the back left and right rollers 111 and 121 may similarly not be coupled to each other to facilitate independent rotation and separate left and right speeds.

A right motor 123 may rotate the front right belt 122 around the front shaft 125 and a left motor 113 may rotate the back left belt 111 around the back shaft 115. The front and back shafts 125 and 115 may remain fixed and may not rotate, and the motors 123 and 113 may only rotate the rollers 122 and 111 surrounding the fixed front and back shafts 125 and 115, respectively.

Many animals, including humans and pets, have unequal leg lengths resulting in unequal stride lengths or gait on left and right legs. Humans and animals may naturally veer to the left or right due to gait. To efficiently and safely exercise a pet with unequal stride lengths, the left and right belts 110 and 120 may run at different speeds to accommodate the unequal pacing of the pet at left and right sides. The left belt 110 may rotate at a first speed around back and front rollers 111 and 112 provided at back and front ends of the base 100, respectively, and the right belt 120 may rotate at a second speed around back and front rollers 121 and 122 provided at back and front ends of the base 100, respectively. Textures of the left and right belts 110 and 120 may also be configured to accommodate a known gait of the pet, as a faster belt may have more traction. For example, if a speed of the left belt 110 is typically adjusted to be faster than a speed of the right belt 120 to accommodate gait of the pet, the owner may choose to replace the left belt 110 with a replacement left belt 110 having greater traction or friction to prevent slipping.

The divider 130 may be provided between the left and right belts 110 and 120 to cover or hide any space or gap between the left and right belts 110 and 120 and to prevent a pet from accidentally placing a paw or leg in any gap between the left and right belts 110 and 120. The divider 130 may also keep a pet's left leg on the left belt 110 and a right leg on the right belt 120. The divider 130 may prevent the pet from moving too far to the left or right on the treadmill 1 or prevent the pet from tripping at higher speeds.

The divider 130 may be easily detachable from the treadmill 1 via, e.g., a magnet connection. A bottom surface of a front end of the divider 130 may have at least one magnet that couples to at least one magnet having an opposite polarity and provided in a center of the front frame 141 of the upper frame 140. A bottom surface of a back end of the divider 130 may have at least one magnet that couples to at least one magnet having an opposite polarity and provided in a center of an upper surface of the back frame 144 of the upper frame 140 of the treadmill 1.

A front portion of the divider 130 may be wider than the rest of the divider 130 to provide stability. In addition, the front portion of the divider 130 may include a portion or mount 131 in which left and right proximity sensors 132 and 133 (e.g., laser sensor, radar sensor, or camera) may be provided. The proximity sensors 132 and 133 may sense a lateral distance (i.e., to the left or right) a pet may be from the divider 130. A height adjustment of the legs 411a, 412a, 421a, and 422a may be adjusted via the back and left height adjusters 410 and 420 according to positions of the pet sensed by the proximity sensors 132 and 133. In addition, since the lateral distance may be indicative of gait, speeds of the left and right belts 110 and 120 may be adjusted based on the positions of the pet sensed by the proximity sensors 132 and 133. Details of the back and left height adjusters 410 and 420 and a control process will be described later with reference to FIG. 36.

The left and right belts 110 and 120 may be easily replaceable with other belts having different textures corresponding to different exercise programs played through the display 210. For example, the left and right belts 110 and 120 may have a grassy (e.g., AstroTurf) and/or dirt texture, and the display 210 may show images of a grassy or hilly landscape. As another example, the left and right belts 110 and 120 may have a gravel, pavement, or concrete texture to correspond to road or sidewalk programs played on the display 210, respectively, a rocky or pebble texture to correspond to a mountain program played on the display 210, and/or a sandy texture (e.g., a GORE-TEX surface covering or holding sand or a rugged or rough surface imitating sand) to correspond to a beach program played on the display 210. The left and right belts 110 and 120 may also have a ribbed rubber texture or a texture that provides a substantial grip to prevent a pet from slipping. Alternatively or in addition thereto, the left and right belts 110 and 120 may have varied textures where, for example, certain portions are grassy and other portions are sandy to correspond to a program having varied terrains played on the display 210.

Regardless of a texture of the left and right belts 110 and 120, the left and right belts 110 and 120 may be made of an elastic material such that a tension is formed when the left and right belts 110 and 120 extend between the front rollers 112 and 122 and the back rollers 111 and 112, respectively. For the left and right belts 110 and 120 to be replaceable, the tension of the left and right belts 110 and 120 may be additionally adjusted via an optional tension adjuster.

Figure 7A:
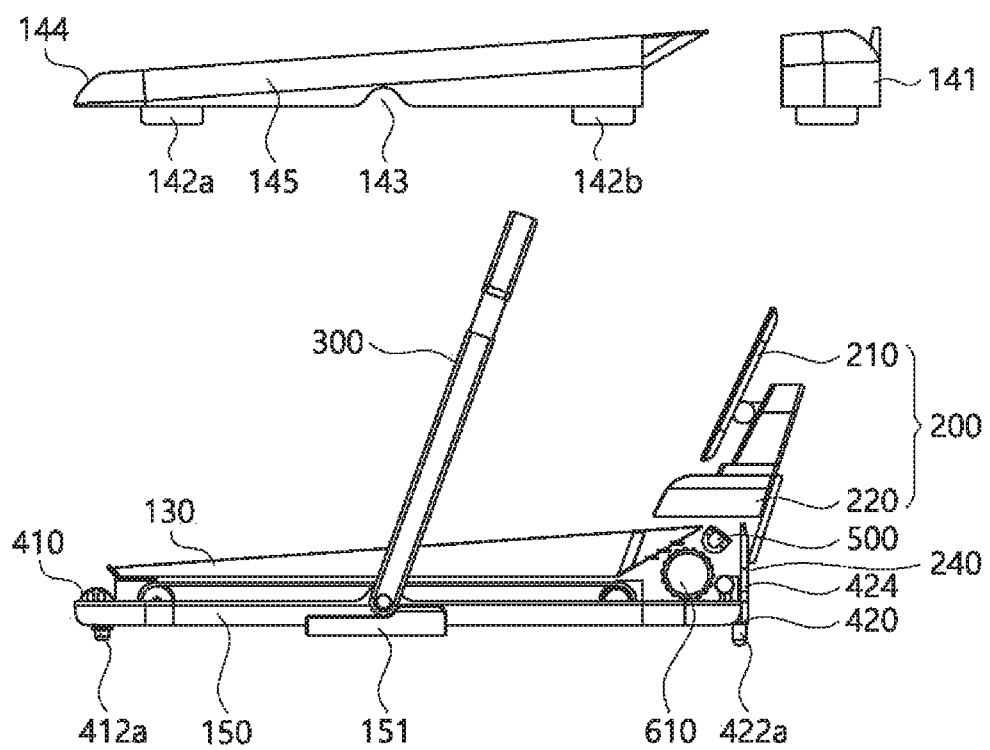
FIG. 7A is a side view of a treadmill according to an embodiment showing an upper frame of the base removed from the lower frame.
Figure 7B:
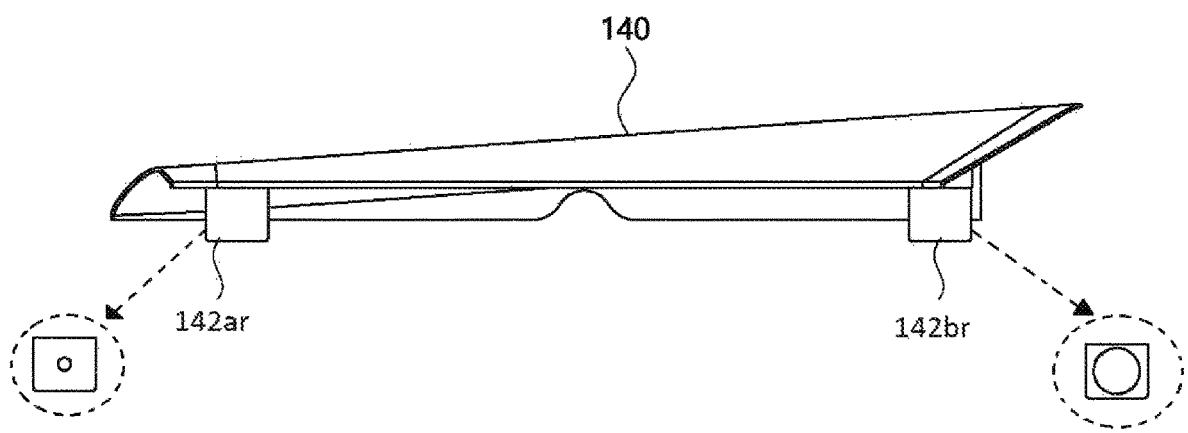
FIG. 7B shows a side view of an upper frame showing right roller frames according to an embodiment.
Figure 7C:
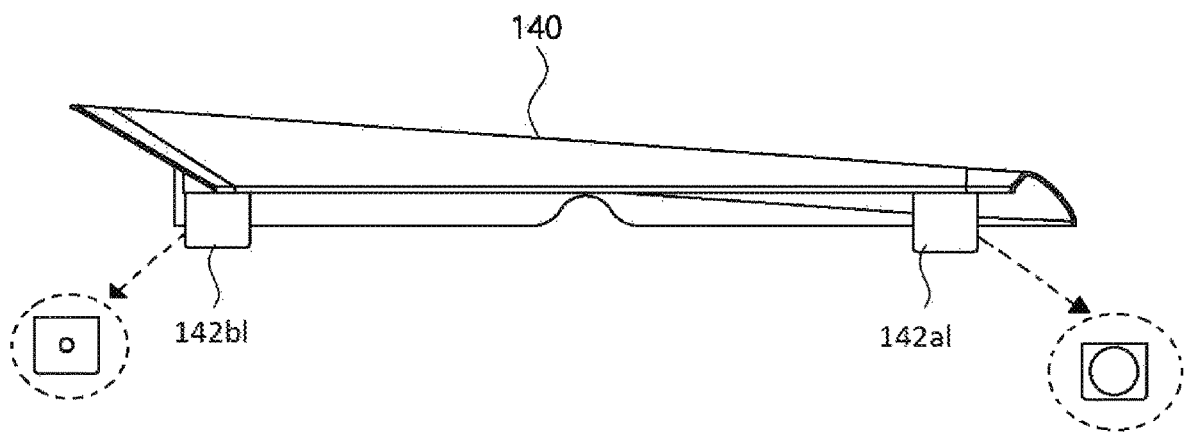
FIG. 7C shows a side view of an upper frame showing left roller frames according to an embodiment.

As shown in FIGS. 6 and 7A, the back shaft 115 and back motor 113 may be coupled between left and right back roller frames 142*a* (142*al* and 142*ar* in FIGS. 7B and 7C) of the upper frame 140, and the front shaft 125 and the front motor motor 123 may be coupled between left and right front roller frames 142*b* (142*bl* and 142*br* in FIGS. 7B and 7C). To loosen a tension of the left and right belts 110 and 120, the front and back shafts 125 and 115 may be removed from the front and back roller frames 142*b* and 142*a*, respectively. The front and back roller frames 142*b* and 142*a* may be configured to be stretchable or held under tension for removal of the rollers 111, 112, 121, and 122 from the front and back roller frames 142*b* and 142*a*. As an alternative, the front and back roller frames 142*b* and 142*a* may be provided on the lower frame 140.

A distance between the front roller frames 142*b* from the back roller frames 142*a* may be longer than a length of the closed loop left and right belts 110 and 120 and may be configured such that, when the front and back shafts 125 and 115 are coupled to the front and back roller frames 142*b* and 142*a*, tensions of the left and right belts 110 and 120 are at a predetermined tension. The predetermined tension may be strong enough to support a weight (e.g., 8 lbs.) of the pet.

Referring to FIGS. 6 and 7B, when looking at a side of the upper frame when viewed from the right, the back right roller tab 142*ar* and the front right roller tab 142*br* may be spaced apart by a predetermined distance that is less than a length of the closed loop left and right belts 110 and 120. As shown by the dotted circle near the rear of the upper frame 140, an inner side of the back right roller 142*ar* may have a circular groove configured to receive the back shaft 115.

As shown by the dotted circle near the front of the upper frame 140, the front right roller frame 142*br* may have a circular groove or recess configured to receive the front motor 123. The circular groove formed in the front right roller frame 142*br* for the front motor 123 may be larger than the circular groove formed in the back right roller frame 142*ar*.

Referring to FIGS. 6 and 7C, an orientation of the upper frame 140 is shown when viewed from the left. The front left roller frame 142*bl* and the back left roller frame 142*al* may be spaced apart by the predetermined distance.

As shown by the dotted circle near the front of the upper frame 140, the front left roller frame 142*bl* may have a circular groove or recess configured to receive the front shaft 125. The groove of the front left roller frame 142*bl* may face the groove of the front right roller frame 142*br* (FIG. 7B), which may receive the front motor 123. The groove of the front left roller frame 142*bl* may be smaller than the groove of the front right roller frame 142*br* (FIG. 7B).

As shown by the dotted circle near the rear of the upper frame 140, an inner side of the back left roller frame 142*al* may have a circular groove configured to receive the back motor 113. The groove of the back left roller frame 142*al* may face the groove of the back right roller frame 142*ar* (FIG. 7B), which may receive the back shaft 115. The groove of the back left roller frame 142*bl* may be larger than the groove of the back right roller frame 142*ar* (FIG. 7B) and the groove of the front left roller frame 142*bl*.

As can be appreciated by one of ordinary skill in the art, the size of the grooves on inner sides of the back roller frames 142*al* and 142*ar* and the front roller frames 142*bl* and 142*br* may be modified if an arrangement of the front and back motors 123 and 113 are modified. As an alternative, the back roller frames 142*al* and 142*ar* and the front roller frames 142*bl* and 142*br* may extend upward from the lower frame 120 instead of downward from the upper frame 140.

Figure 11:
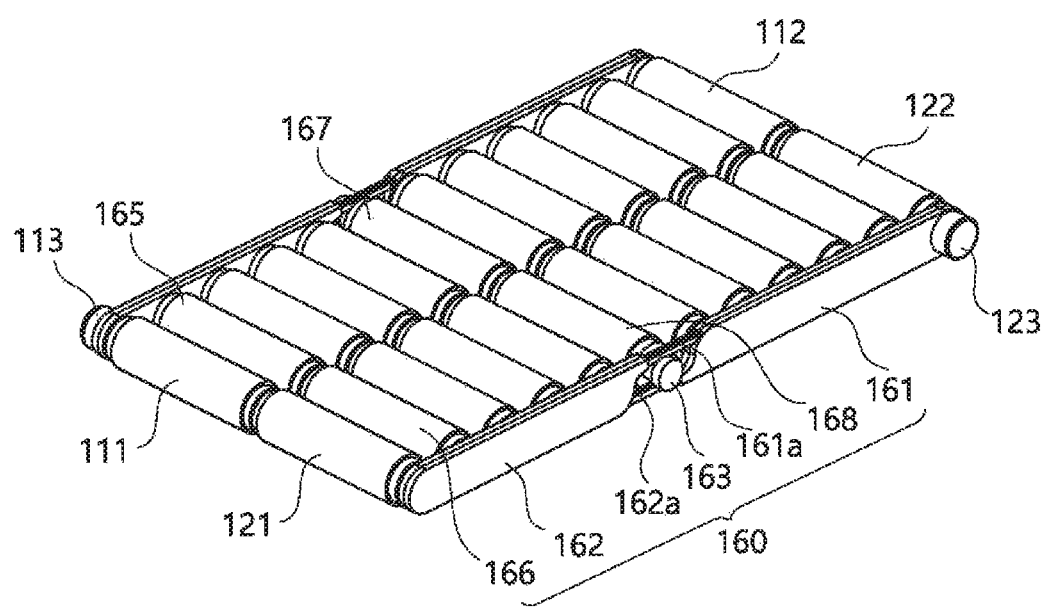
FIG. 11 is a perspective view of an optional roller frame of a treadmill according to an embodiment.
Figure 12:
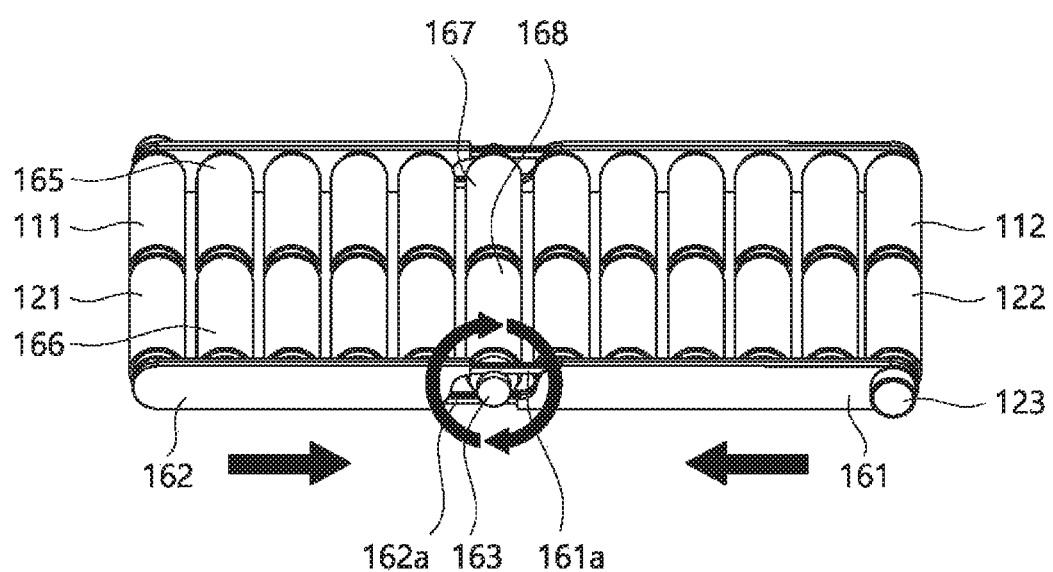
FIG. 12 is a side perspective view of the roller frame of FIG. 11 when a length is adjusted to be shortened.
Figure 13:
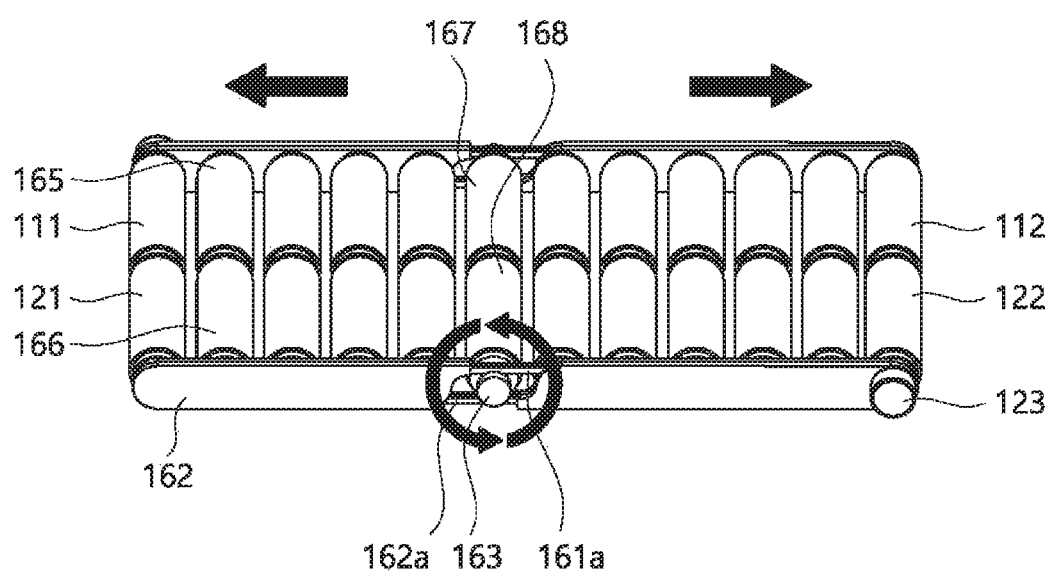
FIG. 13 is a side perspective view of the roller frame of FIG. 11 when a length is adjusted to be lengthened.
Figure 14:
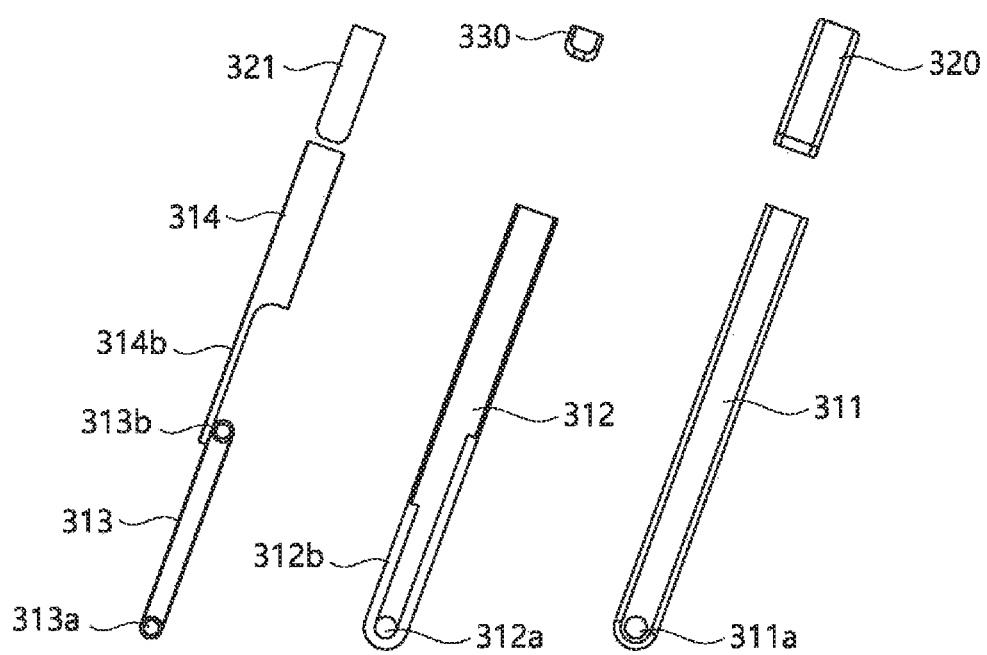
FIG. 14 is an exploded side view of a handle of a treadmill according to an embodiment.
Figure 15:
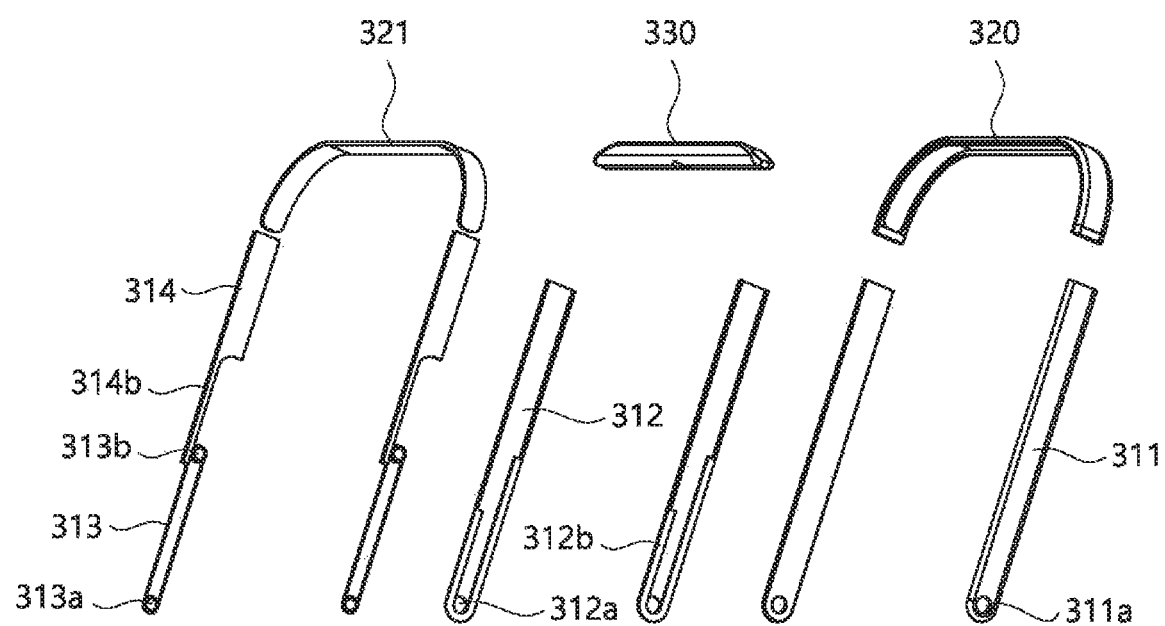
FIG. 15 is an exploded perspective view of the handle of FIG. 6.

Alternatively or in addition thereto, referring to FIGS. 11-13, there may be an optional roller frame or housing 160 provided inside of the base 100 to rest on the lower frame 150. The roller frame 160 may have an adjustable length, and the upper and lower frames 140 and 150 may have lengths that are longer than a maximum length of the roller frame 160.

The roller frame 160 may have a front frame 161 and a back frame 162 slideably coupled to the front frame 161. The front frame 161 may house the front shaft 125 on which the front rollers 112 and 122 are provided, and the back frame 162 may house the back shaft 115 on which the back rollers 111 and 112 are provided. Since the front and back frames 161 and 162 are slideably connected, a distance between the front and back shafts 125 and 115 may be adjusted to adjust tensions of the left and right belts 110 and 120. In such an embodiment, the front and back roller frames 142*b* and 142*a* may be modified to attach to (e.g., clip to or lock to) sides of the roller frames 160 or in addition to the front and back shafts 125 and 115 and the front and back motors 123 and 113. In another embodiment including the roller frame 160, the front and back roller frames 142*b* and 142*a* may be omitted or serve only to couple the upper frame 140 to the lower frame 150, and the upper frame 140 may have a separate tab or frame to attach to the roller frame 160.

Each of the front and back frames 161 and 162 may be formed of left and right plates or walls. The front right roller 122 may be inserted into an opening provided on an inner right side of the front frame 161, and the front left roller 112 may be inserted into a recess or groove provided on an inner left side of the front frame 161. The right motor 123 may be provided on an outer right side of the front frame 161 to insert into the opening and couple to the front right roller 122. The back right roller 121 may be inserted into a recess or groove provided on an inner right side of the back frame 162, and the back left roller 111 may be inserted into an opening provided on an inner left side of the back frame 162. The left motor 113 may be provided on an outer left side of the back frame 162 to insert into the opening and couple to the back left roller 111.

The front frame 161 may include an extension 161*a* extending from an inner end of the front frame 161 and inserted into a hole provided in an inner end of the back frame 162. The back frame 162 may similarly include an extension 162*a* extending from the inner end of the back frame 162 and inserted into a hole provided in the inner end of the back frame 162. The extension 161*a* of the front frame 161 may, for example, extend from an upper side of the inner end of the front frame 161, and the hole of the back frame 162 may be provided in an upper side of the inner end of the back frame 162. The extension 162*a* of the back frame 162 may extend from a lower side of the inner end of the back frame 162, and the hole of the front frame 161 may be provided in a lower side of the inner end of the front frame 161.

A gear or dial 163 may be provided between the extensions 161a and 162a. The dial 163 may include gear teeth provided on an outer circumferential surface to correspond to gear teeth provided on lower surfaces of the extensions 161a and 162a that contact the dial 163. When the dial 163 is turned in a first direction, the extension 161a may be pulled forward out of the hole of the back frame 162, the extension 162a may be pulled backward out of the hole of the front frame 161, and the length of the roller frame 160 may be increased. When the dial 163 is turned in a second direction opposite of the first direction, the extension 161a may be inserted backward into the hole of the back frame 162, the extensions 162a may be inserted forward into the hole of the front frame 161, and the length of the roller frame 160 may be decreased. There may be two sets of dials 163 and extensions 161a and 162a corresponding to left and right sides of the roller frame 160. The dials 163 may be operated automatically via a motor, or may be operated manually. A locking mechanism may be provided in the dial 163, the extensions 161a and 162a, and/or the holes of the front and back frames 161 and 162 to maintain a length of the roller frame 160 after adjustment.

There may be a plurality of rollers 165 and/or 166 extending between inner sides of the front and back frames 161 and 162, and a central pair of left and right rollers 167 and 168 coupled to the dials 163. When there are left and right belts 110 and 120, there may be a plurality of left rollers 165 provided between the left front and back rollers 112 and 111 and a plurality of right rollers 166 provided between the right front and back rollers 122 and 121. The pairs of left and right rollers 165 and 166 may be provided on single fixed shafts around which the left and right rollers 165 and 166 freely rotate.

The central pair of left and right rollers 167 and 168 may not be coupled to the front or back frame 161 or 162 and may remain stationary during a length adjustment process of the roller frame 160. When the length of the roller frame 160 is increased, pairs of left and right rollers 165 and 166 coupled to the front and back frames 161 and 162 may move further away from the central pair of left and right rollers 167 and 168. When the length of the roller frame 160 is decreased, pairs of left and right rollers 165 and 166 coupled to the front and back frames 161 and 162 may move closer to the central pair of left and right rollers 167 and 168. The plurality of left and right rollers 165 and 166 may support a weight of the pet (small, medium, or large pets) using the treadmill 1.

Referring to FIGS. 6-7 and 14-15, the upper frame 140 may include a handle mount opening 143, and the lower frame 150 may include a handle mount 153. The handle mount opening 143 may be an opening formed in a side surface of the side wall 145 (FIG. 7) having a size and shape that corresponds to a size and shape of the handle mount 153, which may extend upward from a sidewall of the lower frame 150. The handle mount 153 may be provided in the handle mount opening 143 when the upper frame 140 is coupled to the lower frame 150.

Figure 2:
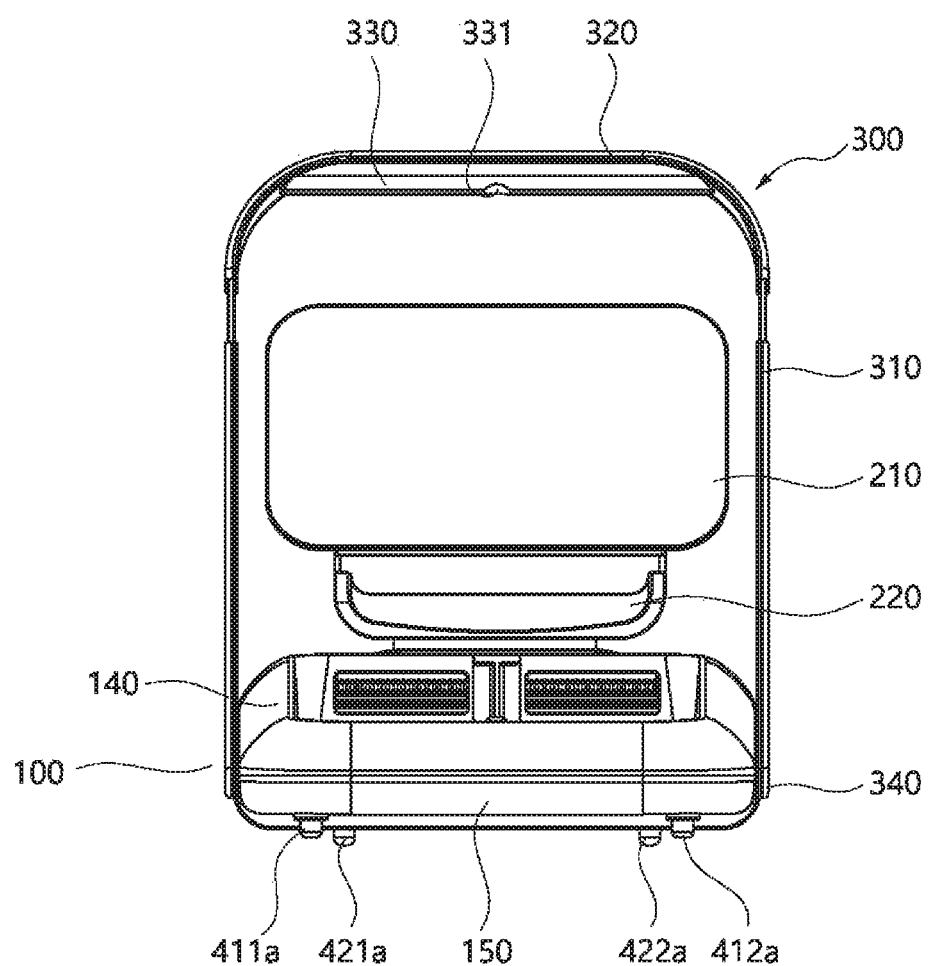
FIG. 2 is a front view of a treadmill according to an embodiment.
Figure 3:
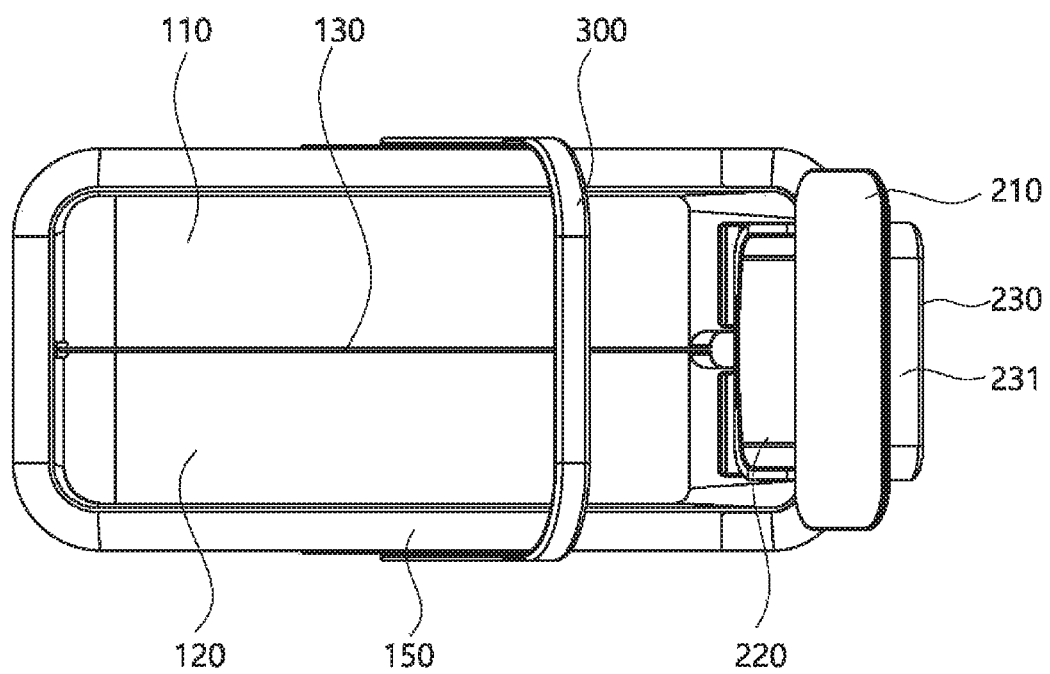
FIG. 3 is a top view of a treadmill according to an embodiment.

The handle 300 may be coupled (e.g., hinged) to the handle mount 153. Referring to FIG. 2, the handle 300 may include a handle bottom or side 310 hinged to the handle mount 153, a handle top 320, and a sensor assembly 330 having a handle sensor 331 (e.g., camera, image sensor, or infrared or laser sensor) coupled to a bottom surface of the handle top 320. A user may lift the treadmill 1 by the handle 300 to reposition or move the treadmill 1.

Figure 22:
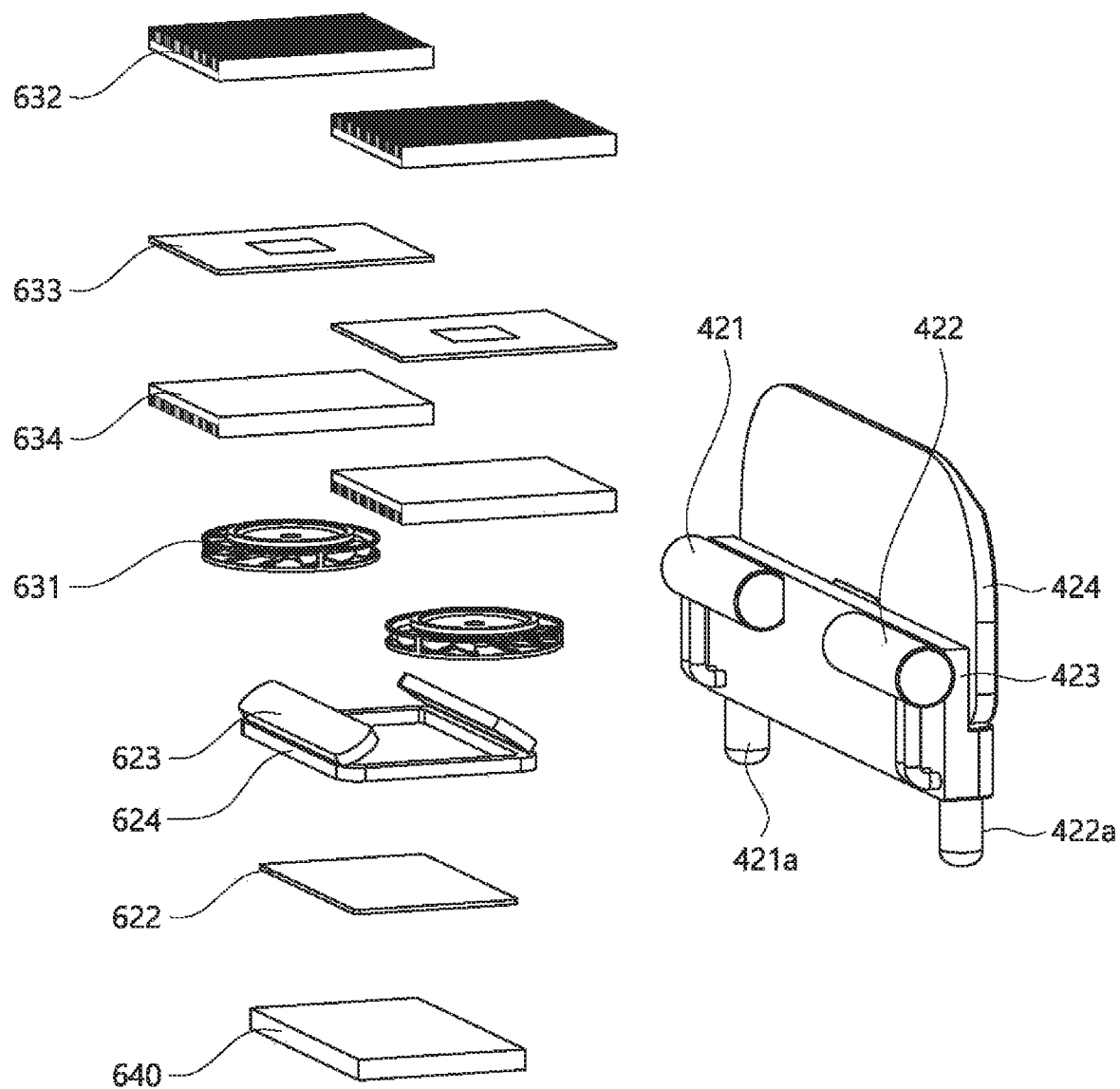
FIG. 22 is an exploded perspective view of a thermoelectric cooler and deodorizer according to an embodiment.
Figure 23:
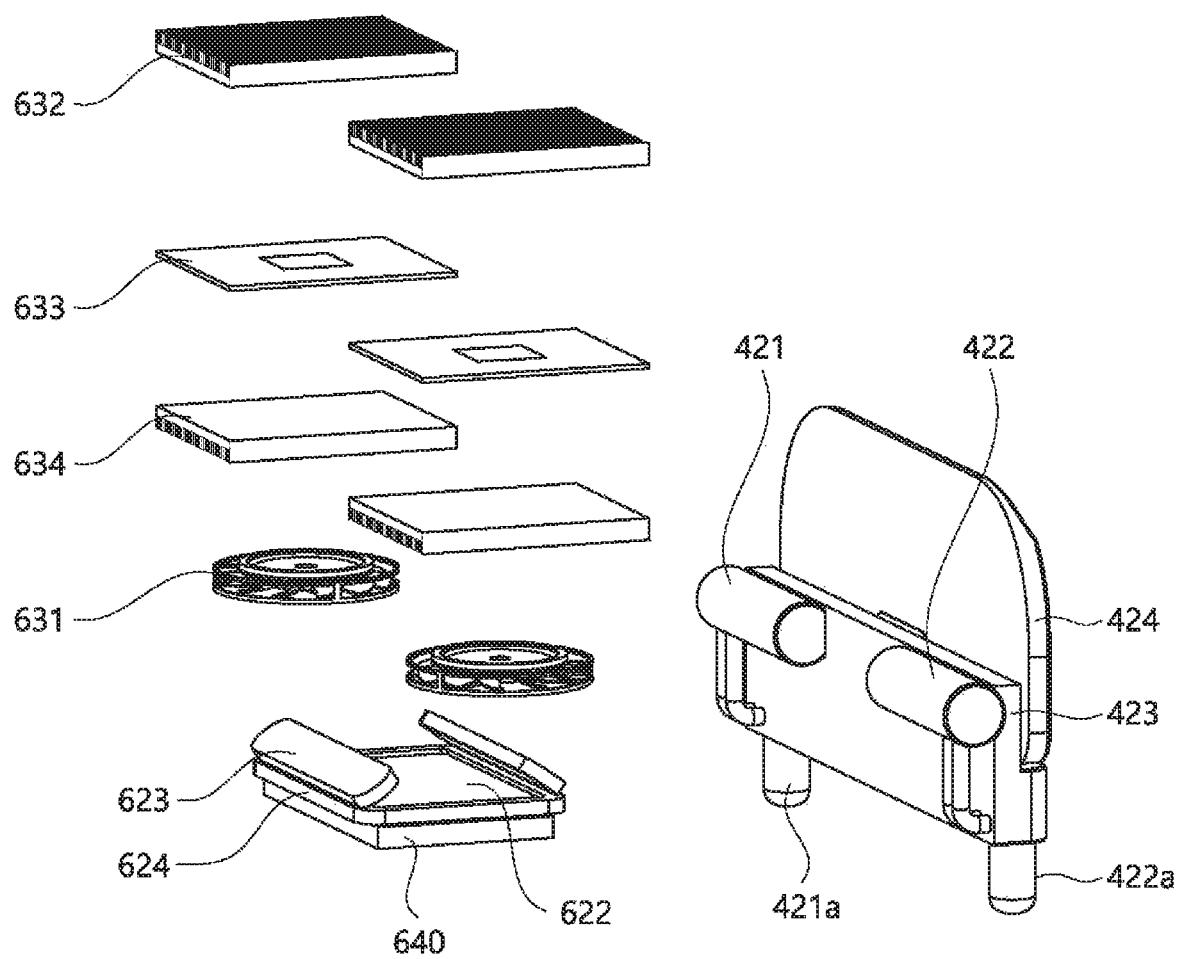
FIG. 23 is an exploded perspective view of the thermoelectric cooler of FIG. 22 and an assembled deodorizer of FIG. 22.

The handle sensor 331 may detect a pet present on the treadmill 1. The handle sensor 331 may provide positional information of the pet to a main controller of a control module 640 (FIGS. 22 and 23). The handle sensor 331 may use a camera to sense both a height of the pet and a forward-backward position on the left and right belts 110 and 120. The sensor assembly 330 may have a sub-PCB and/or a communication module that communicates with a communication module of the control module 640 described later. The motors 113 and 123 may be controlled according to a sensed forward-backward position of the pet on the left and right belts 110 and 120, and a height of the handle 300 may be controlled according to a sensed height of the pet. An inclination of the display 210 described later may also be controlled according to a sensed height or position of the pet.

The handle sensor 331 may sense whether a pet is within a predetermined distance range from the handle 300. If the handle sensor 331 senses that a pet is too far forward (or beyond a first predetermined position in front of the handle 300), the main controller may control the motors 113 and 123 of the rollers 111 and 122, respectively, to speed up a rotation so that a speed of the left and right belts 110 and 120 is increased and so that the pet may not accidentally walk off the left and right belts 110 and 120. If the handle sensor 331 senses that a pet is too far backward (or behind a second predetermined position in front of the handle 300), the main controller may control the motors 113 and 123 of the rollers 111 and 122, respectively, to slow down a rotation so that a speed of the left and right belts 110 and 120 is reduced and so that the pet may not be injured or slide off the left and right belts 110 and 120.

The handle bottom 310 may include an outer frame 311, an inner frame 312 coupled to the outer frame 311, and a base frame 313 coupled to a sliding frame 314 and provided between the inner and outer frames 312 and 311. The sliding frame 314 may be coupled to the handle top 320 and/or a bottom frame 321 of the handle top 320. The sliding frame 314 may slide relative to the base frame 313 to raise a height of the handle top 320. The base frame 313 and sliding frame 314 may be collectively referred to as a middle frame.

The sliding frame 314 may have a lower side 314b that couples to a gear or roller 313b provided on an upper end of the base frame 313. The lower side 314b of the sliding frame 314 may be narrower than an upper side of the sliding frame 314 coupled to the handle top 320. A surface of the lower side 314b that contacts the gear 313b may have teeth, and the teeth of the lower side 314b of the sliding frame 314 may correspond to teeth provided on an outer circumference of the gear 313b of the base frame 313. A lower end of the base frame 313 may include a motor 313a, which may rotate a belt coupled to the gear 313b. The gear 313b may rotate to move the lower side 314b of the sliding frame 314 up or down via the teeth of the gear 313b and the lower side 314b. There may be a stopper or rib provided on a lower end of the lower side 314b of the sliding frame 314 to prevent the sliding frame 314 from being detached from the base frame 313.

An inner surface of the inner frame 312 may include a stopper flange 312b having a first end and a second end. The stopper flange 312b may be a raised or protruding portion around an edge of a lower side of the inner frame 312. The first end may prevent the lower side 314b of the sliding frame 314 from being slid further down the base frame 313, while the second end may be at a height higher than the first end to prevent a lower portion of the upper side of the sliding frame 314 from being slid further down the base frame 313. A height difference between the first and second ends of the stopper flange 312b may be equal to height difference between the lower end of the lower side 314b of the sliding frame 314 and a lower end of the upper side of the sliding frame 314. A contact between the handle top 320 and upper ends of the inner and outer frames 312 and 311 may also prevent the sliding frame 314 from being slid further down the base frame 313.

The sliding frame 314 may be slid manually by a user lifting the handle top 320, or may be slid automatically via a motor 313a provided at a bottom end of the base frame 313. The motor 313a may raise or lower a height of the handle top 320 based on a sensed height of the pet by the handle sensor 331.

The inner and outer frames 312 and 311 may include holes 312a and 311a, respectively, that surround an outer circumference of the motor 313a. Alternatively, the hole 311a may be a cavity or recess formed in the outer frame 311 to accommodate the motor 313a. The base frame 313 may include a hinge shaft on a side opposite to a side where the motor 313a is provided, and the hinge shaft may penetrate through the hole 312a of the inner frame 312 to couple to a hinge hole provided in the handle mount 153. The handle 300 may rotate via the hinge shaft of the base frame 313 and hinge hole of the handle mount 153. There may be an optional motor provided in the handle mount 153 to automatically rotate the handle bottom 310 between a first or storage position and a second or exercise position.

Lengths of the sliding frame 314, base frame 313, and inner and outer frames 312 and 311 may be configured such that when the sliding frame 314 is slid away from the base frame 313 by a maximum amount, the handle 300 may fit around the front ends (or alternatively, the back ends) of the upper and lower frames 140 and 150. The treadmill 1 may be conveniently stored when the handle 300 is rotated so that the outer, inner, base, and sliding frames 311, 312, 313, and 314 are provided to be parallel to a longitudinal length of the lower frame 150. A user may carry the treadmill 1 by holding onto the upper and lower frames 140 and 150 when the handle top 320 is folded or by grabbing the handle top 320 in such a folded position.

When the handle 300 is folded to a first position, the treadmill 1 may be activated to be in a storage state. The handle bottom 310 may be parallel to a side of the base 100. In the storage state, various devices (e.g., the blower 610, thermoelectric cooling assembly 630, and the fragrance assembly 500) may be turned off to save power and prevent unintended scents from being emitted. The photocatalytic deodorizer 622 and sterilizing lights 191 and 192 described later may be activated in the storage state to deodorize the treadmill 1.

When the handle 300 is unfolded and rotated to a second position, the treadmill 1 may be activated to be in an exercise state. The cover 151 that covers the debris remover 180 may be coupled to the base 100 at a position that aligns with the handle mount 153, and sides of the cover 151 may be configured to prevent the handle 300 from rotating past the second position or past the first position. Sides of the cover 151 may serve as stoppers that limit the handle 300 within a rotation range defined by the first and second positions.

Referring to FIGS. 6 and 16-19, the treadmill 1 may further include a debris remover 180 provided under an opening 152 of the lower frame 150. The debris remover 180 may be configured to scrape off and collect pet fur and other debris on the left and right belts 110 and 120. The opening 152 of the lower frame 150 may be formed in a bottom surface of the lower frame 150, and may be partially formed in side surfaces of the lower frame 150. A shape and size of the opening 152 may correspond to a shape and size of the debris remover 180.

A cover 151 may be provided to be detachable from the lower frame 150 to cover the debris remover 180 and the opening 152. When the user removes the cover 151, the user may remove the debris remover 180 to dispose of any debris caught by the debris remover 180. Sides of the cover 151 may have a curvature that corresponds to an outer contour of the side surfaces of the lower frame 150. The sides of the cover 151 may extend upward to be snap-fitted onto the side surfaces of the lower frame 150. A first end (e.g., a front end) of the cover 151 may have side surfaces that extend higher than side surfaces of a second end (e.g., a back end).

The cover 151 may have a recess formed in a bottom surface in which the debris remover 180 may be inserted. A shape and size of the recess of the cover 151 may correspond to a shape and size of an outer contour of bottom and side surfaces of the debris remover 180. Sides of the cover 151 may have a curvature configured to correspond with a curvature of an outer side surface of the lower frame 150 of the base 100. The cover 151 may have a first edge and a second edge that is higher than the first edge. An angled edge may extend between the first and second edges. The handle bottom 310 may be mounted to the base 100 at a position adjacent to the angled edge. The first edge may maintain the handle bottom 310 in a position that is parallel to the side of the base 100, and may limit a position of the handle bottom 310 past the first position. The angled edge may maintain the handle bottom 310 in an upright position where the handle top 320 crosses over the left and right belts 110 and 120, and may limit a position of the handle bottom 310 past the second position. At the second position, the handle bottom 310 may be positioned at a predetermined angle away from a rear of the base 100. The predetermined angle may be an obtuse angle with respect to the rear of the base 100 or an acute angle with respect to the front of the base 100.

The debris remover 180 may be a rectangular hollow container or tray having an opening or hole 183 through which hair, fur, lint, or other debris may enter. A height of the debris remover 180 may be configured so as to rest below the left and right belts 110 and 120 without contacting the floor. The opening 183 may be provided on a protruding portion of the debris remover 180 that extends upward toward the left and right belts 110 and 120, which may be exposed to the debris remover 180 via the opening 152 in the lower frame 150. The protruding portion of the debris remover 180 may have an angled edge close to or in contact with the left and right belts 110 and 120. When a pet sheds hair onto the left and right belts 110 and 120, the protruding portion of the debris remover 180 may scrape or brush off the hair, and the hair may fall into the opening 183.

The protruding portion of the debris remover 180 may include a surface or scraper 184 configured to scrape debris off of the left and right belts 110 and 120 and induce a static charge, such as fabric, felt, sweeper, or a brush (e.g., microbrush, fine brush, or bristle brush) to catch hair and debris. For convenience of description, the surface or scraper 184 will be referred to as a brush 184. The brush 184 may also ionize the left and right belts 110 and 120 so that more hair may cling to the left and right belts 110 and 120 via static electricity instead of falling onto the lower frame 150 before reaching the opening 152 and the debris remover 180. The brush 184 and/or bristles of the brush 184 may have a stiffness that is sufficient to grab hair and clean a bottom surface of the left and right belts 110 and 120.

The opening 183 and brush 184 may be formed at an end end of the debris remover 180 to catch debris on a bottom section of the outer surfaces of the left and right belts 110 and 120, which may be moving in a backward direction (i.e., from a rear of the base 100 toward a front of the base 100) when a top section of the outer surfaces of the left and right belts 110 and 120 are moving in a forward direction (i.e., from the front of the base 100 toward the rear of the base 100) during an exercise program. The brush 184 may be provided on a leading edge of the opening 183 with respect to a movement of the bottom section of the outer surfaces of the left and right belts 110 and 120. The brush 184 and the opening 183 may extend below both the left and right belts 110 and 120.

The debris remover 180 may include a lower frame 181 and an upper frame 182. The upper frame 182 may include the opening 183, and may be pressed-fit onto the lower frame 181. The lower frame 181 may include a cavity or space in which hair is stored, and the upper frame 182 may close the space. The lower frame 181 may further include a recess 181b formed in a bottom surface. The recess 181b may optionally serve as a tray to hold a film of water or gel and to capture hair or debris received through the opening 183 and prevent hair from escaping out of the opening 183. Optional vents 181a and 151a may be formed at ends (e.g., front ends) of the bottom frame 181 and the cover 151, respectively, to drain any excess water or gel in the recess 181b.

A user may remove the cover 151 from the lower frame 150 to access the debris remover 180. The debris remover 180 may be removed from under the lower frame 150, and the user may separate the upper frame 182 from the lower frame 181 to empty the contents collected in the space of the debris remover 180. The user may also replace or refill water in the recess 181b.

Figure 19:
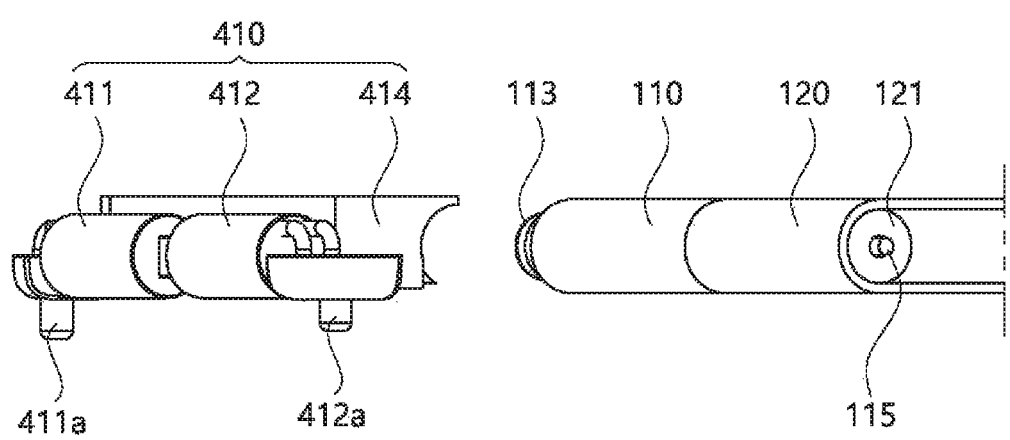
FIG. 19 is a perspective back view of a back height adjuster according to an embodiment.

Referring to FIGS. 6 and 19, a back height adjuster 410 may control lengths of back left and right legs 411a and 412a to control a back inclination of the treadmill 1. The back height adjuster 410 may be provided on the back end of the lower frame 150 under the back frame 141 of the upper frame 140. The back frame 144 of the upper frame 140 may be provided on a top surface of a rear frame or shield 414 of the back height adjuster 410. The back left and right legs 411a and 412a may be inserted through holes provided on back corners of a bottom surface of the lower frame 140.

The back height adjuster 410 may adjust the back left and right legs 411a and 412a via air suspension, as oil or other liquid used in hydraulic movement may interfere with a scent or smell released by the fragrance assembly 500. However, embodiments disclosed herein are not limited to air suspension methods. The back height adjuster 410 may include left and right air suspension compressors and pumps to independently adjust a height of the back left and right legs 411a and 412a, respectively. The back height adjuster 410 may include left and right air tanks 411 and 412, and at least one printed circuit board to independently control the left and right air tanks 411 and 412 and therefore a height adjustment of the left and right legs 411a and 412a based on signals received from the main controller of the control module 640.

The left and right air tanks 411 and 412 may be coupled to a back side of the rear shield 414 of the back height adjuster 410. The rear shield 414 may serve as a frame that separates the back height adjuster 410 from the back rollers 111 and 121. The rear shield 414 may be fixed to the lower frame 150 so that when lengths of the back left and right legs 411a and 412a are lengthened, respective corners of the lower frame 150 are lifted to adjust an inclination of the treadmill 1.

The left and right legs 411a and 412a of the back height adjuster 410 may each include an inner or lower pipe or piston inserted into an outer or upper pipe. The outer pipe may be fixed to the height adjuster 410 and/or the lower frame 150. When the left air suspension compressor and pump is driven to pump air from the left air tank 411, the inner piston may be driven downward, and the outer pipe may rise relative to the inner piston to lift the left corner of the treadmill 1. An overlapping length of the inner piston and outer pipe may decrease during a lifting process, while the overlapping length is increased during a lowering process where the outer pipe may lower onto the inner piston as the inner piston is inserted further into the outer pipe.

Figure 20:
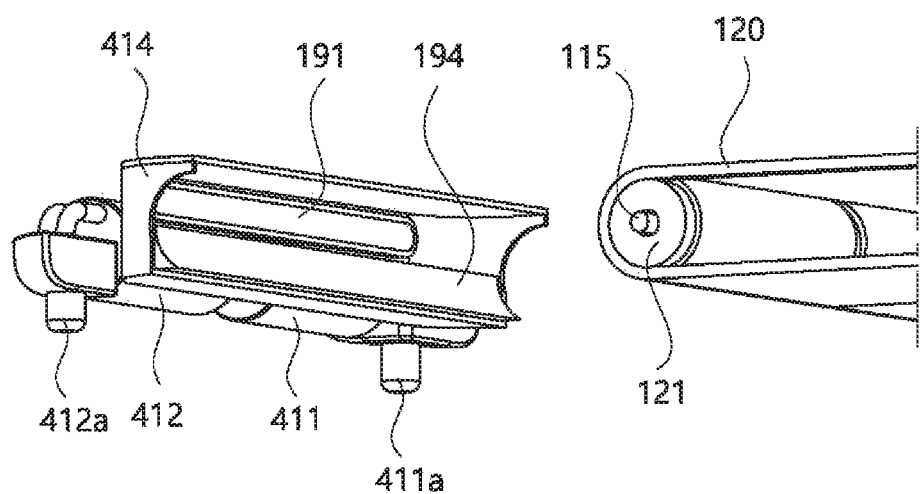
FIG. 20 is a perspective front view of the back height adjuster and UV light of FIG. 19.

Referring to FIGS. 6 and 20, a front side of the rear shield 414 of the back height adjuster 410 may include a roller cover 194 to partially cover and/or divide the back rollers 111 and 121 from the back left and right air tanks 411 and 412. The back roller cover 194 may have a concave curvature so as not to interfere with a rotation of the back rollers 111 and 121. Similarly, side surfaces of the rear shield 414 of the back height adjuster 410 may have a curved shape or concave opening so as not to interfere with a rotation of the back rollers 111 and 121.

The left and right belts 110 and 120 may collect sweat, slobber, or bacteria during exercise. The left and right belts 110 and 120 may be sterilized or cleaned by back and front sterilizing lights 191 and 192 provided at the back and front ends of the treadmill 1, respectively. The back and front sterilizing lights 191 and 192 may face the left and right belts 110 and 120, and may sterilize a greater portion of the left and right belts 110 and 120 as the left and right belts 110 and 120 move. The back and front sterilizing lights 191 and 192 may operate in a storage mode, for a predetermined sterilization time period, or periodically at set intervals.

The back sterilizing light 191 may include at least one ultraviolet (UV) light emitting diode (LED). For convenience of description, the back sterilizing light 191 will be referred to as a back UV LED 191. The back UV LED 191 may emit UV light configured to kill or inactivate bacteria or other microorganisms, such as UV-C light (e.g., light having a wavelength between 220-280 nm).

The back UV LED 191 may be provided on a front surface of a rear frame or shield 414 of the back height adjuster 410 to face the back left and right rollers 111 and 121. The rear shield 414 may have a top plate or portion configured to prevent UV light from being irradiated upward or outside of the upper frame 140. The back UV LED 191 may be provided above the roller cover 194. The roller cover 194 may include a sub-printed circuit board (PCB) to control an operation of the back UV LED 191 and/or a height adjustment of the left and right legs 411a and 412a. The back UV LED 191 may have a length extending in a longitudinal direction of the back left and right rollers 111 and 121, and may be provided at a center such that a left portion of the back UV LED 191 sterilizes the left belt 110, and a right portion of the back UV LED 191 sterilizes the right belt 120.

Figure 21:
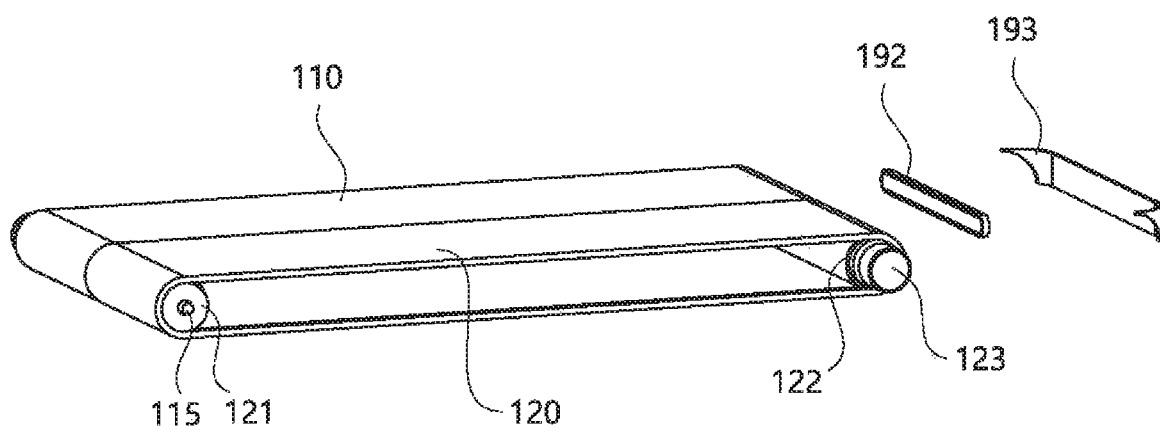
FIG. 21 is a perspective view showing a side of a front roller cover and UV light according to an embodiment.

Referring to FIGS. 6 and 21, the front sterilizing light 192 may similarly include at least one UV LED. For convenience of description, the front sterilizing light 192 will be referred to as a front UV LED. The front UV LED 192 may emit UV light configured to kill or inactivate bacteria or other microorganisms, such as UV-C light (e.g., light having a wavelength between 220-280 nm). The front UV LED 192 may be provided on a back surface of a front roller cover 193. Like the back roller cover 194, the front roller cover 193 may separate the front rollers 112 and 112 from a front portion of the base 100 including the blower 610 and the fragrance assembly 500 described later. The front roller cover 193 may have side surfaces that are curved or have concave openings so as not to interfere with a rotation of the front rollers 112 and 122.

The front UV LED 192 may have a length extending in a longitudinal direction of the front left and right rollers 112 and 122, and may be provided at a center of the front roller cover 193 such that a left portion of the front UV LED 192 may sterilize the left belt 110 and a right portion of the front UV LED 192 may sterilize the right belt 120. The front UV LED 192 may be provided in an upper portion or side of the front roller cover 193, while a PCB may be optionally provided in a lower side of the front roller cover 193 to control an operation of the front UV LED 192. A shape of the front roller cover 193 may be configured to prevent UV light from being irradiated upward or outside of the upper frame 140.

Figure 4:
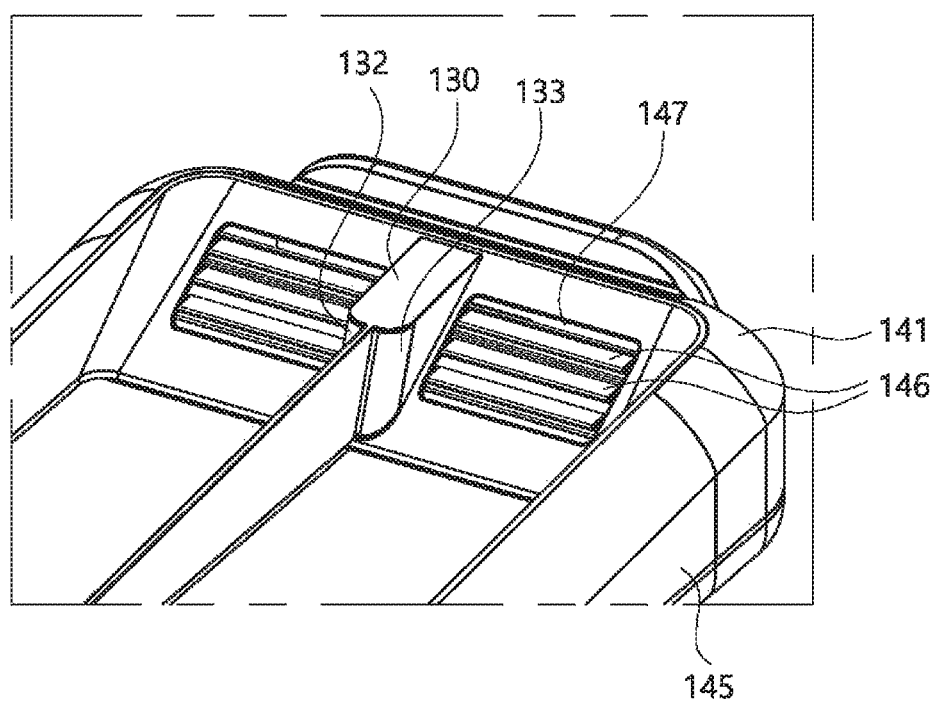
FIG. 4 is a perspective view of a front of a treadmill according to an embodiment.
Figure 5A:
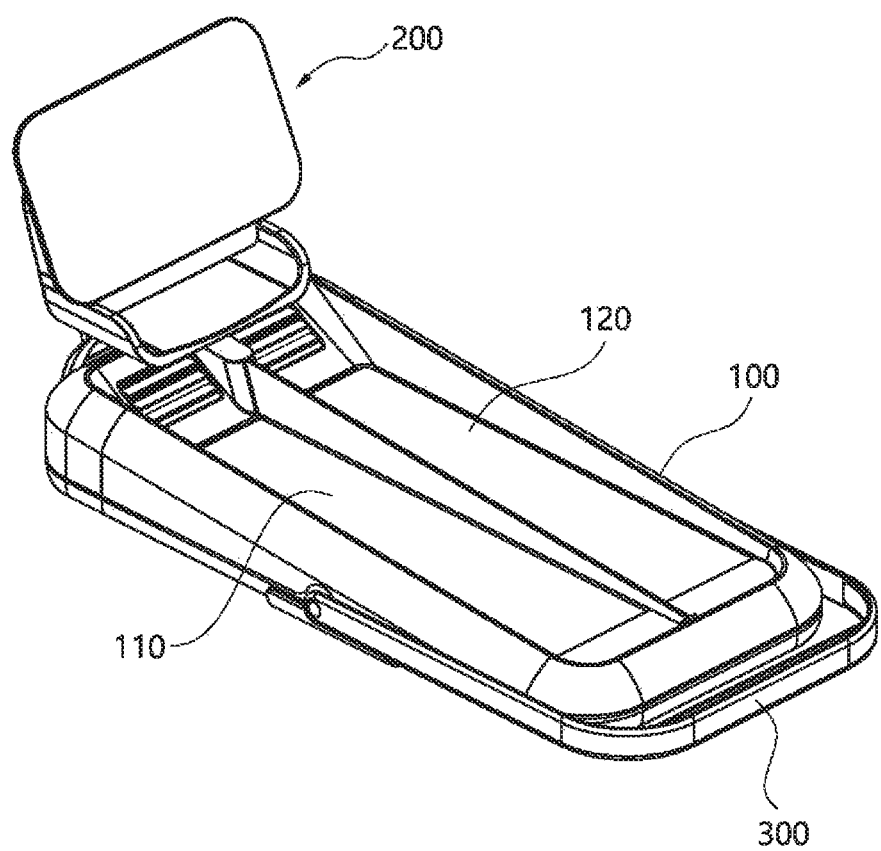
FIG. 5A is a view of a treadmill with a handle folded in a storage state showing an attachment module.
Figure 5B:
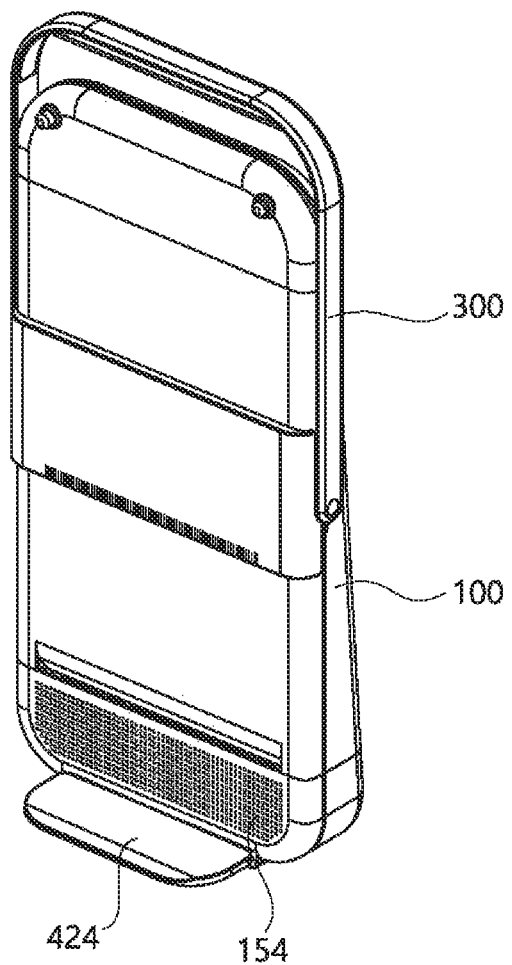
FIG. 5B is a view of a treadmill with the attachment module removed and stored in an upright position with a handle folded in a storage state.

The front roller cover 193 may divide the left and right belts 110 and 120 from a space under the front frame 141 that includes the fragrance assembly 500, the blower 610, and the front height adjuster 420 (see FIG. 4). Referring to FIGS. 6, 22, and 23, the front height adjuster 420 may operate similarly to the back height adjuster 410 via air suspension. The front height adjuster 420 may include front left and right legs 421a and 422a that are independently controlled by left and right air suspension compressors and pumps and at least one printed circuit board. The front height adjuster 420 may include left and right air tanks 421 and 422, and the printed circuit board may independently control the left and right air tanks 421 and 422 based on signals received from the main controller of the control module 640.

Each of the front left and right legs 421a and 422a may include an outer or upper pipe or piston and an inner or lower pipe. When an air pressure is applied by, e.g., the left air tank 421, the outer pipe of the front left leg 421a may rise relative to the inner pipe or piston to raise a height of the front left leg 421a and therefore a front left corner of the treadmill 1.

The four legs 411a, 412a, 421a, and 422a of the treadmill 1 may be provided at or near corners of the base 100 and independently controlled so that a tilt or inclination of the treadmill 1 may be varied and customized according to a program played on the display 210. The front left and right legs 421a and 422a may extend from a lower surface of the front support 420. When a height of at least one of the front right and left legs 421a and/or 422a is adjusted, heights of corresponding corners or sides of the upper and lower frames 140 and 150 may also be adjusted.

For example, the front height adjuster 420 may raise, via the front left and right air suspensions compressors and pumps, the front left and right legs 421a and 422a by equal amounts to create a constant inclination of the treadmill 1 to correspond to, for example, a hill program. As another example, the front height adjuster 420 may raise, via the front right air suspension compressor and pump, only the front right leg 422a, and the back height adjuster 410 may raise, via the back left air suspension compressor and pump, only the back left leg 411a to simulate a rocky or mountain terrain.

A front support 423 on which the left and right air tanks 421 and 422 of the front height adjuster 420 may be provided in front of the blower 610. A stand 424 may be coupled to the front support 423. The front frame 141 of the front support 420 may be provided on an upper surface of the front support 423 to cover the left and right air tanks 421 and 422. The front end of the lower frame 150 may also be securely fixed (e.g., bonded or welded) to sides of the front support 423. The stand 424 may serve as a base or support when the treadmill 1 is stored (see FIG. 5B). The stand 424 may be coupled to a display mount 211 described later when the attachment module 200 is attached.

Referring to FIGS. 6 and 22-24, the blower 610 may be a radial bladed fan or wheel 610 provided at a front of the treadmill 1. The deodorizer 620 and the thermoelectric cooling assembly 630 may also be provided at the front of the treadmill 1. The blower 610 may be a tangential fan or cross-flow blower to disperse scents from the fragrance assembly 500, disperse cool or warm air from the thermoelectric cooling assembly 630, and/or disperse air deodorized by the photocatalytic deodorizer 622 of the deodorizer 620. The blower 610 may have a cylindrical shape and a length corresponding to a length of the front frame 144 and/or a length corresponding to a length of the vents 146 to facilitate laminar air flow through the vents 146.

The thermoelectric cooling assembly 630 may include a thermoelectric cooler (TEC) or Peltier device 633. Above and below the Peltier device 633 may be top and bottom heat sinks 634 and 632, respectively. The top and bottom heat sinks 634 and 632 may each have a heat dissipation plate provided on the Peltier device 633, and may have radiating fins extending upward and downward, respectively, from the heat dissipation plates of the top and bottom heat sinks 634 and 632.

The Peltier device 633 may electrically connect to a control module 640 described later, and may receive a current to cool or warm air dispersed through the vents 146 by the blower 610. When a voltage is applied to the Peltier device 633, heat may be transferred from a first side (e.g., upper side) to a second side (e.g., bottom side) such that there is a temperature difference between the first and second sides.

A fan 631 may be provided below the bottom heat sink 634 and above discharge holes 154 (FIG. 5) provided in a bottom surface of the lower frame 150. A motor may rotate a shaft of the fan 631 to exhaust hot air during a cooling process (or alternatively, cool air in a heating process) dissipated by the bottom heat sink 634 through the discharge holes 154.

During a cooling process, the upper side of the Peltier device 633 may become cold, causing the top heat sink 632 to become cold, resulting in a drop in temperature of the ambient air, which is blown by the blower 610. The bottom side of the Peltier device 633 may become hot, causing the bottom heat sink 634 to become hot, resulting in an increased temperature of the ambient air, which his exhausted out of the discharge holes 154 by the fan 610. During a heating process, the upper side of the Peltier device 633 may become hot, and hot air near the top heat sink 632 may be drawn through the vents 146 via the blower 610. The bottom side of the Peltier device 633 may become cold, and cold air may be exhausted out of the discharge holes 154 via the fan 610.

A temperature of the pet may be sensed by the handle sensor 331 and/or the left and right proximity sensors 132 and 133, which may include an infrared sensor or a thermometer. Alternatively or in addition thereto, there may be another optional temperature sensor. During exercise, a temperature of the pet and/or ambient air may be maintained, via an operation of the Peltier device 633, at a predetermined temperature or temperature range. As an example, the ambient air above the left and right belts 110 and 120 and/or surrounding the treadmill 1 may be maintained at a temperature between 15-18° C. or between 59-65° F.

The fan 631 may rotate at a greater speed than the blower 610 and may generate a greater airflow than the blower 610. There may be two sets of fans 631, Peltier device 633, and top and bottom heat sinks 634 and 632 corresponding to left and right sides of the treadmill 1. Positions of the fan 631, Peltier device 633, top and bottom heat sinks 634 and 632, blower 610, and vents 146 may be configured so that warm or cool air may be drawn by the blower 610 and dispersed through the vents 146.

The deodorizer 620 may neutralize pollutants or odor particles in the air above the left and right belts 110 and 120. The deodorizer 620 may include two LED modules 623 protruding from a photocatalyst housing 624 and oriented toward a photocatalytic deodorizer 622. The LED modules 623 may each include at least one light emitting diode and emit light of a visible wavelength of a specific color temperature, e.g., 1,000-10,000 kelvin, on the photocatalytic deodorizer 622. Alternatively, the LED modules 623 may emit UV light. The photocatalyst housing 624 may be provided to house and surround the photocatalytic deodorizer 622. The photocatalyst housing 624 may have an opening or hole through which the photocatalytic deodorizer 622 is exposed toward the LED modules 623.

A bottom surface or side of the LED modules 623 may be coupled to an upper surface of the photocatalyst housing 624, and the LED modules 623 may be positioned to be inclined so that the light emitting diode may emit light toward the photocatalytic deodorizer 622. The LED modules 623 may have a length less than or equal to a length of the sides of the photocatalyst housing 624 on which they are mounted.

The photocatalytic deodorizer 622 may be made of or coated in a material having strong oxidizing properties (e.g., titanium or titanium dioxide ($TiO_2$)) so when the LED modules 623 shine light on the photocatalytic deodorizer 622, the photocatalytic deodorizer 622 may be activated to release or emit electrons or ions that react with the air at or near the treadmill 1 to break apart pollutants. The blower 610 may disperse the emitted ions through the vents 146 to deodorize air outside of the base 100. The deodorizer 620 may remove odors from the air around the treadmill 1 and/or a pet or pet odor remaining on the treadmill after the pet has exercised or while the pet is exercising. The deodorizer 620 may operate when the treadmill 1 is not being used and the fragrance assembly 500 is in a closed state so as not to emit any scents or fragrances, which can be neutralized by the ions.

The control module 640 may also be provided in the space between the front roller cover 193 and the second height adjuster 420. The control module 640 may be provided under the photocatalytic deodorizer 622, and may include a main controller on a main printed circuit board (PCB) that controls a power supply to the motors of the fans 631, the motor 313a of the handle 300, an operation of the display 210, etc. The control module 640 may further include an alternating current/direct current (AC/DC) converter to convert external AC power to DC power to power the fans 631, motor 313a, display 210, UV LEDs 191 and 192, LED modules 623, etc. External power may be applied to a terminal or socket provided on the base 100 of the treadmill 1. The terminal or socket may be provided at the front end of the base 100 and may be electrically coupled to the control module 640.

The control module 640 may have a communication module to communicate with communication modules of other devices (e.g., communication modules of the back and front height adjusters 410 and 420 or in the sensor assembly 330 of the handle 300). The communication module of the control module 640 may also communicate with a server, and/or may include a WiFi or Bluetooth module so that a user (e.g., pet owner) may control the treadmill 1 from a mobile or web application. Through a web/mobile application, the owner's image/video and voice may be provided on the display 210 with audio, and an embedded camera and microphone on the display 210 may be used to transmit the pet's image/video to a mobile or remote device (e.g., computer or mobile phone) via the communication module.

The communication module of the control module 640 may also interact with a pet pendant or pet identification tag having a GPS tracker. When the main controller determines that the owner is away (based on GPS data from the owner's phone) but that the pet is still at home (based on GPS data from the GPS tracker in the pet pendant), the treadmill 1 may turn on the display 210, dispense treats on the dispensing tray 220, or emit smells or scents via the fragrance assembly 500 to lure the pet to the treadmill 1. A luring and rewards process will be described in more detail later after describing the fragrance assembly 500 and display 210.

Figure 25:
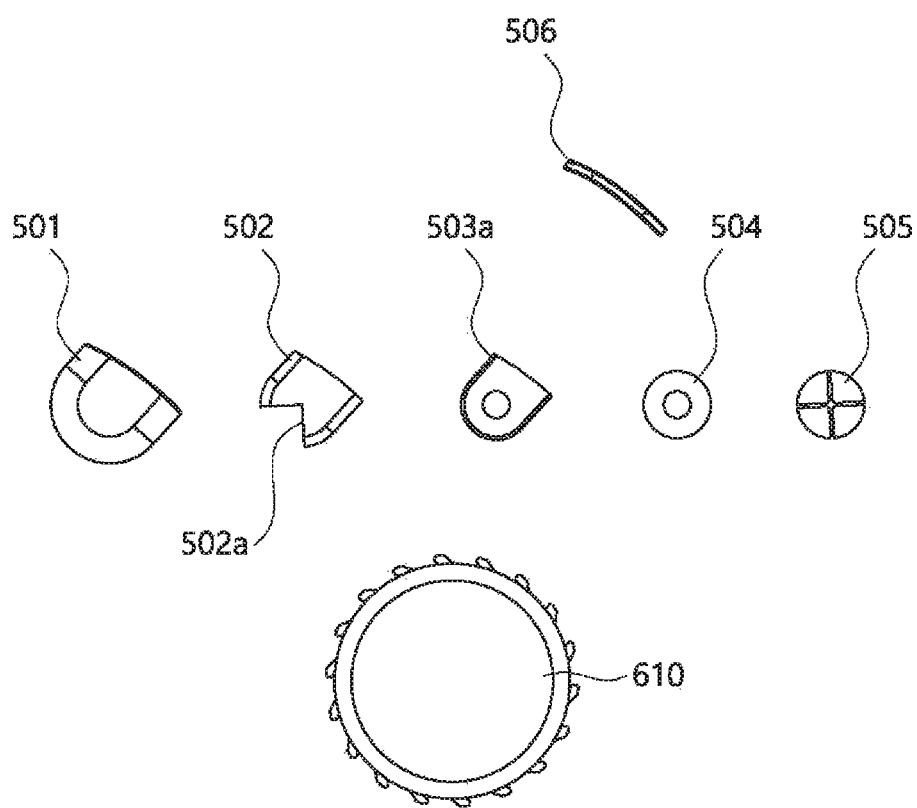
FIG. 25 is an exploded side view of a fragrance assembly according to an embodiment.
Figure 26:
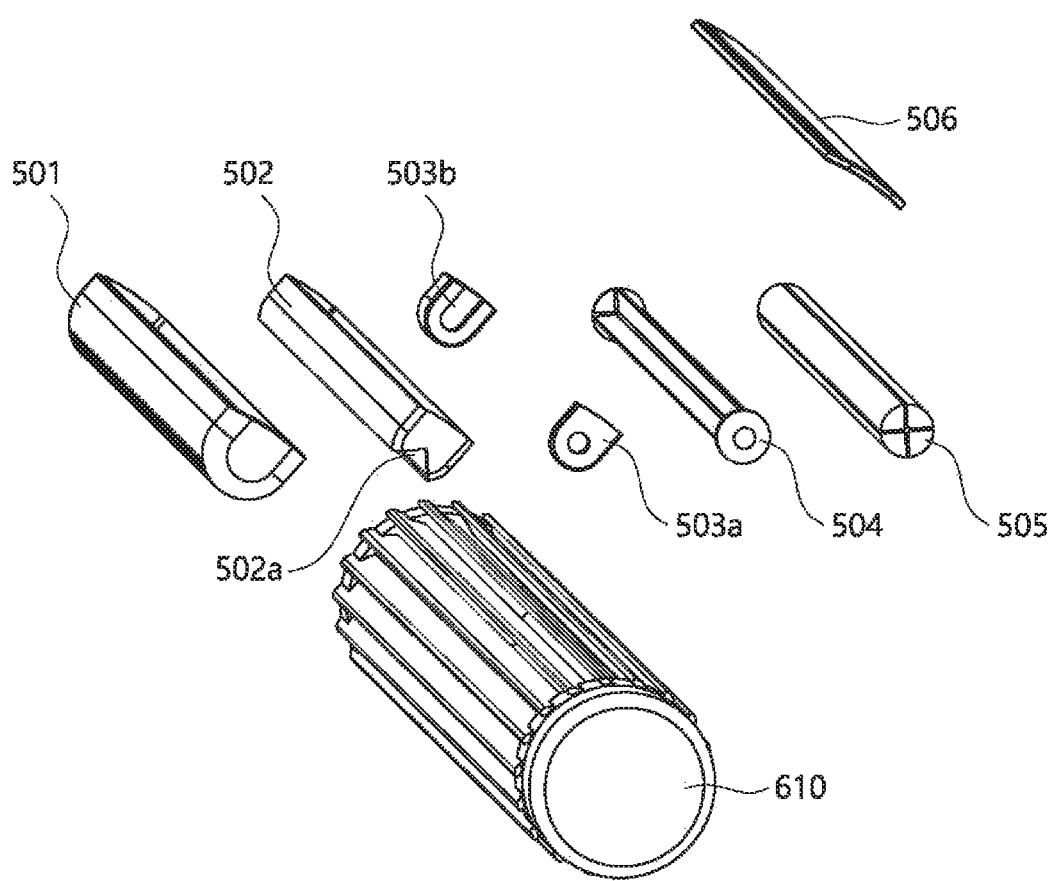
FIG. 26 is an exploded perspective of the fragrance assembly of FIG. 25.

Referring to FIGS. 6 and 25-26, the fragrance assembly 500 may include a cartridge 504 having a plurality of scent modules 505 provided in the cartridge 504. The cartridge 504 may be provided in an inner case 502 having an opening 502a through which the scent modules 505 are exposed, and the cartridge 504 may rotate to expose a particular scent module 505 through the opening 502a of the inner case 502. The blower 610 may rotate to disperse a scent and/or fragrance from the exposed scent module 505 through the vents 146 and to a pet using the treadmill 1.

The cartridge 504 may be divided into sections by tabs or walls, and different scent modules 505 may be provided in different sections of the cartridge 504. Shapes of the scent modules 505 may correspond to shapes of the sections of the cartridge 504 in which the scent modules 505 are inserted. As exemplified in the figures, the cartridge 504 may be formed by four vertical walls perpendicular to each other and intersecting at a center to create four 90° corners. Side ends of the cartridge 504 may each have a circular cap.

The four vertical walls may have a length that is parallel to a length of the blower 610. The scent modules 505 may have a length equal to or less than the length of the four vertical walls. As exemplified in the figures, the scent modules 505 may resemble elongated wedges having 90° corners that are inserted into the corners created by the four vertical walls, and having a curved or arc-shaped circumference to match a curvature of the cap provided at the sides of the cartridge 504. When the scent modules 505 are inserted into the cartridge 504, the cartridge 504 and the scent modules 505 may together form a cylinder.

The scent modules 505 may be made of a scented oil, wax, or gel that is in a primarily solid state that vaporizes when a temperature is slightly risen and/or emits scented vapor or fragrances. Alternatively, the scent modules 505 may be made of an absorbent or sponge-like material (e.g., felt) that is soaked in a liquid fragrance material. The blower 610 may draw out and disperse the scent provided by the scent modules 505. As pets may be sensitive to smell, the blower 610 may draw out the scent provided from the scent modules 505 instead of blowing or pushing the scents from behind the fragrance assembly 500. Such a configuration of the blower 610, fragrance assembly 500, and vents 146 may reduce a possibility of mixing smells. In addition, an outer layer of each scent module 505 may have an optional neutral smelling or protective layer to serve as a barrier, and the scent released from the scent module 505 may be stronger or dispersed further when the blower 610 rotates, and may be weaker or not dispersed very far when the blower 610 stops rotating.

As an example, the cartridge 504 may hold a first scent module 505 that emits a flower flagrance to correspond to a video displaying flowers along a road or trail played on the display, a second scent module 505 that emits a sea or beach fragrance to correspond to a seaside or beach video played on the display, a third scent module 505 that emits phytoncide or a forest fragrance to correspond to a forest or woods themed video played on the display, and a fourth scent module 505 that emits no fragrance or a neutral fragrance. Alternatively, a fourth section of the cartridge 504 may not include a fourth scent module 505 and may remain empty.

The cartridge 504 may be placed between two side supports 503a and 503b, and the cartridge 504 and the side supports 503a and 503b may be placed in the inner case 502. At least one of the side supports 503a or 503b may include a motor to rotate the cartridge 504. In FIG. 26, side support 503b includes a motor. The inner case 502 may have a hollow, truncated cylinder shape. The inner case 502 may have an opening 502a that is cut into a bottom or side surface, and the opening 502a may have a shape that corresponds to a shape of one scent module 505. The opening 502a may be slightly smaller than the shape of the scent module 505 (e.g., the opening 502a may have an 88° corner) so that no other scents from other scent modules 505 may be exposed through the opening 502a.

The cartridge 504 may rotate so that only one scent module 505 is exposed through the opening 502a. A rotation of the cartridge 504 may be automatic via the motor, and a fragrance emitted by the fragrance assembly 500 to the pet may be changed by a change of an exposed scent module 505 via a rotation of the cartridge 504. For example, the first scent module 505 having a flower or floral fragrance may be exposed through the opening 502a when a flower program or flowery road is played on the display 210. When the display 210 changes to show a forest scene, the cartridge 504 may rotate in the inner case 502 until the third scent module 505 emitting a phontycide or forest scent is exposed through the opening 502a.

The cartridge 504 may rotate to expose the blank, fourth scent module 505 to close the fragrance assembly 500. The cartridge 504 may be rotated to expose the fourth scent module 505 when the treadmill 1 is in a storage state, when the treadmill 1 is not being used, and/or when the deodorizer 620 is operated. Therefore, the other odors of the scent modules 505 will not break down by the ions emitted by the photocatalytic deodorizer 622. Alternatively, the opening 502a may be closed by an optional automatic gate provided in the inner case 502a.

The inner case 502 holding the cartridge 504 may be placed into the cartridge case 501. The cartridge case 501 may have a truncated cylinder shape. A cover or lid 506 may be configured to close a flat or truncated upper opening of the cartridge case 501 so that unintended fragrances do not escape or are not emitted toward the pet using the treadmill 1. The cover 506 may be pressed fit onto the cartridge case 501, and may have grooves or recesses formed in an upper surface in which a user may wedge a finger or nail to remove the cover 506 from the cartridge case 501 to access the cartridge 504. The cartridge 504 may be formed to be durable, and the scent modules 505 may be easily removed from the cartridge 504 and replaced. Alternatively, the cartridge 504 may be formed integrally with the scent modules 505, and may be disposed and replaced when the scent modules run out of fragrance.

Although not shown, a lower or side surface of the cartridge case 501 may have an opening or vents at a position that corresponds to a position of the opening 502a of the inner case 502 so that fragrance or scent from an exposed scent module 505 may be dispersed to the vents 146 via the blower 610.

The scents released by the fragrance assembly 500 may be coded into information that is part of a predetermined exercise program such that at certain time intervals, certain scents are released. Content on the display 210 may also be part of the predetermined exercise program, and the fragrance assembly 500 and content on the display 210 may correspond to each other as time progresses.

Figure 27:
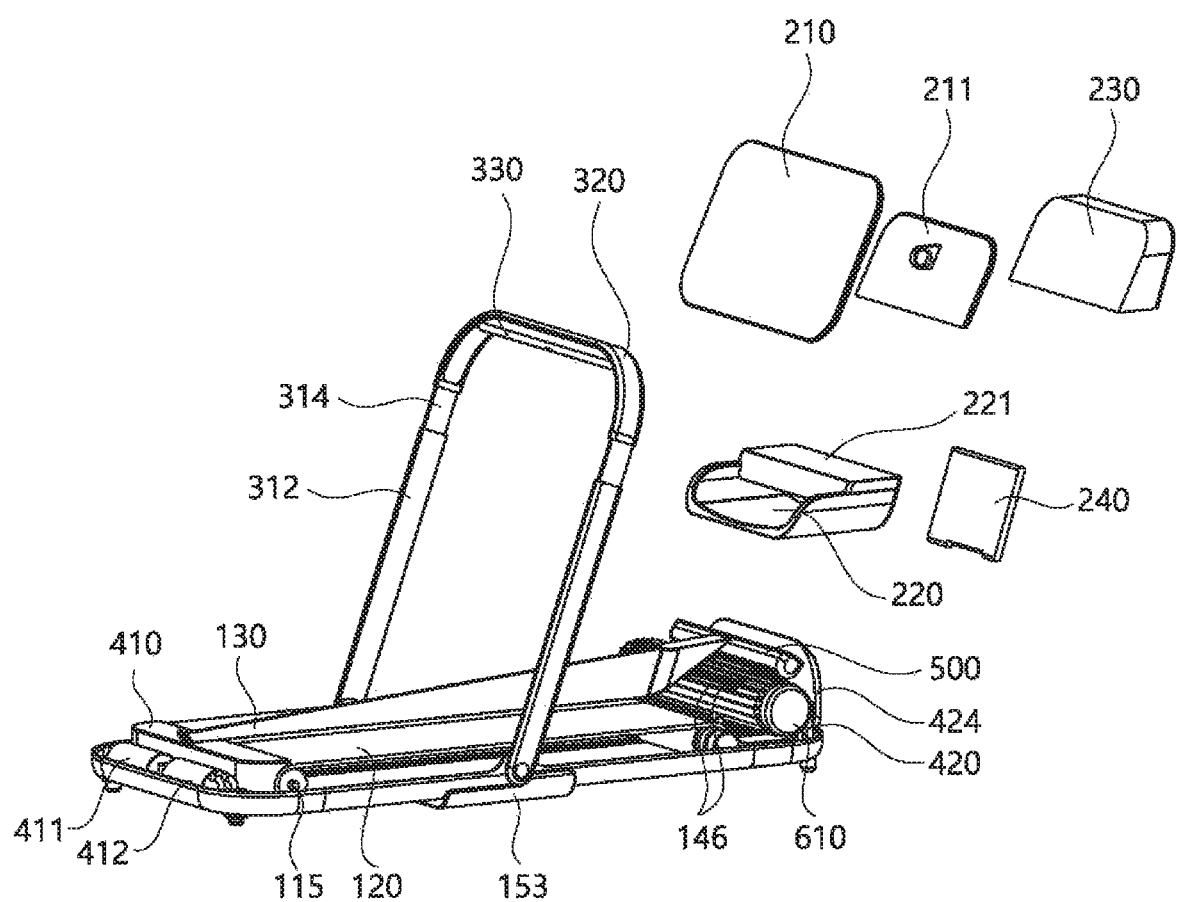
FIG. 27 is a perspective view of a treadmill according to an embodiment showing a detached attachment module.

Referring to FIGS. 6 and 27, the attachment module 200 may include a display 210 to play videos or exercise programs or display a user interface to manually control an operation by the user. The display 210 may include at least one speaker and a camera. Content played on the display 210 may be frequently changed so as to continue to stimulate the pet.

The attachment module 200 may further include a display mount 211, a container 230 to hold food or treats, a lid 231 (FIG. 3) that may be removed to refill the container 230 with treats, and a dispensing tray 220 on which treats from the container 230 may be dispensed. The dispensing tray 220 may include a tray or dispensing container 221 which may couple to the container 230 and support the display mount 211, and an attachment base 240 that couples to the dispensing tray 220 and the tray container 221 to the stand 424 of the second height adjuster 420. The display 210, display mount 211, container 230, dispensing tray 220, tray container 221, and attachment base 240 may be removable, and a user may choose to only attach, as an example the display 210 and the attachment base 240.

Figure 8:
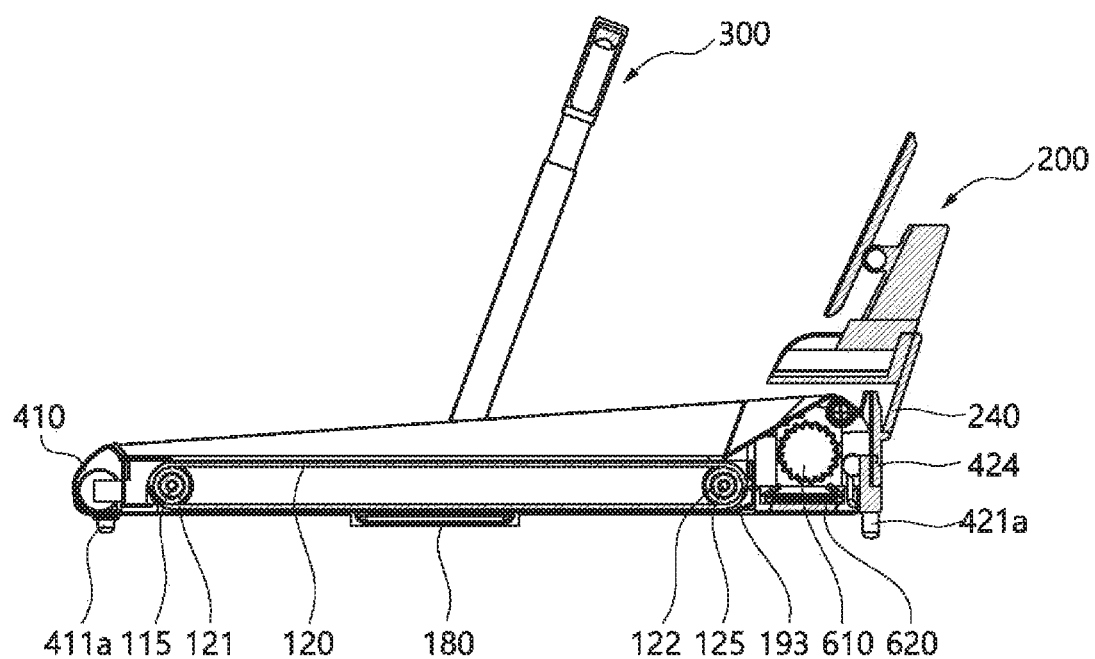
FIG. 8 is a cut side view of a treadmill showing an inside of the base.
Figure 9:
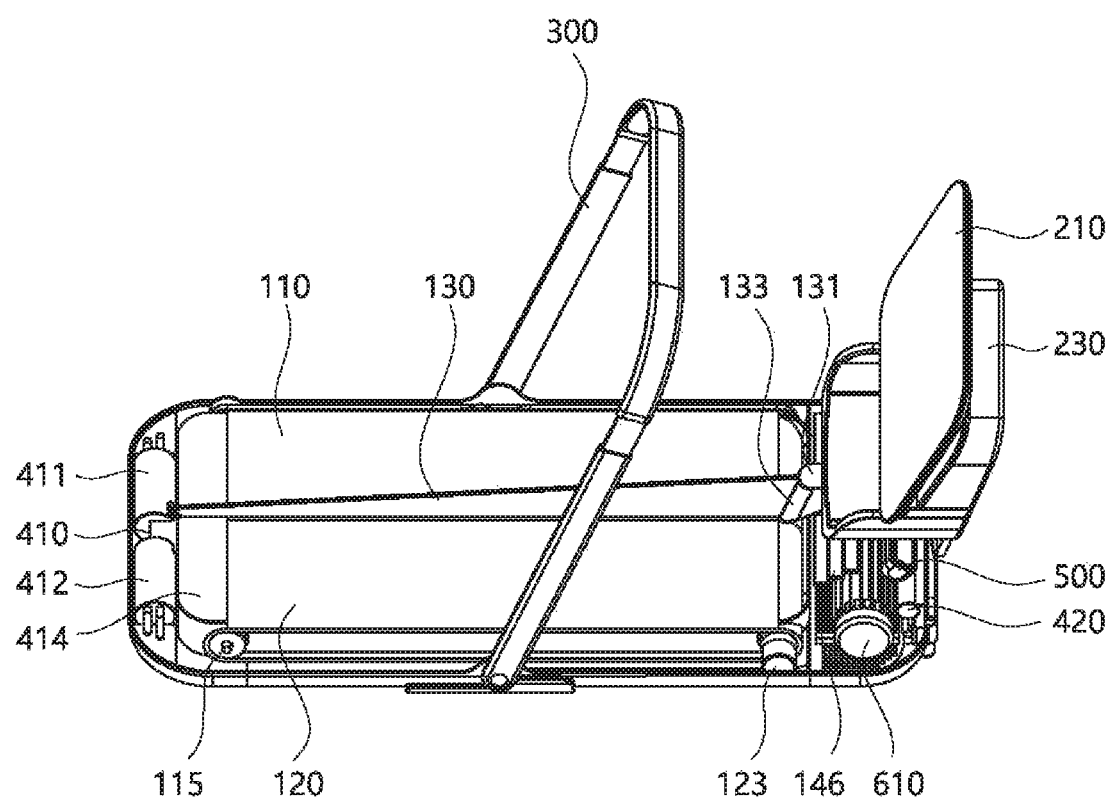
FIG. 9 is perspective side view of the treadmill of FIG. 8.

Referring to FIGS. 6, 8, 27, and 28A, the attachment base 240 may be a plate having a rectangular or square shape. A lower side or portion of the attachment base 240 may be coupled to an upper side or portion of the stand 424. As shown in FIG. 8, the lower side of a back surface of the attachment base 240 may have a protrusion which may be inserted into a recess or groove provided in an upper side of a front surface of the stand 424. The recess or groove of the stand 424 may have a recessed cylindrical shape corresponding to a cylindrical shape of the protrusion of the attachment base 240. The protrusion of the attachment base 240 may be pressed-fit into the recess of the stand 424 to be removable so that the entire attachment assembly 200 may be removed from the treadmill 1.

The tray container 221 may have an upper hole or opening that communicates with a bottom hole or opening of the container 230. The tray container 221 may also have a lower hole or opening so that treats stored in the container 230 may fall through the bottom hole of the container 230, the upper hole of the tray container 221, and the lower hole of the tray container 221 onto the dispensing tray 220. At least one of upper and lower holes of the tray container 221 and or the bottom hole of the container 230 may have a gate that is automatically driven to selectively open and close. The gate may open when it is time to dispense a treat (e.g., during a luring process or during a rewards process), and may close to prevent treats from falling onto the dispensing tray 220 (e.g., during an exercise process or in a storage state).

The container 230 may be a hollow container formed of front and back walls, side walls, an upper wall and lid 231, and an optional bottom wall having an opening. The side walls and front and back walls may be pressed fit onto grooves provided on an upper surface of the tray container 221. The container 230 may be easily removable from the tray container 221 so that a user may clean or refill treats stored in the container 230. The lid 231 (FIG. 3) provided on a top of the container 230 may allow a user to quickly refill the container 230, or alternatively may be a handle that allows a user to remove the container 230 from the tray container 221.

The tray container 221 may be a hollow container formed of front and back walls, side walls, an upper wall, and an optional bottom wall. The tray container 221 may be formed separately from the dispensing tray 220 and later combined, or the tray container 221 and the dispensing tray 220 may be formed together (e.g., injection molded) as a single element. The tray container 221 and the dispensing tray 220 may be made of plastic or, alternatively, metal.

A bottom end of the display mount 211 may be provided on and supported by the upper wall of the tray container 221. The display mount 211 may be a plate having, for example, a rectangular or square shape. The front wall of the container 230 may be inclined backward from a lower end to an upper end. A back surface of the display mount 211 may have a shape and inclination corresponding to a shape and inclination of the front wall of the container 230 and may be provided on the front wall of the container 230. A size of the display mount 211 may be equal to or smaller than a size of the front wall of the container 230. Alternatively, the display mount 211 may be larger than the front wall of the container 230 and/or protrude above the front wall of the container 220.

The display mount 211 may be removably coupled to the container 230. For example, the display mount 211 may be coupled magnetically to the container 230. Alternatively, the container 230 may have rail guides, and a back of the display mount 211 may have rails that slide into the rail guides.

The display mount 211 may have at least one protrusion protruding outward from a front surface and having at least one opening or hole in which a support shaft or protrusion 210a of the display 210 may be inserted. The display 210 may be hingedly coupled to the display mount 211 via the hole 211a and the protrusion 210a.

Figure 28A:
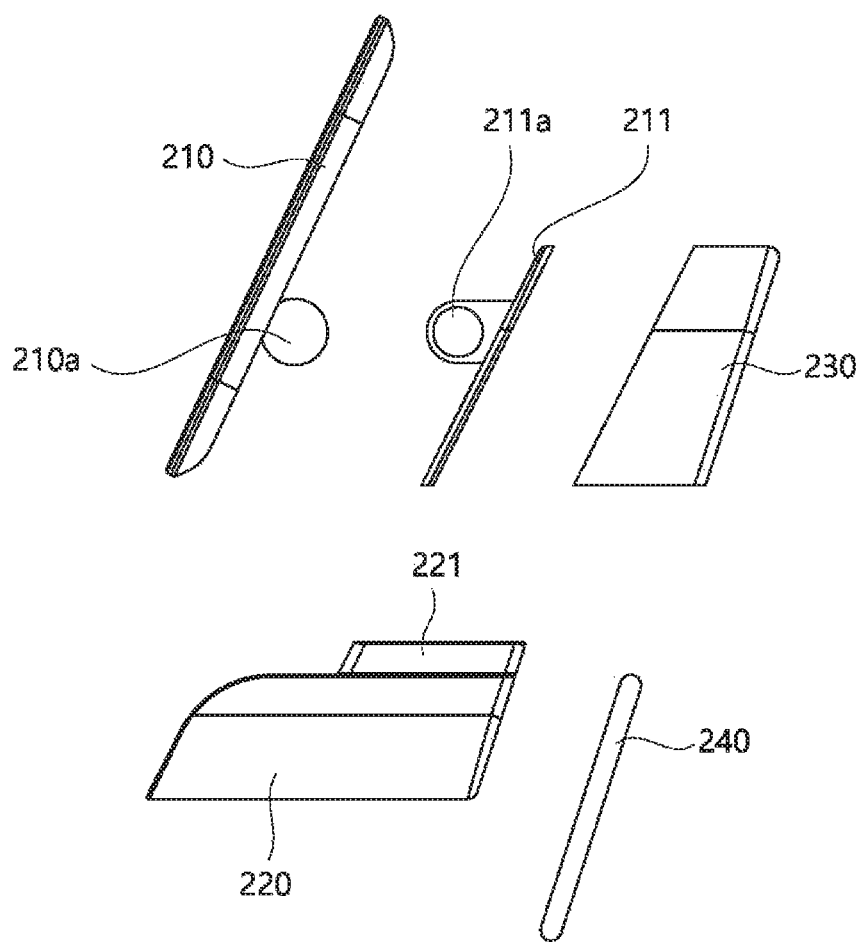
FIG. 28A shows a side exploded view of the attachment assembly of FIG. 27.
Figure 28B:
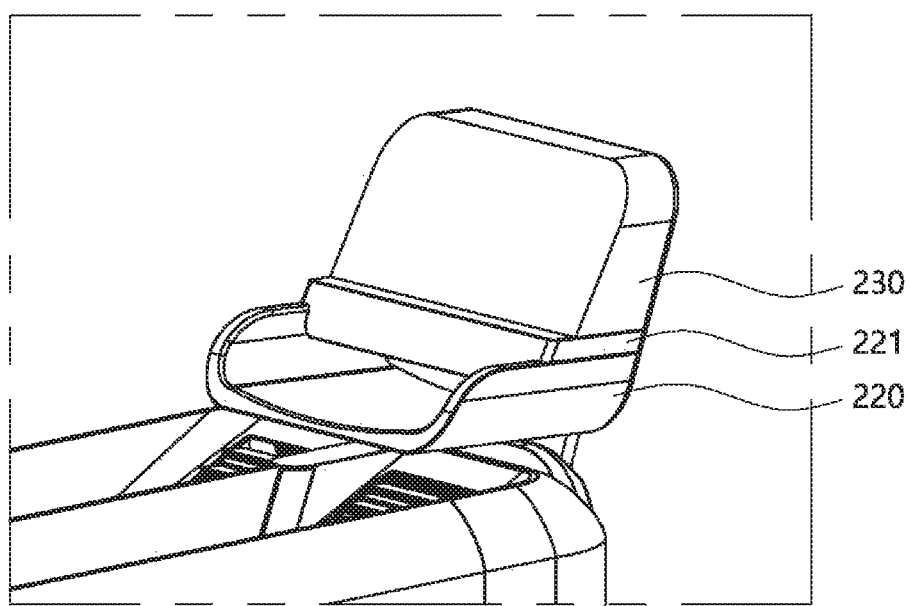
FIG. 28B and FIG. 28C shows perspective front views of possible arrangements of the attachment assembly.
Figure 28C:
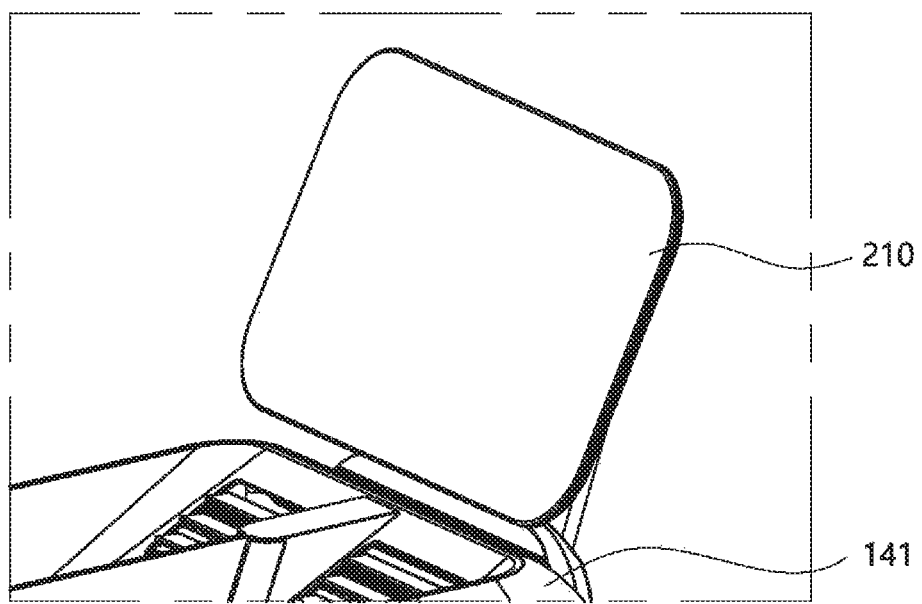

Referring to FIGS. 28A-28C, at least one of the display 210, the container 230, the tray container 221, and the dispensing tray 220 may be optional, and a user may customize the attachment module 200. When the dispensing tray 220, tray container 221, and the container 230 are omitted, the display 210 may be coupled directly to the stand 424. In such a case, the display 210 may have a fixed inclination or orientation. A back surface of the display 210 may be configured to couple to a front surface of the stand 424 via, e.g., a groove in the front surface of the stand 240 and a corresponding protrusion on a back surface of the display 210.

FIG. 28B exemplifies an attachment module 200 where the display 210 and the display mount 211 are omitted. FIG. 28C exemplifies an attachment module 200 where the dispensing tray 220, tray container 221, container 230, and display mount 211 are omitted.

Referring back to FIG. 28A, the protrusion 210a may rotate within the hole 211a so that an inclination of the display 210 may be adjusted. There may be a motor provided in the protrusion 210a so that an inclination of the display 210 may be automatically adjusted. The inclination of the display 210 may be automatically adjusted based on a height of the pet sensed by the handle sensor 331 provided in the handle 330, a position of the pet sensed by left and right proximity sensors 132 and 133 provided in the divider 130 described later, and/or an image captured by the camera of the display 210. The display 210 may be inclined away from a pet on the treadmill 1 from a bottom end to a top end such that an angle between the front of the display 210 and a horizontal axis is obtuse.

The display 210 may be a liquid crystal display (LCD) backlit by light emitting diodes (LEDs) or organic light emitting diodes (OLEDs). The display 210 may have a communication and/or WiFi or BlueTooth module so that videos (e.g., DogTV videos) may be streamed on the display 210 and/or a remote owner may communicate with a pet on the treadmill 1 via, e.g., FaceTime or Skype, or via a mobile/web application executed by the remote user (i.e., a pet owner). Applications typically requiring input by callers to accept or place a call (as with FaceTime or Skype) may be modified to be controlled by the pet owner and/or be implemented in a mode that automatically accepts calls. Videos streamed on the display 210 may be also designed for pets, and may show certain shades of colors (e.g., yellow, blue, gray, and/or green) for dogs. The videos played on the display 210 may have a relatively high refresh rate or flicker frequency (e.g., at least 100 Hz) so that a pet may perceive the images as continuous. The display 210 may also emit sounds at a relatively high frequency (e.g., 47,000-75,000 Hz) to stimulate the pet.

The display 210 may further include a camera or webcam so that the owner may see the pet, and/or images from the handle sensor 331 may be accessed online or via a mobile application. The display 210 may also be configured to play pre-recorded exercise programs, which may be programmed in conjunction with the fragrance assembly 500, the blower 610, and/or the back and front height adjusters 410 and 420. The display 210 may have a printed circuit board that electrically connects to the control module 640. The display 210 and/or the control module 640 may include a memory or storage to store exercise data about how often, how long, and how far a pet has exercised.

Figure 29:
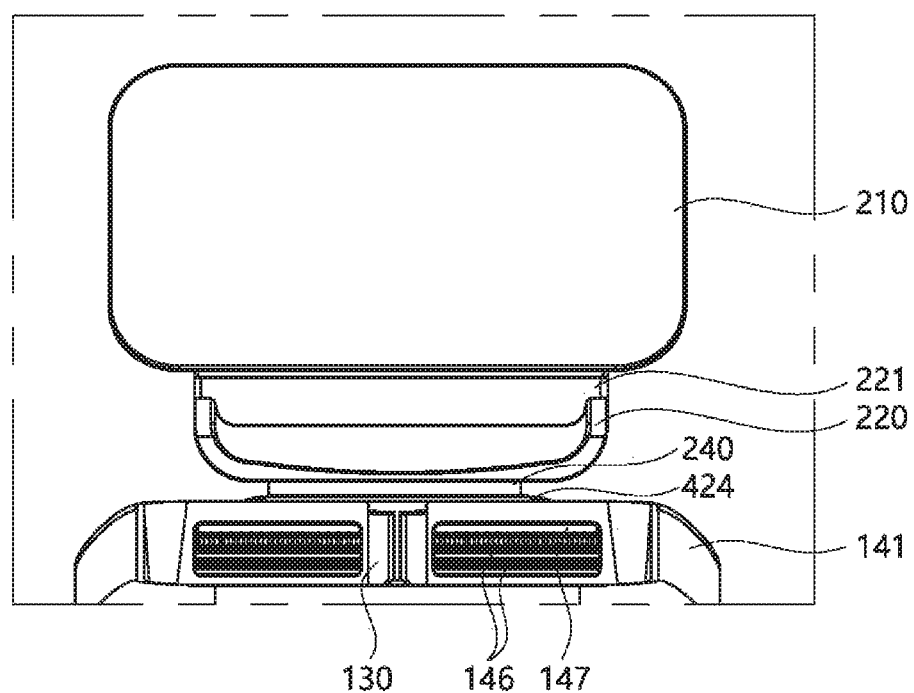
FIG. 29 shows a front view of an attachment module according to an embodiment.
Figure 30:
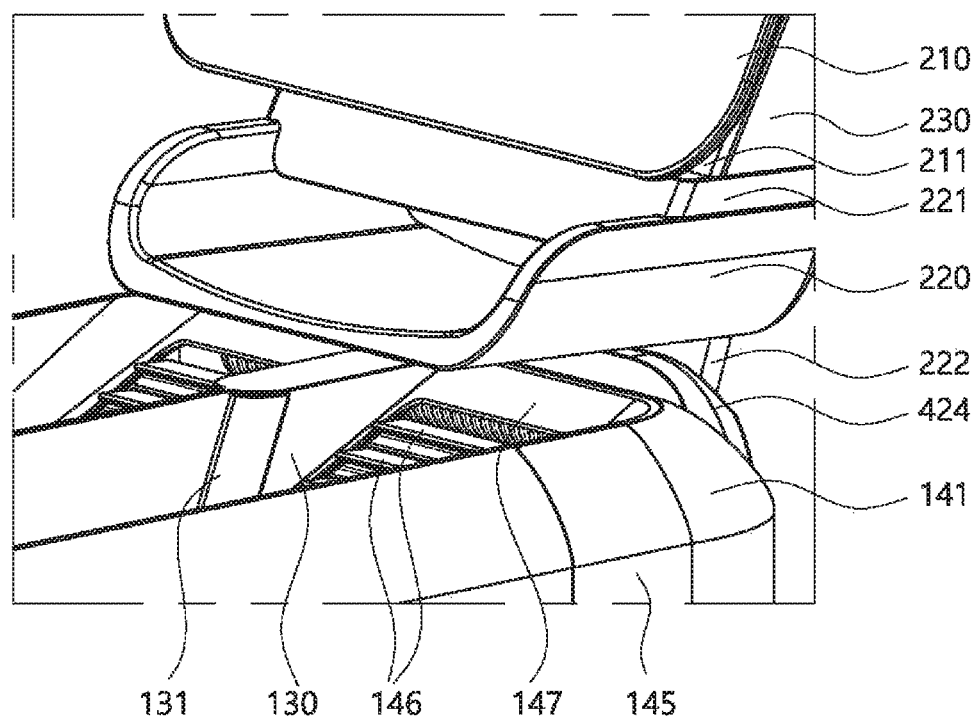
FIG. 30 shows a perspective front view of the attachment module of FIG. 29.

Referring to FIGS. 29-30, the dispensing tray 220 may provide a surface on which treats stored in the container 230 may be dropped. The dispensing tray 220 may have curved sidewalls so as to prevent treats from being dropped off the sides of the dispensing tray 220. Treats may remain on the dispensing tray 220, or alternatively a curvature and inclination of the dispensing tray 220 may be configured to guide treats onto the left and right belts 110 and/or 120. When a treat is dispensed onto the dispensing tray 220, the vents 146 may be automatically closed, and the left and right belts 110 and/or 120 may be slowed down or stopped (i.e., the motors 123 and 113 may slow down or stop a rotation of the front right and back left rollers 122 and 111) so that a pet may safely consume the treat.

The vents 146 may include provided in the opening 147 of the front frame 141. A section of the front frame 141 including the opening 147 and vents 146 may be an inclined surface having an inclination that is equal or similar to an inclination of a lower surface of the front portion of the divider 130. The front end of the divider 130 may be coupled to the inclined surface of the front frame 141 between left and right sets of vents 146.

The vents 146 may be vanes that are adjustable automatically via a motor provided at ends of the vents 146. When the treadmill 1 is in a storage mode, the vents 146 may be adjusted to be closed. A degree of opening of the vents 146 may be adjusted to correspond to an exercise program played on the display 210 (e.g., a windy program) or based on a predicted exertion, exhaustion, or temperature of the pet. There may further be an optional temperature sensor provided in the front frame 141 or in the divider 130. In addition, the handle sensor 331 may have an infrared sensor (e.g., passive infrared sensor or PIR) to sense a temperature and/or movement of the pet. When a certain temperature or temperature increase is sensed by the temperature sensor, the vents 146 may be opened to a degree corresponding to a degree of the temperature increase, and/or the Peltier device 633 may be operated to provide cool air.

A degree of opening of the vents 146 may also be controlled to control a strength of scents emitted by the fragrance assembly 500. For example, the vents 146 may be opened to a maximum degree so that a pet is exposed to a maximum scent strength. The vents 146 may be closed to prevent or minimize the scent strength. The vents 146 may be automatically closed when the fragrance assembly 500 is switching between different scents or smells. Alternatively or in addition thereto, a scent strength may be increased by increasing speed of the blower 610 and/or by increasing a temperature of the air around the fragrance assembly 500 via the Peltier device 633 to facilitate a vaporizing of the scent modules 505.

If the main controller of the control module 640 determines, via positions sensed by the left and right proximity sensors 132 and 133, that a pet is outside of a predetermined lateral distance range, the control module 640 may communicate with various circuitry on the PCBs of the back and front height adjusters 410 and 420 so that an inclination of the treadmill 1 may be adjusted to scoot or encourage the pet to move back into the predetermined lateral distance range. For example, if the control module 640 determines that a pet is too far to the left and outside of the predetermined lateral distance range, the left front and back legs 421a and 411a may be lengthened so that the treadmill 1 is inclined downward in a left-right direction. The pet may fall or be guided toward the right. When it is determined that the pet is within the predetermined lateral distance range, the left front and back legs 421a and 411a may be shortened back to an initial position, and/or pre-programmed inclinations according to an exercise program may be continued.

In addition to or separate from the inclination control method described above, the control module 640 may also calculate a gait when a pet is too far to the left or too far to the right. If the control module 640 determines that a pet is too far to the left and outside of the predetermined lateral distance range, the control module 640 may determine that a stride length of the pet's right leg is greater than a stride length of the pet's left leg. The control module 640 may control the right motor 123 to increase a speed of the right belt 120 and/or may control the left motor 113 to decrease a speed of the left belt 110.

A speed sensor may be provided in at least one of the motors 123 and/or 113, or alternatively on the lower frame 150 near one of the rollers 111, 112, 121, 122 to sense a linear speed of the left and/or right belts 110 and 120. Alternatively or in addition thereto, the control module 640 may determine a speed of the left and right belts 110 and 120 based on an operation of the left and right motors 113 and 123. A memory or storage provided in the control module 640 may record information on how fast or how far a pet has traveled during exercise.

Figure 31:
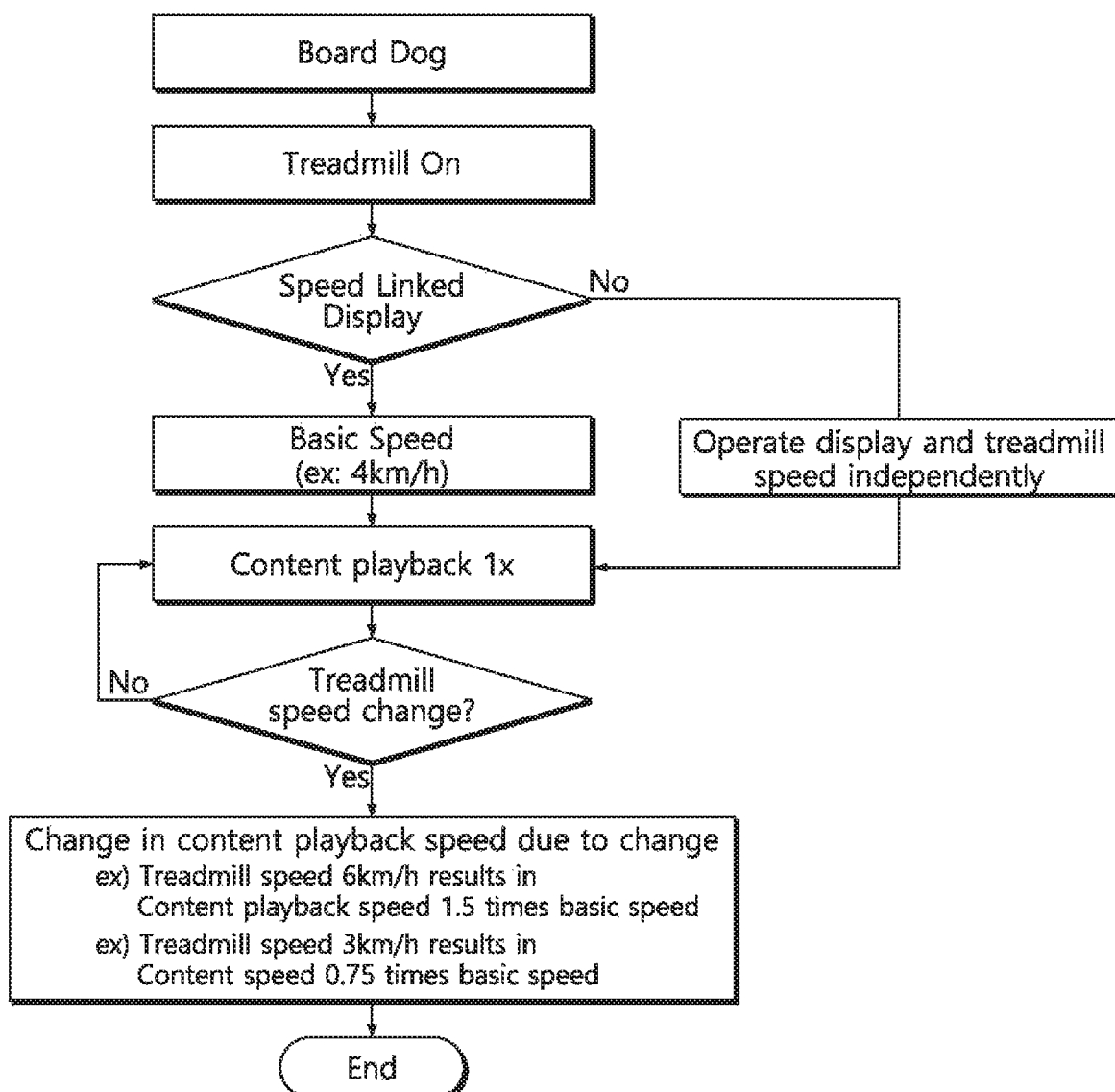
FIG. 31 shows a process where a video on the display plays according to a speed of the treadmill according to an embodiment.

Referring to FIG. 31, a user may select a "speed link" option so that exercise programs or other content played on the display 210 correspond to a speed of the left and right belts 110 and 120 of the treadmill 1. A basic or initial speed of the left and right belts 110 and 120 may be set to be at or around a natural walking speed (e.g., 4 km/h or roughly 2.5 mph). When the left and right belts 110 and 120 are moving at different speeds to accommodate gait, the "basic speed" of the left and right belts 110 and 120 may be defined as an average speed of the left and right belts 110 and 120.

If the "speed link" option is not selected, then the display 210 may display content (e.g., a family picture, a calming image, DOG TV, or other sound, image, or video) regardless of (or independent from) a speed of the left and right belts 110 and 120. If the "speed link" option is selected, however, the content will play at a normal or regular speed when the left and right belts 110 and 120 are travelling at the basic speed. The normal or regular speed of the content played on the display 210 may simulate or represent the basic speed. If the main controller in the control module 640 determines a change in the average speed of the left and right belts 110 and 120, then the main controller may operate the display 210 to proportionately change a speed of the displayed content.

For example, if it is sensed or determined that the average speed of the left and right belts 110 and 120 has increased from a basic speed of 4 km/h to 6 km/h (roughly 3.7 mph) (for example, due to a speed adjustment based on positions sensed by the handle sensor 331 and/or the proximity sensors 132 and 133), then the content on the display 210 may be played at 1.5 times the normal or regular speed. If it is sensed or determined that the average speed of the left and right belts 110 and 120 has decreased from a basic speed of 4 km/h to 3 km/h (roughly 1.9 mph), then the content on the display 210 may be played at 0.75 times the normal or regular speed.

Figure 32:
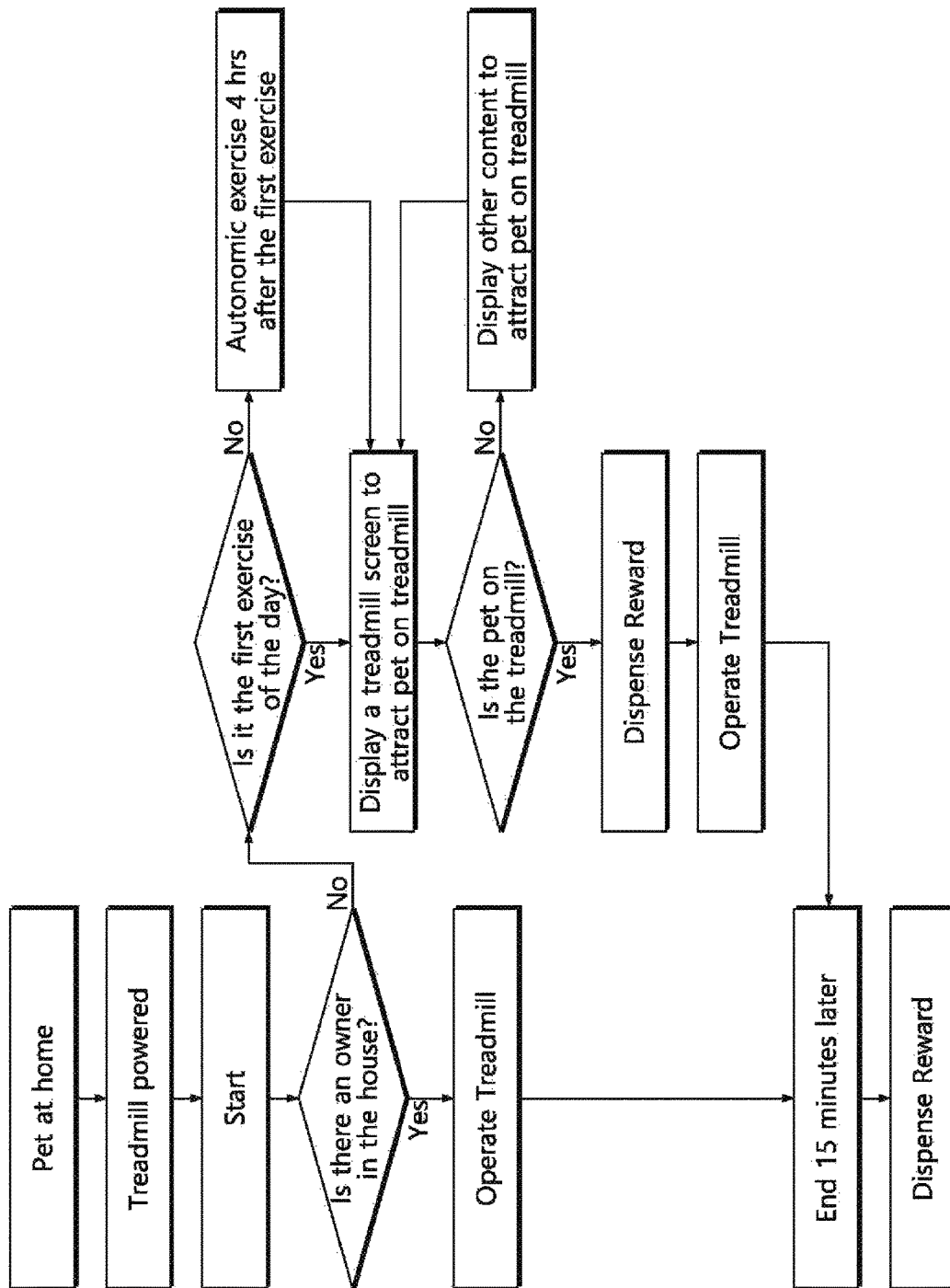
FIG. 32 shows a process of luring a pet to a treadmill for autonomous exercise according to an embodiment.

Referring to FIG. 32, the treadmill 1 may operate differently when an owner is away from the home versus when the owner is in the home. The communication module in the control module 640 of the treadmill 1 may interact with a mobile application or GPS data from a user's cell phone to determine whether the owner is home. When an owner is home, an operation of the treadmill 1 may be initiated by the owner, an operation may end 15 minutes later, and a treat may be dispensed on the dispensing tray 220. Alternatively, when the owner is home, the attachment module 200 may not dispense a treat or reward at the end of the exercise, and the owner may determine whether or not to give his pet a treat.

When the main controller of the control module 640 determines that the owner is not home, the treadmill 1 may initiate a luring or attraction process until the pet has exercised a predetermined number of times (e.g., four times or two times) during a predetermined time period (e.g., a day or an eight hour period). The control module 640 may have a timer or clock and a memory or storage, and may collect data on how often the treadmill 1 is used. The communication module of the control module 640 may also interact with a pet pendant or pet tag attached to a particular pet, so when multiple pets live in a single household, the control module 640 may be able to collect data on how often a particular pet has used the pet treadmill 1.

When the owner is not home, the main controller of the control module 640 may first determine whether the treadmill 1 has been used that day (or alternatively, whether a particular pet has exercised yet that day). When it is determined that the treadmill 1 has not yet been used, the display 210 may be controlled to display content that may be pleasing for pets to lure the pet to the treadmill 1. For example, the display 210 may show images of other pets, play sounds of other animals, or stream programs from programs designed for pets (e.g., DogTV). The fragrance assembly 500 may emit a scent or fragrance (e.g., flower scent or an optional meat or food scent) from one of the scent modules 505 to spark curiosity in the pet.

If, in a predetermined time period, the main controller determines that a pet is present on the treadmill 1 via sensed measurements from at least one of the handle sensor 331, a proximity sensor 132 or 133 in the divider 130, or optional weight sensors in the lower frame 150, the gate in the attachment module 200 may be controlled to be open so that a treat is dispensed from the container 230 to the dispensing tray 220 to reward the pet for boarding. The left and right belts 110 and 120 may be turned very soon after dispensing (e.g., half a second or less) to keep the pet's attention and to prevent the pet from jumping off the treadmill 1 before an exercise program is started. Once the pet has started an exercise program, operation of the treadmill 1 may end a predetermined program time (e.g., 15 minutes) later, and a reward or treat may be dispensed.

Alternatively or in addition thereto, a treat may be dispensed after a pet has exercised for a certain amount of time (e.g., 5 minutes) or exercised a predetermined distance (e.g., 0.3 miles). When a treat is dispensed before an exercise program has ended, speeds of the left and right belts 110 and 120 may be slowed down or stopped so that the pet is not injured during consumption of the reward.

If, in a predetermined time period, the main controller determines (via the handle sensor 331, the proximity sensor in the divider 130, or optional weight sensors in the lower frame 150) that a pet has not boarded the treadmill 1, the display 210 may play different content to attract the pet including sound and video of the owner, which may have been pre-recorded and stored in the memory or may be lived streamed from the owner using the mobile/web application upon notification of a failed luring attempt to the owner. The attachment module 200 may also dispense a preliminary treat to lure the pet onto the pet treadmill 1. In such a situation, once it is determined that the pet has boarded the treadmill 1, the left and right belts 110 and 120 may be immediately rotated after the determination without regard for whether the pet is centered or properly positioned on the left and right belts 110 and 120 to prevent the pet from jumping off the treadmill 1 after consuming the treat but before exercising.

If the pet is not lured to the treadmill 1 after a second predetermined time period, an operation of the treadmill 1 may be stopped, and a luring process may be restarted after a predetermined reattempt time (e.g., after 15 minutes, an hour, etc.) If the pet was lured to the treadmill 1 and finished an exercise program, the luring process may be restarted after a predetermined rest time (e.g., after four hours) to encourage the pet to use the treadmill 1 again later in the day. A memory in the main controller may store information on how often the luring process was initiated and how often and when the pet exercised, and an owner may access that information via the display 210 or a mobile application.

Figure 33:
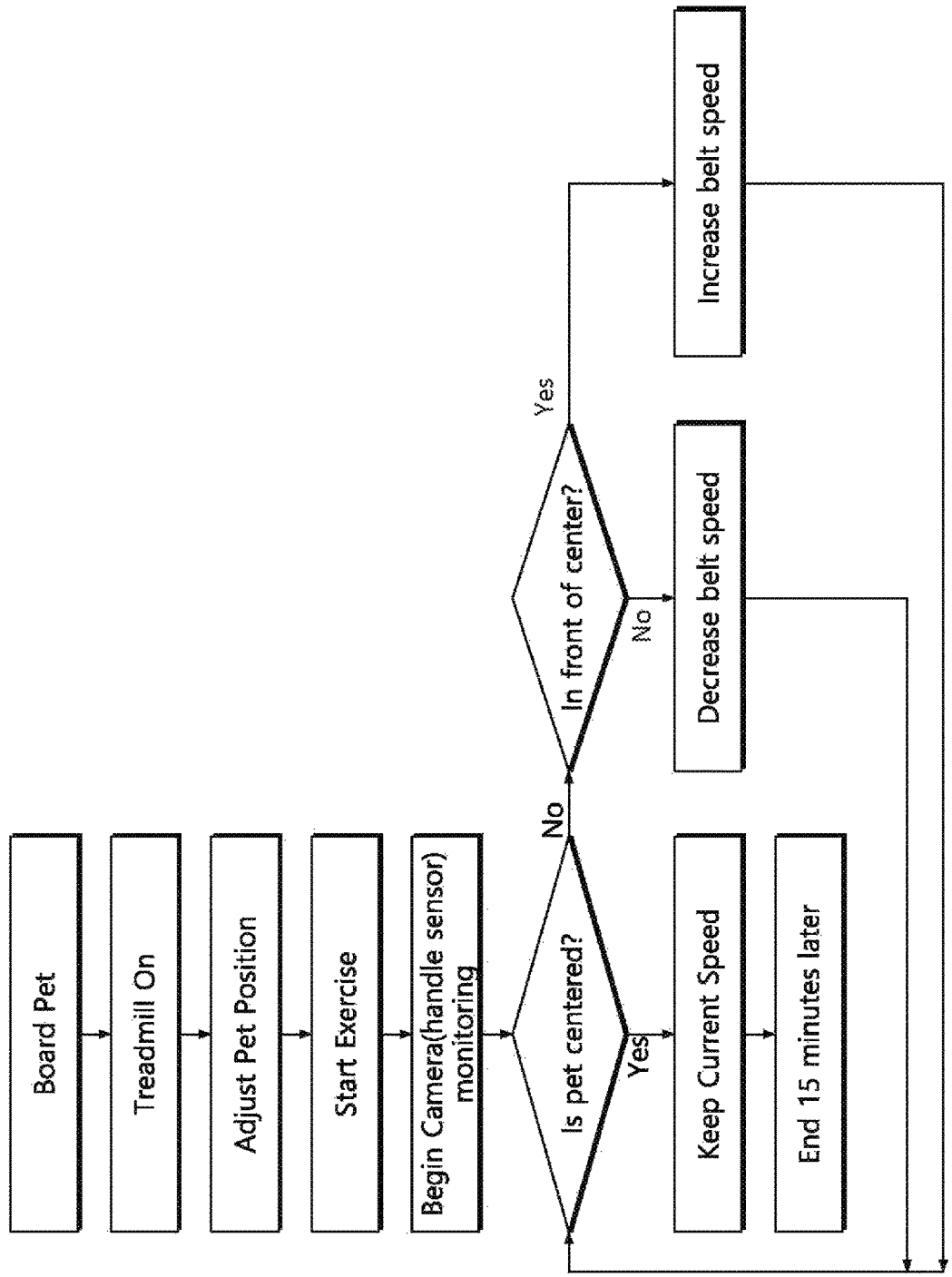
FIG. 33 shows a process of adjusting a speed of the treadmill based on a position of the pet on the treadmill according to an embodiment.

Referring to FIG. 33, speeds of the left and right belts 110 and 120 may be adjusted based on a forward-backward position sensed by the handle sensor 331. Such adjustments may override any predetermined speeds of the left and right belts 110 and 120 as part of a predetermined exercise program. If it is determined by the main controller in the control module 640 that the pet is properly positioned and/or centered based on a sensed position by the handle sensor 331, then the speeds of the left and right belts 110 and 120 may be maintained. However, if the main controller determines that the pet is in front of a predetermined position or a predetermined position range, speeds of the left and right belts 110 and 120 may be increased by equal amounts. If the main controller determines that the pet is not centered and behind the predetermined position range (or alternatively, behind a second predetermined position), speeds of the left and right belts 110 and 120 may be decreased by equal amounts. A memory in the main controller may store information on the left and right belt speeds 110 and 120 and how fast the pet exercised during an exercise program or session, and the owner may access that information via the display 210 or a mobile application.

Alternatively or in addition thereto to the method of increasing or decreasing speeds shown in FIG. 33, a forward-backward inclination of the treadmill 1 may be adjusted via the front and back height adjusters 420 and 430 based on a forward-backward position sensed by the handle sensor 331. If it is determined by the main controller in the control module 640 that the pet is properly positioned and/or centered based on a sensed position by the handle sensor 331, then the inclination of the treadmill 1 may be maintained.

However, if the main controller determines that the pet is in front of a predetermined position or a predetermined position range, lengths of the front left and right legs 421a and 422a may be increased by equal amounts and/or lengths of the back left and right legs 411a and 412a may be decreased by equal amounts. If the main controller determines that the pet is not centered and behind the predetermined position range (or alternatively, behind a second predetermined position), lengths of the front left and right legs 421a and 422a may be decreased by equal amounts and/or lengths of the back left and right legs 411a and 412a may be increased by equal amounts. A memory in the main controller may store information on how often the inclination of the treadmill 1 changes and to what degree, and the owner may access that information via the display 210 or a mobile application.

Figure 34:
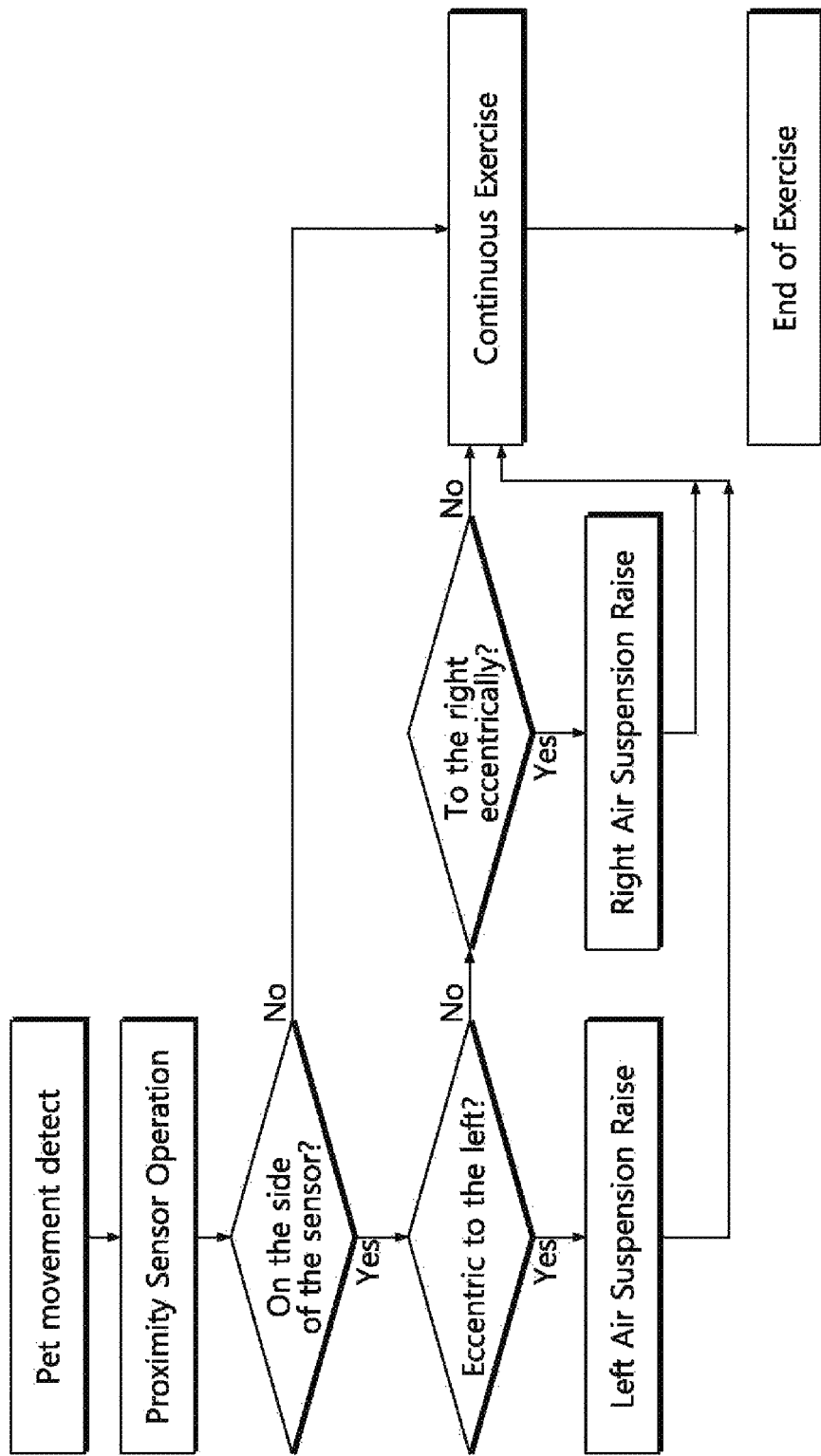
FIG. 34 shows a process of adjusting an inclination of the treadmill based on a position of the pet on the treadmill according to an embodiment.

Referring to FIG. 34, an inclination of the treadmill 1 may be adjusted based on a left-right position of the pet sensed by proximity sensors in the divider 130 by adjusting lengths of the legs 411a, 412a, 421a, and 422a. Such an adjustment may override any predetermined inclinations of the treadmill 1 as part of an exercise program. The left proximity sensor 132 may measure how far to the left a pet may be positioned, and the right proximity sensor 133 may measure how far to the right a pet may be positioned.

If the main controller of the control module 640 determines, based on positions sensed by the left and right proximity sensors 132 and 133 in the divider 130, that the pet is beyond a predetermined lateral distance or distance range from the divider 130, the main controller may further determine whether the pet is too far to the left or too far to the right. If it is determined that the pet is too far to the left, then lengths of the left front and back legs 421a and 411a may be increased and/or lengths of the right front and back legs 422a and 412a may be decreased via an air suspension process controlled in the front and back height adjusters 420 and 410. If it is determined that the pet is too far to the right, then lengths of the right front and back legs 422a and 412a may be increased and/or lengths of the left front and back legs 421a and 411a may be decreased via an air suspension process controlled in the front and back height adjusters 420 and 410. If it is determined that the pet is within the predetermined lateral distance, then continuous exercise may be implemented and an inclination of the treadmill 1 may not be altered in response to a pet position.

Alternatively or in addition thereto to the method of changing left/right inclinations, the left-right position of the pet may indicate a gait, and speeds of the left and right belts 110 and 120 may be changed in response to positions sensed by the proximity sensors 132 and 133. If it is determined that the pet is too far to the left, then a speed of the left belt 110 may be decreased via the left motor 113 and/or a speed of the right belt may be increased via the right motor 123. If it is determined that the pet is too far to the right, then a speed of the left belt 110 may be increased via the left motor 113 and/or a speed of the right belt may be decreased via the right motor 123. If it is determined that the pet is within the predetermined lateral distance, then continuous exercise may be implemented and an inclination of the treadmill 1 may not be altered in response to a pet position.

Figure 35:
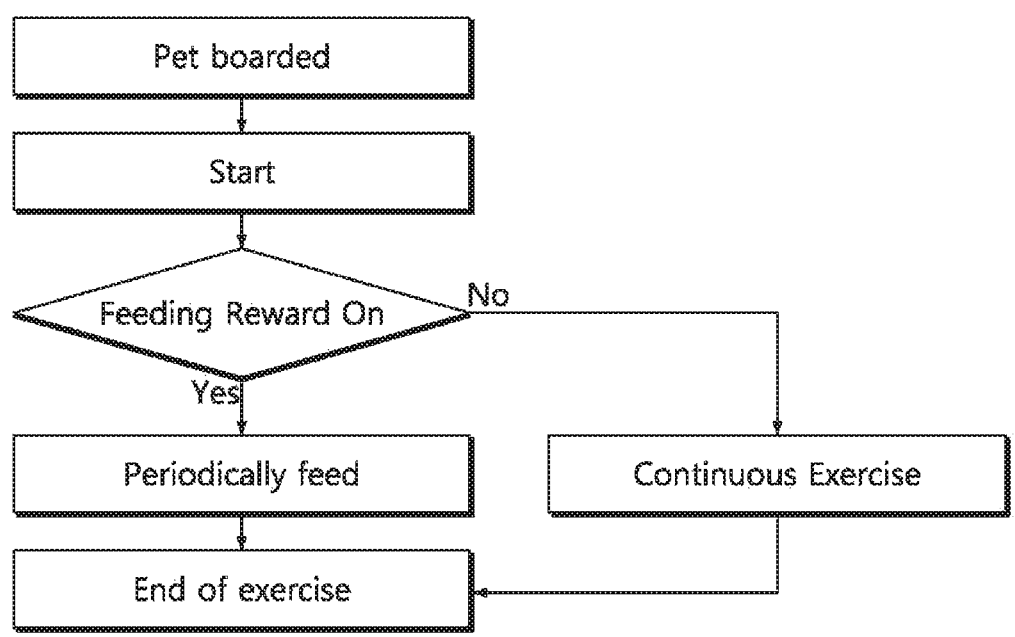
FIG. 35 shows a process of feeding a pet on the treadmill according to an embodiment.

Referring to FIG. 35, a user may control whether the attachment module 200 will dispense treats during an exercise program or process of the pet. If the user selects a rewards process to be off, then continuous exercise may be implemented without treats being dispensed by the attachment module 200. If the user selects the rewards process to be on, then the attachment module 200 may periodically dispense treats in the middle of an exercise program based on distance traveled or time. When the attachment module 200 dispenses a treat, the left and right belts 110 and 120 may be controlled to be slowed down or stopped, which may temporarily disrupt the exercise program. The memory of the control module 640 may store information on how often and how many treats are dispensed from the container 230 onto the dispensing tray 220, and the user may access that information via the display 210 or a mobile application.

Figure 36:
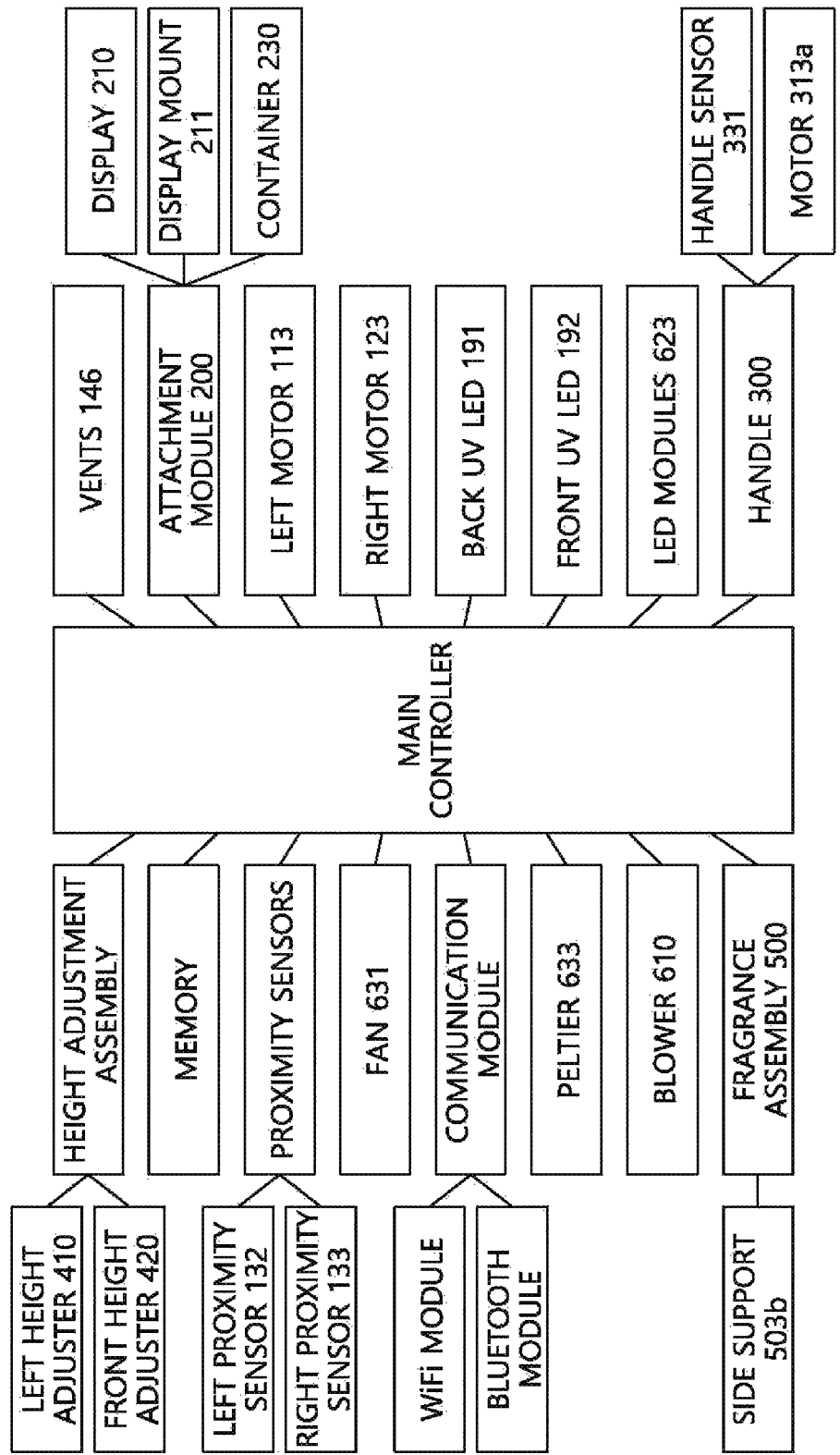
FIG. 36 is a block diagram of a main controller provided in a control module.

Referring to FIG. 36, the main controller of the control module 640 may electrically connect to a communication module provided in the control module 640. The communication module may communicate with communication modules of various sub-PCBs provided in the treadmill 1 (e.g., in the front and back height adjusters 410 and 420, in the display 210, in the handle 300, etc.), and may also include a WiFi module and a Bluetooth module.

The main controller may control, either directly or interacting with other communication modules, operations of the back and front LEDs 191 and 192, the back and front height adjusters 410 and 420, the vents 146, the left and right proximity sensors 132 and 133, and the left and right motors 113 and 123. The main controller may further control an operation of the motor 313a and handle sensor 331 in the handle 300 and the motor in the side support 503b of the fragrance assembly 500. With respect to the attachment module 200, the main controller may control an operation of the display 210, an inclination of the display 210 via the display mount 211, and a dispensing of treats via the gate in the container 230. The main controller may control an operation of the blower 610, the fans 632, the Peltier device 633, and the LED modules 623 that activate the photocatalytic deodorizer 622.

The main controller may make determinations and control operations of the various electronic devices based on sensed measurements by the handle sensor 331, and the left and right proximity sensors 132 and 133. Sensed measurements may be recorded and stored in the memory, and the main controller may make future determinations based on data stored in the memory. A user may access data stored in the memory via the display 210 or on a mobile application installed on a mobile device that communicates with the communication module.

Figure 37A:
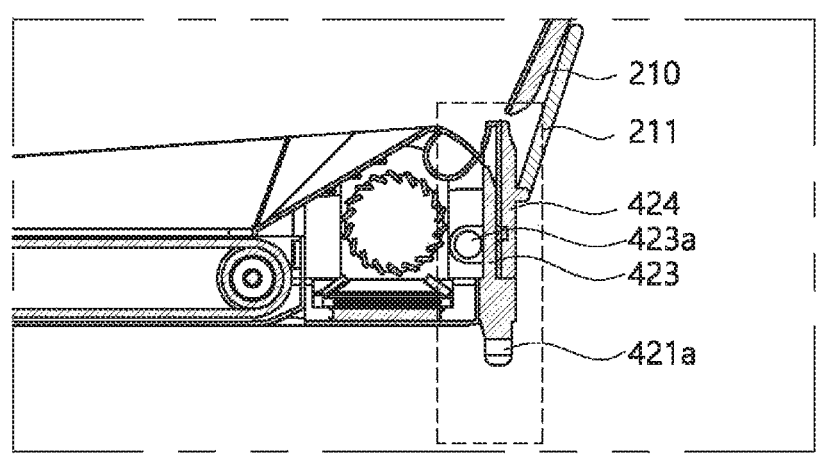
FIGS. 37A and 37B show an alternative embodiment of height adjustment process.
Figure 37B:
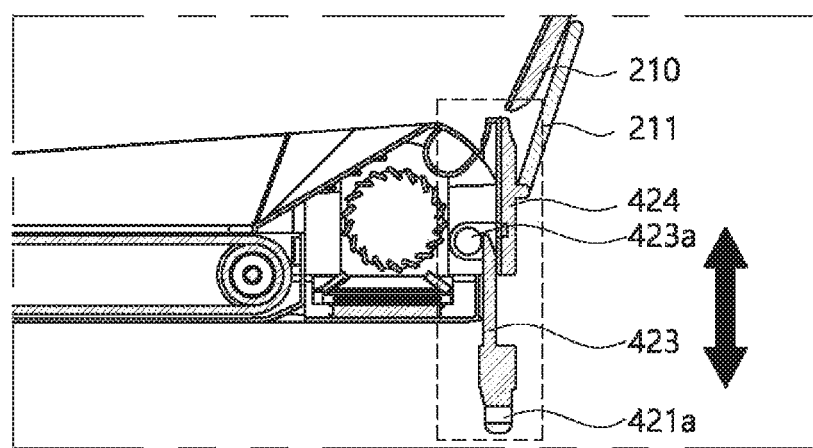

Referring to FIGS. 37A and 37B, the front and back height adjusters 410 and 420 may alternatively operate via a gear method instead of air suspension. FIGS. 37A and 37B show a gear method for the front height adjuster 420, but a similar method may be applied to the back height adjuster 410. The front frame 141 of the upper frame 140 and the front end of the lower frame 150 may be fixed to the stand 424, which may be slideably coupled to the front support 423. The front support 423 may be provided in a pair to correspond to left and right front legs 421a and 422a, or may have a slit in a center. A gear 423a may have a support or center frame 423b that is fixed to the stand 424. The support 423b of the gear 423a may extend between the pair of front supports 423 or alternatively be inserted through the slit of the center of the front support 423. The support 423b of the gear 423a may extend in a longitudinal direction of the treadmill 1, while the gear 423a may protrude laterally from the support 423b (e.g., toward the right or left) to interact with a back surface of the front support 423. When there is a pair of front supports 423, there may be two gears 423a that protrude from the support 423b to the left and right, respectively.

The back surface of the front support 423 may have teeth that interact with teeth of the gear 423a, which may turn manually or via a motor. When the gear 423a turns in a first direction, the front support 423 may be slid downward with respect to the stand 424, and the upper and lower frames 140 and 150 may rise. When the gear 423a turns in a second direction, the front support 423 may be slid upward with respect to the stand 424 and inserted into the treadmill 1 to lower the upper and lower frames 140 and 150.

As another alternative, the back and front height adjuster 410 and 420 may have hydraulic or pneumatic pumps and/or a motor or actuator (e.g., electric, pneumatic, hydraulic) to lift the four legs 411a, 412a, 421a, and 422a and/or the four corners of the treadmill 1. The four legs 411a, 412a, 421a, and 422a, may, for example, have upper and lower pipes that are lengthened via an electric linear actuator.

Although the treadmill 1 is described as being used by an animal or pet, embodiments disclosed herein may also be modified (e.g., made bigger) to be used by humans. For example, people who have injured their legs or who otherwise have gait may not be able to use a standard one-belt treadmill, especially during physical therapy after a recent injury. The treadmill 1 having left and right belts 110 and 120 may be implemented as a human treadmill, and speeds of the left and right belts 110 and 120 may be adjusted to accommodate a human's gait.

Although the figures show a treadmill including two belts, one of ordinary skill in the art would recognize that embodiments disclosed herein may be implemented with one belt that rotates around a single front roller and a single back roller provided at a front and back ends of the treadmill, respectively.

One of ordinary skill in the art should appreciate that, although a treadmill 1 is described, features of the treadmill 1 may be applied to any number of exercise apparatuses. For example, a stair master machine may have separate right and left tracks, an attachment module, and/or a fragrance assembly. The first and second belts 110 and 120 may alternatively be referred to as first and second moveable members, tracks, treads, panels, or stair assemblies.

Although plastic upper and lower frames 140 and 150 are described, alternatively, the upper and lower frames 140 and 150 may be made of metal such as stainless steel to provide a stable, durable base. A treadmill 1 made of metal upper and lower frames 140 and 150 may be advantageous in a dog kennel setting where many different dogs may use the treadmill 1 throughout the day. The upper frame 140 may be bonded or welded to the lower frame 150.

Even when the upper and lower frames 140 and 150 are made of plastic, they may alternatively be bonded or welded together instead of being pressed-fit or snapped-fit to each other. A pressed-fit coupling between the upper and lower frames 140 and 150 may facilitate a removal and replacement of the left and right belts 110 and 120.

As another alternative, the upper frame 140 may be manufactured as a single upper frame 140, or alternatively, the back frame 144, the side frames 145, and the front frame 141 may be manufactured separately and then later pressed-fit or bonded together for integration. The lower frame 150 may similarly be manufactured as a single lower frame 150 or alternatively, the lower frame 150 may include a separate front frame, side frames, and back frame that are pressed-fit or bonded together for integration.

As an alternative to the two rollers 121 and 122 provided at front and back ends of the treadmill 1 as shown in the figures, one of the rollers may be replaced by a fixed shaft or pipe. The shaft may be formed of or coated in a slippery material such that there is not much friction between the belt 120 and the shaft, and the belt 120 may primarily rotate around one roller at a first end and pass over the slippery end of the shaft at the second end.

There may be an optional guide or tab provided on the upper frame 140, lower frame 150, and/or on side surfaces of the rollers 111, 112, 121, and 122 to keep the left and right belts 110 and 120 in place and aligned on the rollers 111, 112, 121, and 122.

With respect to FIGS. 7A-7C, the front and back roller frames 142*b* and 142*a* may include an optional locking mechanism or locking groove to keep the front and back shafts 125 and 115 fixed and the left and right belts 110 and 120 taut. The locking mechanism may have a release to allow movement of the front and back shafts 125 and 115 toward each other to loosen the left and right belts 110 and 120. As an example, the front roller frames 142*b* may have a curved groove (e.g., L-shaped, upside down L-shaped, S-shaped, etc.) When the upper frame 140 is coupled to the lower frame 150, the front shaft 125 may slide further forward in the groove so as to tighten the left and right belts 110 and 120. The groove on the right front roller frame 142*br* may have a thick size corresponding to a size of the right motor 123, while the groove on the left front roller frame 142*bl* may have a thin size corresponding to a size of the front shaft 125. A vertical section of the grooves may extend all the way down the front roller frames 142*b* for entry of the front shaft 125 into the groove.

As the upper frame 140 is placed downward on the lower frame 120, the front roller frames 142*bl* and 142*br* and the back roller frames 142*al* and 142*ar* may fit onto the front shaft and motor 125 and 123 and back motor and shaft 113 and 115, respectively. The front rollers 112 and 122 may be guided forward by the grooves while the back rollers 111 and 121 may be guided backward by the grooves to tighten the left and right belts 110 and 120.

Figure 10A:
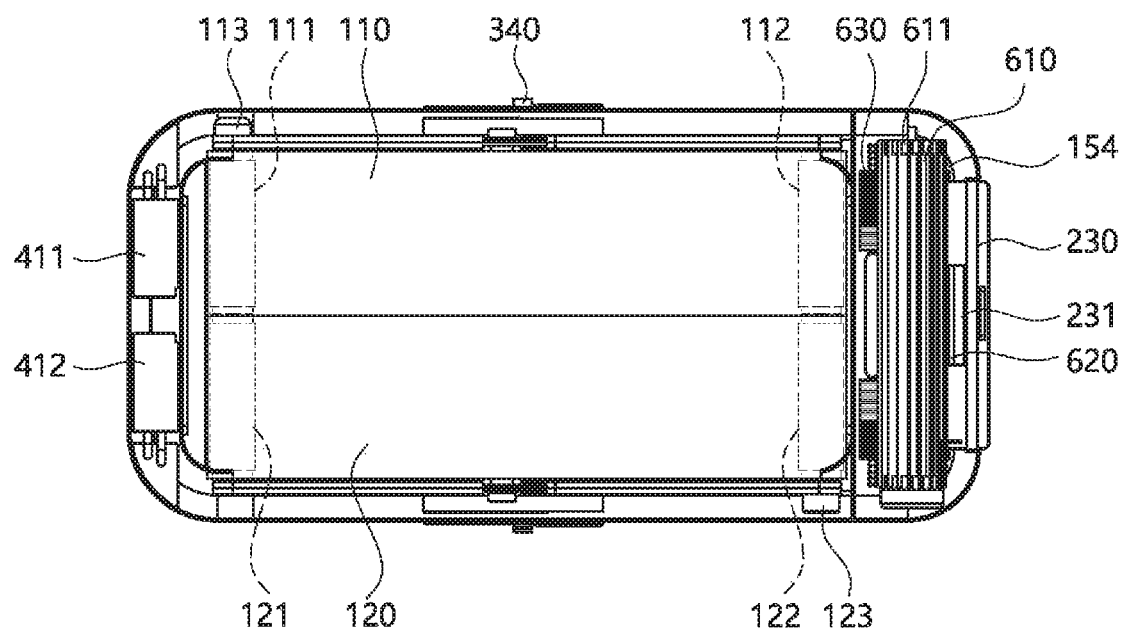
FIG. 10A is a top view of the treadmill of FIG. 8 without a display of the attachment module.
Figure 10B:
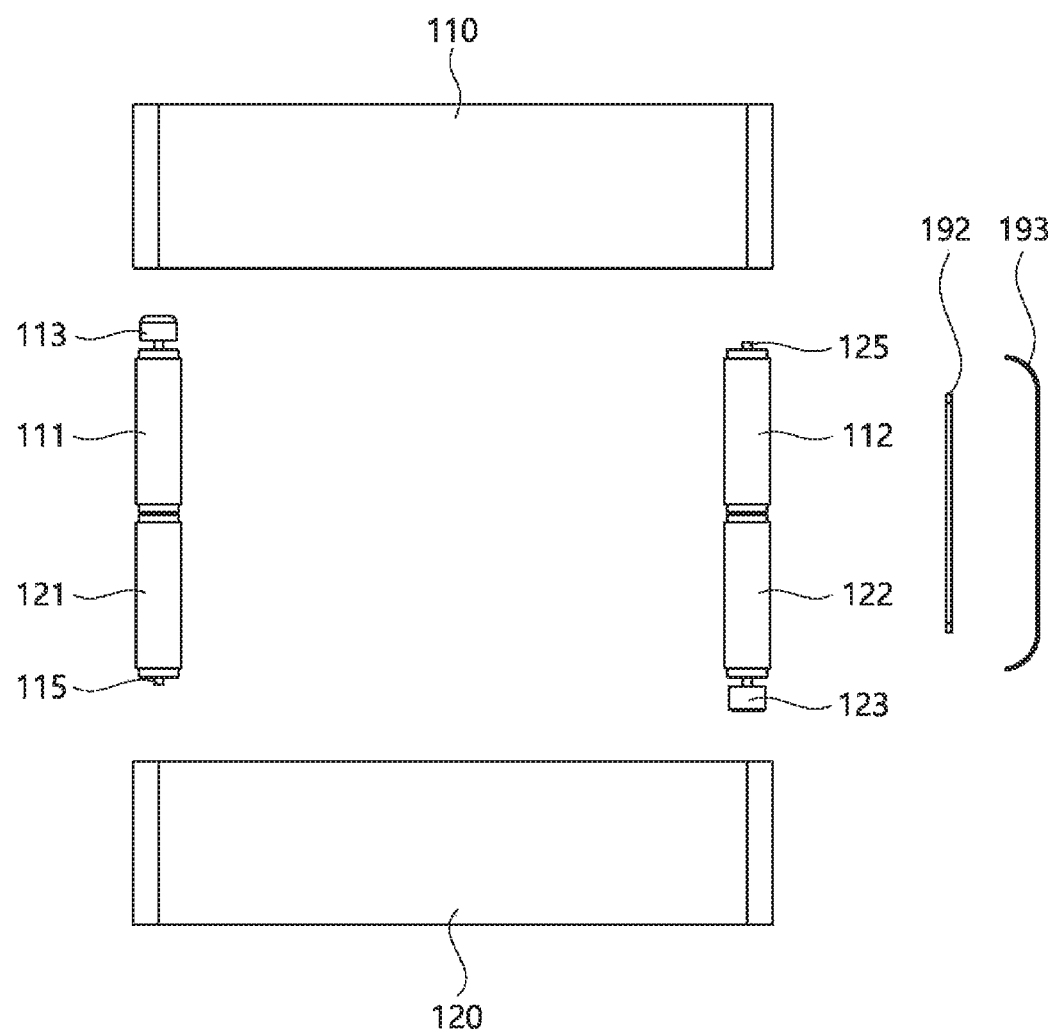
FIG. 10B is a top view of the belts removed from the rollers according to an embodiment.

Although FIG. 10A shows the right motor 123 coupled to the front right roller 122 and the left motor 113 coupled to the back left roller 111, configurations of the motors 113 and 123 and the rollers 111, 112, 121, and 121 are not limited thereto. For example, the motors 113 and 123 may both be provided to rotate the back rollers 111 and 121, may both be provided to rotate the front rollers 112 and 122, or the right motor 123 may rotate the back right belt 121 and the left motor 113 may rotate the front left belt 122.

Although a magnetic coupling of the divider 130 to the upper frame 140 is described, a coupling of the divider 130 is not limited thereto. For example, the divider 130 may be pressed-fit into grooves or recesses provided in the vent frame 147 and the back frame 144 of the upper frame 140, or the divider 130 may be bonded to the vent and back frames 147 and 144.

Although the roller frame 160 described with reference to FIGS. 11-13 is described as having a plurality of left and right rollers 165 and 166, alternatively, the plurality of left and right rollers 165 and 166, along with center rollers 167 and 168, may be omitted, and the roller frame 160 may simply adjust positions of the front rollers 112 and 122 with respect to the back rollers 111 and 121. In such a case, the left and right belts 110 and 120 may be made out of a strong enough material and configured such that, when tensions of the left and right belts 110 and 120 are sufficiently tightened, the left and right belts 110 and 120 may together support a pet under a predetermined weight.

When the plurality of left and right rollers 165 and 166 are omitted, an optional plate may be provided on top of the roller frame 160 and within the closed loops of the left and right belts 110 and 120 after the roller frame 160 is adjusted properly. The plate may be pressed-fit onto upper sides of the front and back frames 161 and 162. The plate may have a rib or flange that extends downward from left and right sides, and the flange may be inserted into grooves on the upper sides of the front and back frames 161 and 162.

As another alternative, back and front plates may replace the plurality of left and right rollers 165 and 166 in the roller frame 160 and be fixed to the back and front frames 162 and 161, respectively. In such an alternative, there may be a gap between the back and front plates depending on a length adjustment of the roller frame 160. The front and back plates may serve to offer temporary support if a pet or object of a weight greater than what the left and right belts 110 and 120 can support is placed on the left and right belts 110 and 120, or if a pet or object is placed on the treadmill 1 before the left and right belts 110 and 120 are sufficiently tightened.

As another alternative, the left and right belts 110 and 120 may not be replaceable, and a plate or inner roller housing may be fixed between the back rollers 111 and 121 at a back end and the front rollers 112 and 122 at a front end, and the left and right belts 110 and 120 may slide over an upper surface of the inner roller housing. The inner rolling housing may be implemented as slates or mesh to reduce a weight. The inner roller housing may support a weight of a pet using the treadmill 1, while the left and right belts 110 and 120 merely encourage movement of the pet on the treadmill 1.

As another alternative, each roller 111, 112, 121, and 112 may have its own shaft, and a vertical plate may be provided on the lower frame 150 or the upper frame 140 to extend between the left rollers 111 and 112 and the right rollers 121 and 122. The shafts may be coupled to grooves or rails provided on the vertical plate and fixed in place so that a position of the front right roller 122 may be adjusted independently from a position of the front left roller 112, and a position of the back left roller 111 may be adjusted independently from a position of the back right roller 121.

As another alternative, the roller frame 160 may replace a part of the lower frame 150, and the upper frame 140 may be configured to have and adjustable length to correspond to the adjustable length of the roller frame 160.

Even when the roller frame 160 is omitted, there may be a plurality of left and right rollers extending between pairs of roller frames 142 provided in the upper frame 140.

Although the handle mount opening 143 is shown as an opening in FIG. 7, alternatively, the handle mount opening 143 may be a recess formed in a side surface of the side wall 145 having a depth that corresponds to a thickness of a handle mount 153 extending upward from the lower frame 150.

Although the handle 300 is described and shown in FIG. 2 as having one handle sensor 331 to sense a height and frontward-backward position of a pet, alternatively or in addition thereto, there may be at least two handle sensors 331 provided at left and right sides of the handle assembly 330 under the handle top 320. Based on information from both the left and right handle sensors 331, the main controller may determine whether a pet is too far to the left or too far to the right on the treadmill 1. Such a detection may also be sensed via the proximity sensors 132 and 133 provided in the divider 130.

If the handle sensor 331 (or, alternatively, the proximity sensors 132 and 133 in the divider 130) senses that a pet is outside of a predetermined distance range from a center of the treadmill 1, the height adjusters 410 and 420 may adjust an inclination of the treadmill 1 by raising or lowering heights of the legs 411a, 412a, 421a, and 422a to shift the pet back to a more central position within the predetermined distance range from a center of the treadmill 1. For example, if it is sensed that a pet is at a position to a right beyond the predetermined distance range, the front and back height adjusters 420 and 410 may raise the front and back right legs 421a and 411a to shift the pet back toward the center of the pet treadmill. Once it is sensed that the pet is within the predetermined distance range from the center of the treadmill 1, the front and back height adjusters 420 and 410 may lower the front and back right legs 421a and 411a back to an initial position so that the pet may continue with a previously started exercise program.

There may be optional weight sensors provided in the lower frame 150. The main controller may make determinations of a position of the pet based on data from the weight sensors.

Figure 16:
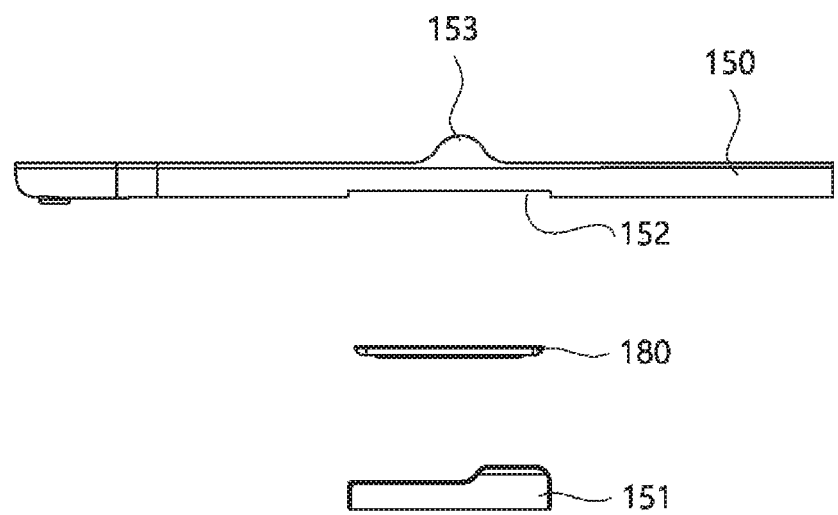
FIG. 16 is an exploded side view of a debris remover and lower frame of a treadmill according to an embodiment.
Figure 17:
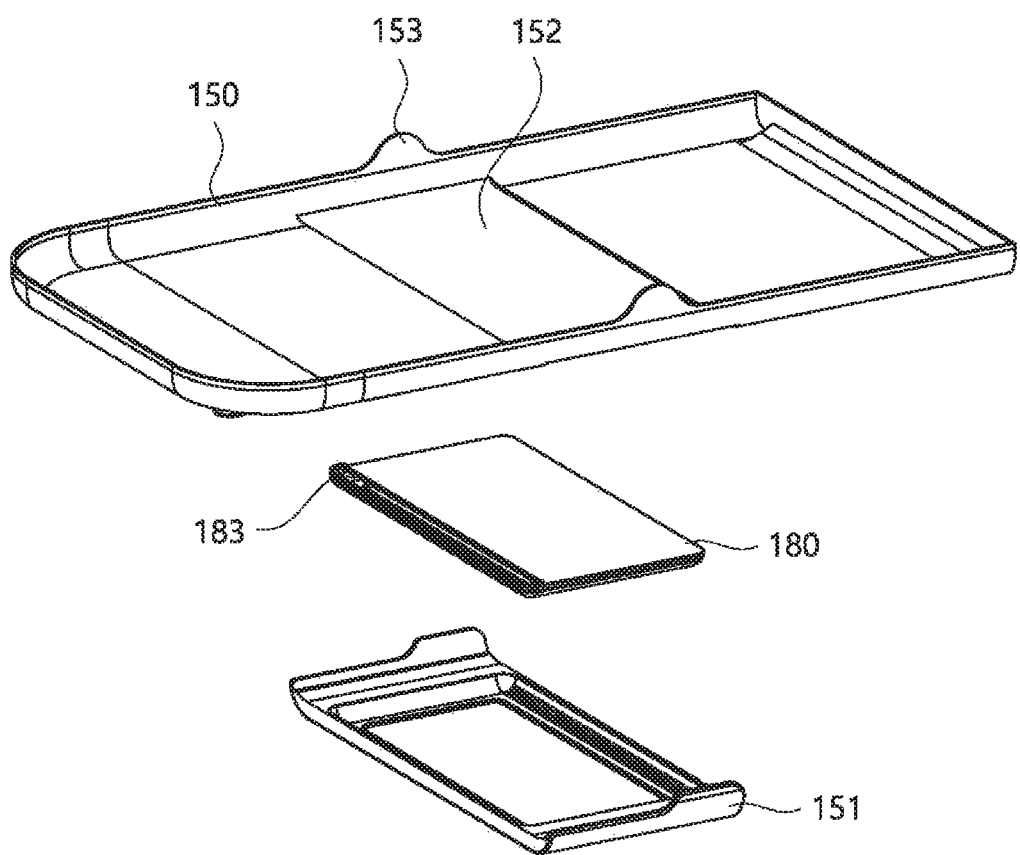
FIG. 17 is an exploded perspective view of the debris remover and lower frame of FIG. 16.
Figure 18:
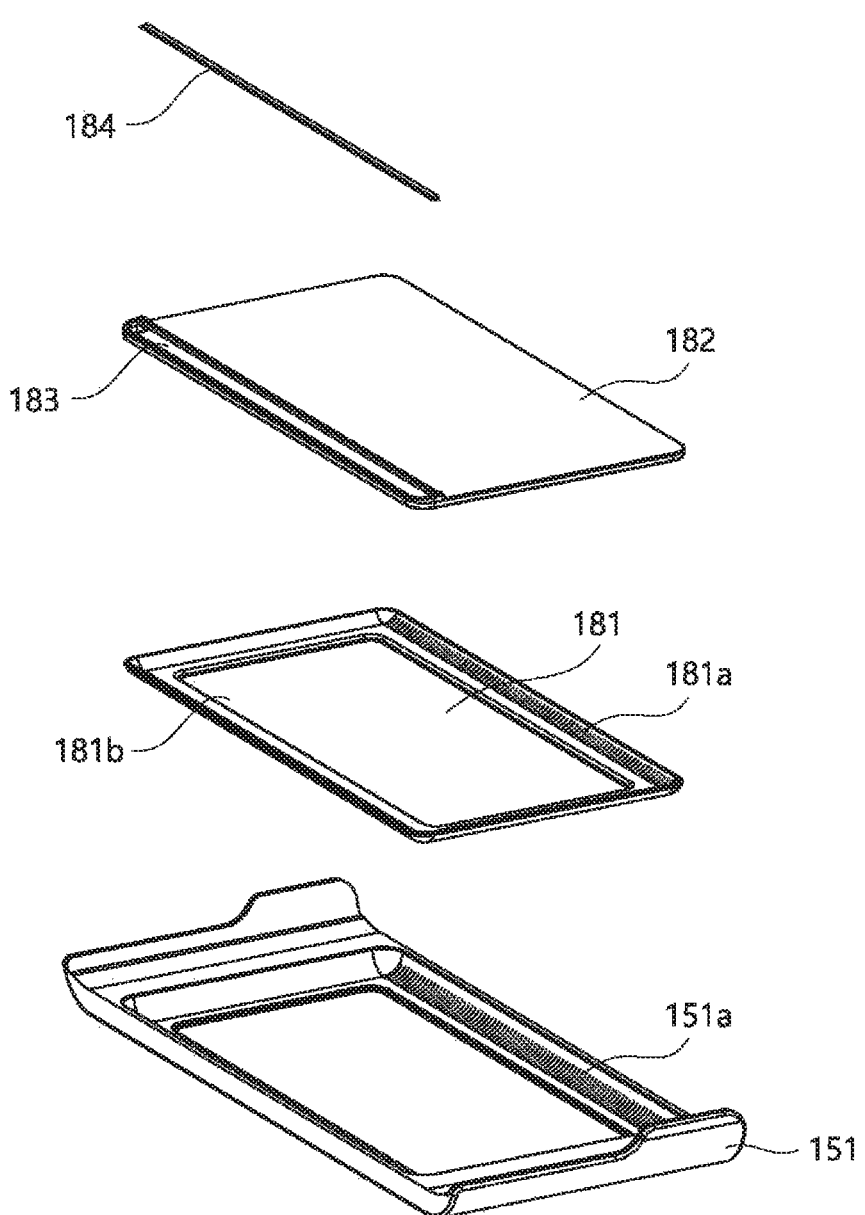
FIG. 18 is an enlarged exploded perspective view of the debris remover of FIG. 16.

With respect to FIGS. 16-18, although a square or rectangular debris remover 180 and opening 152 is exemplified in the figures, embodiments disclosed are not limited to such shapes. Alternatively or in addition thereto, the brush 184 may rotate via a motor to deposit the debris into the opening 183 of the debris remover 180. In addition, a placement of the opening 183 and the brush 184 are not limited to a back end of the debris remover 180, and may alternatively be placed at a front end or in a middle of the debris remover 180, with the opening 183 being provided in front of the brush 184 with respect to a movement of the left and right belts 110 and 120. In addition, a placement of the handle 300 and the debris remover 180 are not limited to a central or middle portion of the base 100. An angle of the handle 300 may be adjusted so that, during exercise, the handle sensor 331 may accurate sense a position of a pet on the left and right belts 110 and 120.

Although the back and front height adjusters 410 and 420 are shown to be provided within the base 100 between the upper and lower frames 140 and 150 in FIG. 1, alternatively, the back and front height adjusters 410 and 420 may be provided under the lower frame 150. In such a case, lengths of the back and front height adjusters 410 and 420 may correspond to lengths of the back and front ends of the base 100, respectively. In addition, the back UV LED 191 and back roller cover 194 may be provided on an inner surface of the back frame 144 of the upper frame 140.

Figure 24:
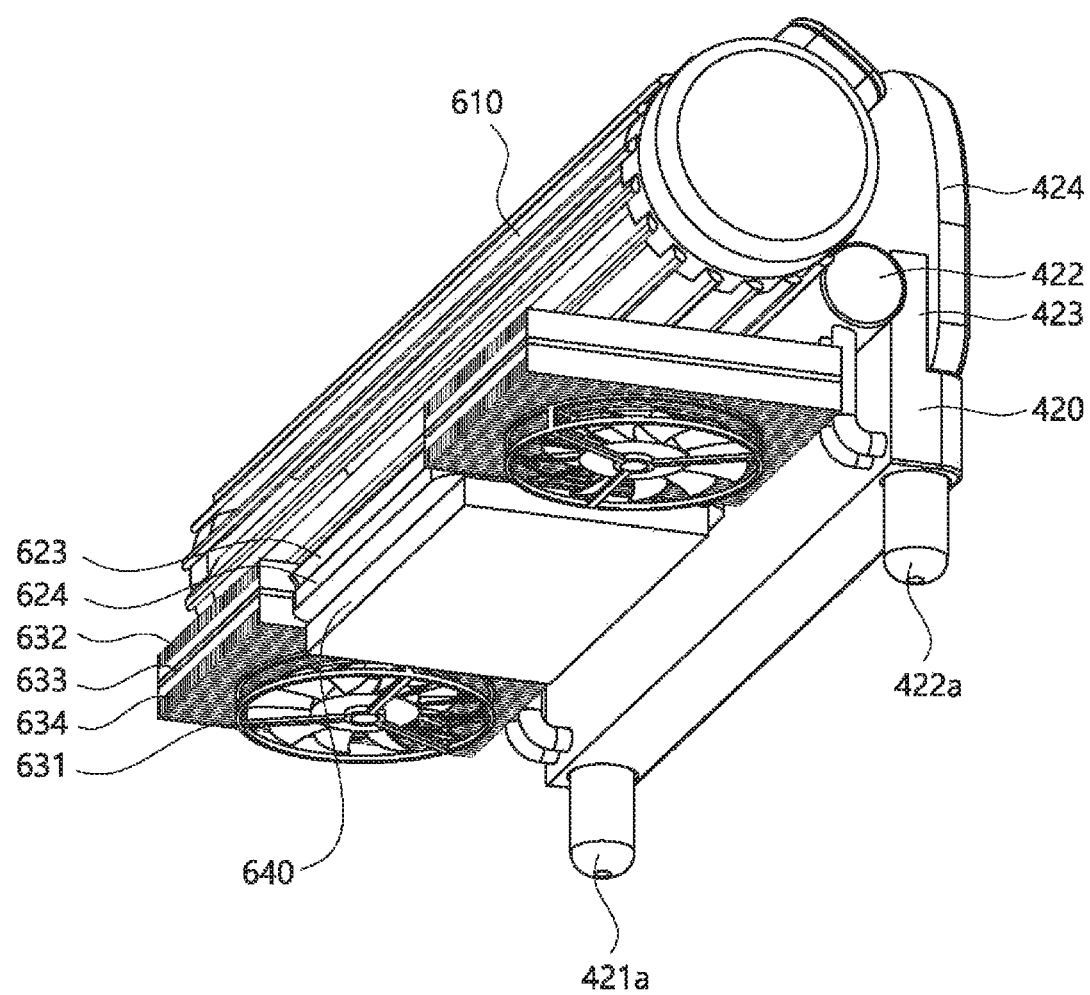
FIG. 24 is a perspective view of the blower and deodorizer of FIG. 23.

Although the FIGS. 22-24 exemplify rectangular or square shaped top and bottom heat sinks 634 and 632 and a Peltier device 633, the Peltier device 633 and the top and bottom heat sinks 634 and 632 alternatively may have a circular shape corresponding to a shape of the fan 631. The number of fans 631, Peltier devices 633, and top and bottom heat sinks 634 and 632 are not limited to two, and various shapes, sizes, and configurations may be provided to address various cooling needs. As an example, there may be a longer, rectangular Peltier device 633 provided between two longer top and bottom heat sinks 634 and 632, while two fans 631 are provided under the longer, bottom heat sink 634. Although the deodorizer 620 is shown to be in a central position between two sets of fans 631, Peltier device 633, and top and bottom heat sinks 634 and 632, a position of the deodorizer 620 is not limited thereto. Similarly, a position of the control module 640 is not limited to the central position shown.

The number of LED modules 623 is not limited to two. For example, there may only be one LED module 623. Alternatively, there may be four LED modules 623 attached to each side of a rectangular photocatalyst housing 624. Although rectangular or square shapes for the LED frame 623a, the photocatalytic deodorizer 622, and the control module 640 are exemplified, embodiments disclosed herein are not limited to square or rectangular shapes.

Although FIGS. 25-26 exemplify a cartridge 504 divided into four sections embodiments disclosed are not limited thereto. For example, the cartridge 504 may be divided into thirds by three walls intersecting at 120°, into halves by two walls intersecting at 180°, into sixths by six walls intersecting at 60°, etc. A shape of the scent modules 505 may be configured to fit into the sections of the cartridge 504.

In addition, scents of the scent modules 505 are not limited. As another example, one of the scent modules 505 may have a meat fragrance, food fragrance, or other fragrance that may be pleasing to an animal to lure a pet to the treadmill 1. As another example, there may be a scent module 505 that emits a rain fragrance to correspond to a rain video, a smoke fragrance to correspond to a campsite or fire video, a sugary fragrance or a fragrance imitating a typical dog or cat scent to lure the pet, etc.

Although an automatic rotation of the cartridge 504 by the motor of the side support 503b is described, the cartridge 504 may also be rotated manually via a dial method or by force. The vent or opening at the bottom of the cartridge case 501 may have vanes that automatically or manually open and close the cartridge case 501 to close the fragrance assembly 500. Similarly, the vents 146 may also be opened and closed manually via a dial method or pressing down on the vents 146 to close the vents 146 and pulling up on the vents 146 to open the vents 146.

As another alternative, the fragrance assembly 500 may not have a cylindrical structure, and instead, the cartridge 504 may have a lattice box structure or grid structure. The plurality of scent modules 505 may have cuboid shape and be arranged side-by-side, and the opening 502a may have a corresponding square or rectangular shape. The cartridge 504 may slide laterally to expose only one scent module 505 through the opening. Alternatively, a gate closing the opening 502a may be configured to cover all of the scent modules 505 except a selected scent module 505. The fragrance assembly 500 is not limited to the base 100, and may alternatively be provided as part of the attachment module 200 to be removable. In such a configuration, the attachment module 200 may have additional vents and a fan to disperse scents from the scent modules 505.

With respect to FIG. 8, since a coupling between the protrusion of the attachment base 240 and the recess of the stand 424 may be configured to be strong enough to support an entire weight of the attachment module 200 (the display 210, the container 230, and the tray 220), the protrusion of the attachment base 240 may alternatively be welded or bonded to the recess of the stand 424.

Although the display mount 211 shown in FIGS. 28-30 appears to be fixed onto the stand 424, alternatively, the stand 424 may be slideably coupled to the front support 423 so that a height of the display mount 211 and the display 210 may be adjusted. A back side of the stand 424 may include gear teeth to interact with a gear provided on a front side of the front support 423, and a motor may turn the gear so that a height of the display 210 may be automatically adjusted.

Combinations and/or customizations of the attachment module 200 are not limited to the above-described omissions with reference to FIGS. 29B and C. When the dispensing tray 220, tray container 221, and container 230 are omitted, the display 210 may alternatively be coupled to the display mount 211 instead of directly to the attachment base 240, and the display mount 211 may couple to the attachment base 240 or alternatively directly to the stand 424. A back surface of the display mount 211 may be adhered or bonded to the attachment base 240 or the stand 424.

Alternatively, the attachment base 240 and/or the stand 424 may have a rail guide provided at sides of the front surface of the stand, and sides (or optional rails) of the display mount 211 may be inserted into the rail guide. As another alternative, the stand 240 may have grooves, and the back surface of the display mount 211 may have protrusions configured to be inserted and pressed-fit into the grooves of the stand 240.

Although FIG. 28A is described as having a protrusion 210a inserted into a hole 211a, alternatively, the protrusion 210a and the hole 211a may be formed as a ball and socket structure. The protrusion 210a may be a sphere or partial sphere, and the hole 211a may be a spherical or semi-spherical recess. The display 210 may have an adjustable inclination up, down, left, right, back, and forward so that the display 210 may be properly aimed at a pet on the treadmill 1.

Although FIG. 31 describes a process where the content on the display 210 is sped up or slowed down according to a speed of the left and right belts 110 and 120, alternatively or in addition thereto, the speed of the left and right belts 110 and 120 may change according to content played on the display 210 or as part of a pre-recorded or pre-programmed exercise program. For example, if a video depicts an increase in travel speed through a road or on a beach, speeds of the left and right belts 110 and 120 may be increased accordingly. However, the speed-linked process exemplified in FIG. 31 allows for unanticipated changes in the speeds of the left and right belts 110 and 120. For example, if a speed of the left and right belts 110 and 120 is decreased because it is sensed via the handle sensor 331 that a pet is too far backward on the treadmill 1, content on the display 210, even if part of a pre-recorded exercise program, may still correspond to a speed of the left and right belts 110 and 120 and therefore produce a more realistic simulation for the pet.

This application is related to co-pending U.S. application Ser. No. 16/690,201 filed on Nov. 21, 2019, Ser. No. 16/690,239 filed on Nov. 21, 2019, Ser. No. 16/690,271 filed on Nov. 21, 2019, Ser. No. 16/690,312 filed on Nov. 21, 2019, Ser. No. 16/690,371 filed on Nov. 21, 2019, Ser. No. 16/690,500 filed on Nov. 21, 2019, Ser. No. 16/690,573 filed on Nov. 21, 2019, Ser. No. 16/691,707 filed on Nov. 21, 2019, Ser. No. 16/691,718 filed on Nov. 22, 2019, Ser. No. 16/691,736 filed on Nov. 22, 2019, Ser. No. 16/691,743 filed on Nov. 22, 2019, Ser. No. 16/691,759 filed on Nov. 22, 2019, Ser. No. 16/691,779 filed on Nov. 22, 2019, and Ser. No. 16/691,796 filed on Nov. 22, 2019, the entire contents of which are hereby incorporated by reference.

Features of the present disclosure may be implemented by a treadmill having two belts, one for each leg, that move at different speeds to accommodate a gait of the pet. Gait of the pet may be detected by position sensors provided to sense a distance of right and left legs away from a center of the treadmill.

Features of the present disclosure may be implemented by a treadmill that maintains a position of a pet on the treadmill so that the treadmill may be used autonomously. A sensor provided above the pet may detect a height and forward-backward position of the pet, while sensors provided in a belt divider may detect a left-right position of the pet. When the pet is too far forward or backward, speeds of the left and right belts may be adjusted to bring the pet back to the center. In addition, a forward-backward inclination of the treadmill may be adjusted to push the pet back toward the center. When the pet is too far leftward or rightward, speeds of the left and right belts may be adjusted to accommodate any gait detected, and a left-right inclination of the treadmill may be adjusted to push the pet back toward the center.

Features of the present disclosure may be implemented by a treadmill that summons a pet to the treadmill and keeps the pet stimulated. The pet may be lured to the treadmill by a video, sound, smell, or treat, and may continue to be simulated in on the treadmill in accordance with an exercise program. The program may simulate a landscape or seascape (e.g., a flower road video, rocky road video, mountain video, coastal landscape video, or beach landscape), and the videos, sounds, and smells via a display, treat dispenser, and fragrance assembly may all work in conjunction to simulate the landscape. When speeds of the belts are adjusted based on sensed positions of the pet, a simulated movement on the display may be adjusted. In addition, a texture of the belts may simulate a texture of the landscape (e.g., an AstroTurf belt or sand-based belt). A thermoelectric cooler may cool the pet on the treadmill. A pet on the treadmill may not need to be caged in, which may reduce anxiety.

Features of the present disclosure may be implemented by an easily customizable treadmill. Belts of the treadmill may be replaceable with other belts having different textures. In addition, a display and treat dispenser may be easily removed or combined in various ways on the treadmill.

Features of the present disclosure may be implemented by a treadmill that is easy to keep clean. A debris remover may be provided under the belts to scrape pet hair and other debris off the belts. A deodorizer may be provided to break apart pollutants in the air, and a sterilizer may be provided to emit UV radiation toward the belts.

Features of the present disclosure may be implemented by a lightweight and portable treadmill for home use. A handle is provided that rotates around the treadmill to provide easy storage. During use, the handle may extend over the belts, and a height may be automatically adjusted based on a sensed height of the pet. In addition, a stand is provided to support the treadmill in an upright position during storage. An attachment module, which may include a display, speaker, and treat dispenser, may be easily removed so that the display is not damaged during storage.

Features of the present disclosure may be implemented by a treadmill designed for dogs. DogTV or other programs geared toward dogs may be played on the display. Colors and sounds output on the display may be in the visual and audio spectrum for dogs. A fragrance assembly may be provided to store a plurality of scents and emit one of the scents to lure a pet to the treadmill or stimulate the pet during an exercise program.

Embodiments disclosed herein may be implemented as a treadmill comprising a base, at least one belt moveable relative to the base, an attachment module including at least one of a display configured to display an image for a pet or a dispenser configured to dispense a consumable item, the attachment module being removable from the base, a fragrance assembly configured to emit at least one scent and provided in the base, and, a blower provided in the base and configured to disperse the scent emitted by the fragrance assembly through an opening in the base.

Embodiments disclosed herein may be implemented as a treadmill comprising a base, a tread moveable relative to the base and having a first belt and a second belt, the first belt and the second belt being controlled independently for speed, a stimulation module configured to entice a pet to exercise and to operate in accordance with an exercise program, the stimulation module including at least one of a display that plays videos, a dispenser that dispenses an edible treat, or a fragrance assembly that emits at least one scent, and a cleaning module including at least one of a deodorizer that emits ions, a sterilizing light configured to sterilize the belt, or a debris remover configured to remove and collect debris from the tread.

Embodiments disclosed herein may be implemented as a treadmill including a base, a first belt provided over a first pair of rollers and a second belt provided over a second pair of rollers, the first belt and the second belt being moveable relative to the base in a prescribed direction. One of the first pair of rollers may be provided toward a front of the base and the other one of the first pair of rollers may be provided toward a rear of the base. One of the second pair of rollers may be provided toward a front of the base and the other one of the second pair of rollers may be provided toward a rear of the base such that the first and second belts are adjacent to each other. A first motor may be coupled to one of the first pair of rollers and a second motor may be coupled to one of the second pair of rollers such that the first belt and the second belt are independently driven for speed. A divider may be provided between the first belt and the second belt, the divider including a left sensor and a right sensor to detect whether a pet may be centered between the first and second belts. A handle may be attached to a middle portion of the base, the handle having a top sensor to detect whether a pet may be close to the front or rear of the base, the middle portion provided between the front and the rear of the base.

Embodiments disclosed herein may be implemented as a treadmill comprising a base having a front end and a rear end and a first pair of rollers and a second pair of rollers. One of the first pair of rollers may be provided toward the front end of the base and the other one of the first pair of rollers may be provided toward the rear end of the base. One of the second pair of rollers may be provided toward the front end of the base and the other one of the second pair of rollers may be provided toward the rear end of the base such that the first and second pairs of rollers are adjacent to each other. A first belt may be wrapped around the first pair of rollers. A second belt may be wrapped around the second pair of rollers. A first motor may be configured to rotate one of the first pair of rollers such that the first belt moves from the front end of the base to the rear end of the base at a first linear speed. A second motor may be configured to rotate one of the second pair of rollers such that the second belt moves from the front end of the base to the rear end of the base at a second linear speed.

Embodiments disclosed herein may be implemented as a treadmill comprising a base having a front and a rear and a first pair of rollers and a second pair of rollers. One of the first pair of rollers may be provided toward the front end of the base and the other one of the first pair of rollers may be provided toward the rear end of the base. One of the second pair of rollers may be provided toward the front end of the base and the other one of the second pair of rollers may be provided toward the rear end of the base such that the first and second pairs of rollers are adjacent to each other. A first belt may be wrapped around the first pair of rollers. A second belt may be wrapped around the second pair of rollers. A first motor may be configured to rotate one of the first pair of rollers such that the first belt moves from the front end of the base to the rear end of the base at a first linear speed. A second motor may be configured to rotate one of the second pair of rollers such that the second belt moves from the front end of the base to the rear end of the base at a second linear speed. A first sensor may face toward the first belt and a second sensor may face toward the second belt to detect a position as to whether a pet may be veering away from a center of the base due to a gait, and a control module may be configured to adjust rotational speeds of the first and second motors in response to the detected position to compensate for the gait.

Embodiments disclosed herein may be implemented as a treadmill comprising a base having a front and a rear and a first pair of rollers and a second pair of rollers. One of the first pair of rollers may be provided toward the front of the base and the other one of the first pair of rollers may be provided toward the rear of the base. One of the second pair of rollers may be provided toward the front of the base and the other one of the second pair of rollers may be provided toward the rear of the base such that the first and second pairs of rollers are adjacent to each other. A first belt may be wrapped around the first pair of rollers to form a first closed loop. A second belt may be wrapped around the second pair of rollers to form a second closed loop.

Embodiments disclosed herein may be implemented as a treadmill comprising a base including a bottom frame having a front end with left and right corners and a rear end with left and right corners, a tread configured to move relative to the base, the tread being provided above the bottom frame, and an adjustment assembly configured to independently adjust a front left corner height of the bottom frame, a front right corner height of the bottom frame, a rear left corner height the bottom frame, and a rear right corner height of the bottom frame to assist a pet to be positioned at a predetermined location on the tread.

Embodiments disclosed herein may be implemented as a treadmill comprising a base including a front end and a rear end, a tread configured to move relative to the base, a sensor provided above the tread and facing toward the tread, and an adjustment assembly configured to independently adjust at least one of a height of the front end or the rear end to assist a pet to be positioned at a predetermined location on the tread based on a position detected by the sensor.

Embodiments disclosed herein may be implemented as a treadmill comprising a base including a right side and a left side, a tread configured to move relative to the base, a sensor provided toward a front of the base to sense a position of a pet relative to at least one of the right side or the left side, and an adjustment assembly configured to independently adjust at least one of a height of the left side or the right side to assist a pet to be positioned at a predetermined location on the tread based on a position detected by the sensor.

Embodiments disclosed herein may be implemented as a treadmill for a pet comprising a base having a first end and a second end, a first roller provided at the first end of the base and a second roller provided at the second end of the base, a display coupled to the base and configured to display content according to a predetermined exercise program, and a belt formed around the first roller and the second roller to form a closed loop and configured to move around the first and second rollers at a prescribed speed. The belt may have an outer surface and be configured to be removable such that content played on the display may be based on the texture of the belt and the outer surface corresponds to a texture of a ground surface displayed on the display. The texture of the belt may include at least one of a rocky surface, a grassy surface, a gravel surface, a pavement surface, or a sandy surface.

Embodiments disclosed herein may be implemented as a treadmill for a pet including a base having a first end and a second end, the base having a first frame and a second frame coupled to the first frame, the first frame being configured to be separable from the lower frame, at least one first roller and at least one second roller separated from each other by a prescribed distance, at least one motor to rotate at least one of the first roller or the second roller, and a belt assembly having an inner surface configured to wrap around the first and second rollers to form a closed loop and an outer surface having a first predetermined texture. The first frame and the second frame may be separated from each other to replace the belt assembly with a replacement belt assembly having an outer surface of a second predetermined texture which may be different from the first predetermined texture.

Embodiments disclosed herein may be implemented as a treadmill for a pet comprising a base having a plurality of rollers comprising a front left roller, a front right roller, a rear left roller, and a rear right roller, and a belt assembly having an outer surface and configured to wrap around the front left and right rollers and the back left and right rollers. The belt assembly may be formed of one of a single belt and a left belt and a right belt. The outer surface may be made of at least one of an AstroTurf material, a GoreTex material filled with sand, a gravel material, or a material configured to imitate grass, sand, gravel, or pavement.

Embodiments disclosed herein may be implemented as a treadmill for a pet comprising a base having a first end and a second end, a first roller provided at the first end of the base and a second roller provided at the second end of the base, at least one belt having an inner surface and an outer surface, the inner surface being wrapped around the first roller and the second roller to form a closed loop, the belt being configured to move around the first and second rollers at a prescribed speed, and a first sterilizer provided at the first end of the base and adjacent to the belt such that the belt may be provided between the first sterilizer and the first roller. The first sterilizer may be configured to sterilize the outer surface of the belt as the belt travels at the prescribed speed. The first sterilizer may be an ultraviolet light emitting diode (UV LED).

Embodiments disclosed herein may be implemented as a treadmill for a pet comprising a base having an opening, at least one belt exposed through the opening of the base and configured to travel at a prescribed speed in a closed loop, and a sterilizer configured to sterilize the belt. The sterilizer may be provided in the base to face toward the belt such that light emitted by the sterilizer may be prevented from escaping through the opening.

Embodiments disclosed herein may be implemented as a treadmill for a pet comprising a base having an opening, a front cover provided at a front, and a rear cover provided at a rear, the opening provided between the front and rear covers, a first roller provided at the front and a second roller provided at the rear, a belt configured to wrap around the first roller and the second roller and configured to move at a prescribed speed, a section of the belt being exposed through the opening, and a sterilizing light provided between the rear cover and the second roller and configured to emit light toward the belt. The rear cover may be configured to at least partially cover the second roller to prevent light from the sterilizing light from being emitted outside of the base. A front sterilizer may be provided on the front cover to face the belt.

Embodiments disclosed herein may be implemented as a treadmill for a pet comprising a base having a first end, a second end, and an opening between the first and second ends, a first roller provided at the first end of the base and a second roller provided at the second end of the base, at least one belt having an inner surface and an outer surface, the inner surface being wrapped around the first roller and the second roller to form a closed loop and a section of the outer surface being exposed, the belt being configured to move around the first and second rollers at a prescribed speed, and a deodorizer provided in the base to release ions for neutralizing pollutants. The pollutants may include at least odor particles.

Embodiments disclosed herein may be implemented as a treadmill for a pet comprising a base having a first section that may be covered, a second section having an upper opening, and a plurality of vents provided between the first and second sections of the base, a belt configured to move relative to the base and exposed through the upper opening of the second section of the base, a deodorizer provided in the first section of the base and configured to release ions, and a blower provided adjacent to the deodorizer to blow the ions through the vents to break apart pollutants in the air at least above the upper opening of the base.

Embodiments disclosed herein may be implemented as a treadmill for a pet comprising a base having a plurality of vents, first and second rollers provided below the vents and spaced apart from each other by a prescribed distance, and third and fourth rollers provided below the vents and spaced apart from each other by the prescribed distance. A first belt may be wrapped around the first and second rollers to form a first closed loop. A section of the first closed loop may be exposed and be adjacent to a first side of the vents. A second belt may be wrapped around the third and fourth rollers to form a second closed loop. A section of the second closed loop may be exposed and being adjacent to a first side of the vents. A deodorizer may be provided in the base at a second side of the vents and configured to release ions. A blower may be provided adjacent to the deodorizer to blow the ions from the first side to the second side of the vents to break apart pollutants in the air at least above the sections of the first and second closed loops.

Embodiments disclosed herein may be implemented as a treadmill for a pet comprising a base having a first end, a second end, and an opening between the first and second ends, a first roller provided at the first end of the base and a second roller provided at the second end of the base, a first belt wrapped around the first roller and the second roller to form a first closed loop having a section exposed through the opening, the first belt being configured to move around the first and second rollers at a first prescribed speed, and a fragrance assembly having a plurality of scent modules, each scent module storing one scent. The fragrance assembly may be configured to release a scent from one of the plurality of scent modules toward the exposed section of the belt to entice a pet to exercise. A scent module may be configured to release one of a floral fragrance, a phontycide fragrance, or a beach fragrance.

Embodiments disclosed herein may be provided as a treadmill for a pet comprising a base having a first end, a second end, and an opening between the first and second ends, a first roller provided at the first end of the base, and a second roller provided at the second end of the base. A first belt may have an inner surface and an outer surface. The inner surface may be wrapped around the first roller and the second roller to form a first closed loop. A section of the outer surface may be exposed. The first belt may be configured to move around the first and second rollers at a first prescribed speed. A display may be coupled to the first end of the base and may be configured to output at least one of an image, video, or sound. A fragrance assembly may be configured to release a scent based on content output on the display.

Embodiments disclosed herein may be implemented as a fragrance assembly comprising a case configured to expose an opening in the case and a cartridge having a cylindrical shape and provided in the case. The cartridge may be divided into multiple sections by recesses provided in an outer circumferential surface. The cartridge may be rotatable within the case to align a section of the cartridge with the opening. A plurality of scent modules may be provided in the sections of the cartridge to be exposed through the opening. Each scent module may include a fragrant material. At least one of the cartridge or a scent module may be configured to be removed and replaced with a replacement cartridge or a replacement scent module, respectively.

Embodiments disclosed herein may be implemented as a treadmill for a pet comprising a base, a first roller and a second roller spaced apart from each other and supported in the base, a first belt wrapped around the first roller and the second roller to form a first closed loop, the first belt being configured to move around the first and second rollers at a first prescribed speed, an attachment support removably coupled to the base, and a dispenser removably coupled to the attachment support and configured to dispense an edible item based on location data of a pet, location data of an owner, and stored exercise data on prior exercise sessions of the pet.

Embodiments disclosed herein may be implemented as a treadmill for a pet comprising a base having a front surface. A first roller and a second roller may be spaced apart from each other in a first direction and provided behind the front surface of the base. A first belt may be wrapped around the first roller and the second roller and may be configured to move around the first and second rollers at a first prescribed speed in a first closed loop. A customizable module may be removably coupled to the base. The customizable module may be customized to include at least one of a display or a treat dispenser. In an exercise configuration, the customizable module may be fitted onto the front surface of the base. In a storage configuration, the customizable module may be removed, and the first belt may extend in a second direction perpendicular to the first direction in the storage mode such that the front surface of the base may be facing a ground surface.

Embodiments disclosed herein may be implemented as a treadmill for a pet comprising a base, a first roller and a second roller spaced apart from each other and supported in the base, a first belt forming a first closed loop around the first roller and the second roller, a handle rotatably coupled to a middle portion of the base, the handle being configured to rotate to a first position to cross over the first belt and to a second position adjacent to a side of the base, and a sensor provided in the handle to detect a pet on the first belt.

Embodiments disclosed herein may be implemented as a portable treadmill comprising a base, a first roller and a second roller spaced apart from each other and supported in the base, a first belt forming a first loop around the first roller and the second roller, and a handle rotatably coupled to a middle portion of the base. The handle may be configured to rotate to a first position to cross over the belt and to a second position adjacent to a side of the base. Either in the first or second position, the base may be lifted using the handle for portability from a first location to a second location.

Embodiments disclosed herein may be implemented as a treadmill for a pet comprising a base having a front, a rear, a left, and a right, a first roller provided at the front of the base and a second roller provided at rear of the base, and a first belt wrapped around the first roller and the second roller to form a first closed loop. The first belt may be configured to move around the first and second rollers at a first prescribed speed. A first motor may be configured to drive the first roller. An adjustment assembly may be configured to adjust an inclination of the base relative to a floor surface in a front-rear direction and in a left-right direction. At least one sensor may sense a front-rear position of a pet between the front and rear of the base and a left-right position of the pet between the left and right of the base. At least one of the front-rear inclination of the base, left-right inclination of the base, or a speed of the first belt is adjusted based on the positions sensed by the sensor.

Embodiments disclosed herein may be implemented as a treadmill for a pet comprising a base having a front, a rear, a left, and a right, a first roller provided at the front of the base and a second roller provided at rear of the base, and a first belt wrapped around the first roller and the second roller to form a first closed loop. The first belt may be configured to move around the first and second rollers at a first prescribed speed. A first motor may be configured to drive the first roller. An adjustment assembly may be configured to adjust of an inclination of the base relative to a floor surface in a left-right direction. At least one sensor may sense a left-right position of the pet between the left and right of the base. At least one of the left-right inclination of the base or the first prescribed speed of the belt may be adjusted based on the positions sensed by the sensor.

Embodiments disclosed herein may be implemented as a treadmill for a pet comprising a base having a front, a rear, a left, and a right, a left belt provided at the left of the base and moving at a first prescribed speed in a first closed loop according to an exercise program, a right belt provided at right left of the base and moving at a second prescribed speed in a second closed loop according to the exercise program, an adjustment assembly configured to adjust an inclination of the base to raise a front left height, a front right height, a rear left height, and a rear right height according to the exercise program, and at least one lateral sensor to sense a left-right position of the pet between the left and right of the base. When a pet is sensed to be too far to the left, the exercise program may be changed such that at least one of the first prescribed speed of the left belt is reduced, the second prescribed speed of the right belt is increased, a front left height is increased, a front right height is decreased, a rear left height is increased, or rear right height is decreased. When a pet is sensed to be too far to the right, the exercise program may be changed such that at least one of the first prescribed speed of the left belt is increased, the second prescribed speed of the right belt is decreased, the front left height is decreased, the front right height is increased, the rear left height is decreased, or the rear right height is increased.

Embodiments disclosed herein may be implemented as a method for controlling a pet treadmill having a front, a rear, and a belt moving from the front to the rear. The method may comprise sensing a position of the pet and determining, based on the sensed position, whether the pet is within a first predetermined distance range from the rear. The method may comprise, when the pet is within the first predetermined distance range, decreasing a speed of the belt. The method may comprise, when the pet is not within the first predetermined distance range from the rear, determining whether the pet is within a second predetermined distance range from the front. The method may comprise, when the pet is within the second predetermined distance range, increasing the speed of the belt.

Embodiments disclosed herein may be implemented as a method for controlling a pet treadmill having a front, a rear, a first side, a second side, and a belt moving from the front to the rear. The method may comprise sensing a position of the pet, and determining, based on the sensed position, whether the pet is within a first predetermined distance range from the first side. The method may comprise, when the pet is within the first predetermined distance range, performing at least one of raising a height of the first side of the front, raising a height of the first side of the rear, lowering a height of the second side of the front, or lowering a height of the second side of the rear. The method may comprise, when the pet is not within the predetermined distance range from the rear, determining whether the pet is within a second predetermined distance range from the second side. The method may comprise, when the pet is within the second predetermined distance range, performing at least one of lowering a height of the first side of the front, lowering a height of the first side of the rear, raising a height of the second side of the front, or raising a height of the second side of the rear.

Embodiments disclosed herein may be implemented as a method for controlling a pet treadmill comprising obtaining a location of a pet relative to the pet treadmill, obtaining a location of an owner relative to the pet treadmill, storing information about when the pet uses the pet treadmill, determining whether the pet is within a first predetermined distance from the pet treadmill, when it is determined that the pet is not within the first predetermined distance, implementing one of a sleep mode, storage mode, or off mode, when it is determined that the pet is within the first predetermined distance, determining whether the owner is outside of a second predetermined distance from the pet treadmill, when it is determined that the owner is not outside of the second predetermined distance, implementing a manual mode, and when it is determined that the owner is outside of the second predetermined distance, implementing an away mode.

Embodiments disclosed herein may be implemented as a treadmill for a pet comprising a base having a first end and a second end, a first roller provided at the first end of the base and a second roller provided at the second end of the base, a first belt wrapped around the first roller and the second roller to form a first closed loop, the first belt being configured to move around the first and second rollers at a first prescribed speed, at least one thermoelectric assembly configured to heat or cool air, and a blower configured to disperse the air heated or cooled by the thermoelectric assembly toward the first belt.

Embodiments disclosed herein may be implemented as a treadmill for a pet comprising a base having a first section that may be covered, a second section having an upper opening, and a plurality of vents provided between the first and second sections of the base, at least one belt configured to move relative to the base and exposed through the upper opening of the second section of the base, and at least one thermoelectric assembly configured to heat or cool air. The thermoelectric assembly may be provided in the first section of the base behind the plurality of vents. A blower may be provided in the first section of the base and may be configured to blow air heated or cooled by the thermoelectric assembly through the plurality of vents.

Embodiments disclosed herein may include a treadmill for a pet comprising a base having a top and a bottom, a first roller and a second roller spaced apart from each other and supported in the base, and a first belt forming a first closed loop around the first roller and the second roller. The first belt may be configured to move around the first roller and the second roller at a first prescribed speed. A section of the first belt may be exposed through the top of the base. A storage container may be provided at the bottom of the base and be configured to collect debris removed from the first belt as the first belt moves at the first prescribed speed.

Embodiments disclosed herein may be implemented as a treadmill for a pet comprising a base, a first roller and a second roller spaced apart from each other and supported in the base, a first belt forming a first closed loop around the first roller and the second roller, the first belt being configured to move around the first roller and the second roller at a first prescribed speed, and at least one first surface contacting the first belt to induce a static cling on the first belt as the first belt moves at the first prescribed speed. The first surface may be formed by at least one of a brush, a felt, a scraper, a sweeper, or a bristle that contacts an outer surface of the first belt.

Embodiments disclosed herein may be implemented as a treadmill for a pet comprising a base, a tread moving relative to the base, and a cleaning assembly. The cleaning assembly may comprise at least one ultraviolet light configured to emit ultraviolet radiation toward the tread, a deodorizer having a photocatalytic deodorizer configured to release ions to break apart pollutants including at least one odor in air above at least the tread when light may be shined on the photocatalytic deodorizer, and a debris remover having a first surface contacting the tread to induce a static charge on the tread and a container configured to store debris. Debris clinging to the tread may be scraped off the tread by the first surface and deposited into the container as the tread moves at a first prescribed speed.

Embodiments disclosed herein may be implemented as a treadmill for a pet comprising a base including an upper frame and a lower frame, and a first roller and a second roller spaced apart from each other by a prescribed distance and supported in the base. The first and second rollers may be coupled to the upper frame. A first belt may form a first closed loop around the first roller and the second roller. The first belt may be configured to be removed from the first roller and the second roller. A belt tension adjuster may be configured to change the prescribed distance to adjust a tension of the first belt.

Embodiments disclosed herein may be implemented as a treadmill for a pet comprising a base, a tread moveable relative to the base, and a frame removable from the base and having at least one front roller provided at a front and at least one rear roller provided at a rear. The tread may be configured to wrap around the front roller and the rear roller. The frame may have an adjustable length.

Embodiments disclosed herein may be implemented as a pet treadmill comprising a base, at least one front roller and at least one rear roller spaced apart from the front roller by a prescribed distance, a plurality of rollers provided between the front roller and the rear roller, a tread configured to wrap around the front roller, rear roller, and plurality of rollers to form a closed loop, and at least one motor configured to drive at least one of the front roller or the rear roller. The prescribed distance may be adjusted to adjust a tension of the tread.

Embodiments disclosed herein may be implemented as a method for controlling a treadmill for a pet having a belt. The method may comprise storing information about when a predetermined exercise program has been performed, the predetermined exercise program including predetermined conditions including a predetermined speed of the belt, and determining whether the treadmill is in a manual mode or an automatic mode. Then the treadmill is in a manual mode, the method may comprise performing the predetermined exercise program when an owner inputs a start command. When the treadmill in an automatic mode, the method may comprise determining whether a predetermined rest time has elapsed since the predetermined exercise program has been performed. When the predetermined rest time has elapsed, the method may comprise sensing whether a pet is present on the belt. When the pet is present on the belt, the method may comprise performing the predetermined exercise program. Performing the predetermined exercise program may include operating the belt to move at the predetermined speed.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A treadmill for a pet, comprising:
   a base having a first end, a second end, and an opening between the first and second ends;
   a first roller provided at the first end of the base and a second roller provided at the second end of the base;
   at least one belt having an inner surface and an outer surface, the inner surface being wrapped around the first roller and the second roller to form a closed loop and a section of the outer surface being exposed, the belt being configured to move around the first and second rollers at a prescribed speed; and
   a deodorizer provided in the base to release ions for neutralizing pollutants, wherein the pollutants include at least odor particles.

2. The treadmill of claim 1, wherein the deodorizer includes a photocatalytic deodorizer and at least one light module, the photocatalytic deodorizer being configured to emit ions when light emitted by the light module is irradiated on the photocatalytic deodorizer.

3. The treadmill of claim 2, wherein the photocatalytic deodorizer is made of or coated in at least one of titanium or titanium dioxide.

4. The treadmill of claim 2, wherein the deodorizer includes a photocatalyst housing in which the photocatalytic deodorizer is provided, and the at least one light module is coupled to the photocatalyst housing, wherein the photocatalyst housing includes an opening to expose a section of the photocatalytic deodorizer.

5. The treadmill of claim 4, wherein the at least one light module includes a first light module and a second light module, the first light module coupled to a first side of the photocatalyst housing and the second light module coupled to a second side of the photocatalyst housing opposite the first side, wherein the first and second light modules are inclined to face toward the exposed section of the photocatalytic deodorizer.

6. The treadmill of claim 1, wherein the base includes at least one vent and a blower provided behind the vent, the deodorizer being provided adjacent to the blower, which is configured to disperse ions from the deodorizer through the vent.

7. The treadmill of claim 6, wherein the first end is a front end of the base, and the blower and the deodorizer are provided at the front end.

8. The treadmill of claim 6, wherein the base includes a fragrance assembly provided behind the vent and adjacent to the blower, the fragrance assembly being configured to release at least one scent which is blown through the vent by the blower.

9. The treadmill of claim 8, wherein the deodorizer is provided at a first side of the blower and the fragrance assembly is provided at a second side of the blower opposite the first side.

10. The treadmill of claim 8, wherein the fragrance assembly has an opening which is closed to prevent release of the scent when the deodorizer is operating.

11. The treadmill of claim 6, wherein the base includes a thermoelectric assembly provided adjacent to the blower and configured to heat or cool air which is blown through the vent by the blower.

12. The treadmill of claim 11, wherein the thermoelectric assembly includes a first thermoelectric cooler and a second thermoelectric cooler, and the deodorizer is provided between the first thermoelectric cooler and the second thermoelectric cooler.

13. The treadmill of claim 12, wherein each of the first and second thermoelectric coolers includes a Peltier device, at least one heat sink provided at at least one of above or below the Peltier device, and a fan provided under the Peltier device.

14. A treadmill for a pet, comprising:
a base having a first section that is covered, a second section having an upper opening, and a plurality of vents provided between the first and second sections of the base;
a belt configured to move relative to the base and exposed through the upper opening of the second section of the base;
a deodorizer provided in the first section of the base and configured to release ions; and
a blower provided adjacent to the deodorizer to blow the ions through the vents to break apart pollutants in the air at least above the upper opening of the base.

15. The treadmill of claim 14, wherein the deodorizer includes a housing with an opening to expose a section of a photocatalytic deodorizer and at least one light module configured to emit light toward the exposed section of the photocatalytic deodorizer to activate a release of ions by the photocatalytic deodorizer.

16. The treadmill of claim 15, wherein the photocatalytic deodorizer is made of or coated in at least one of titanium or titanium dioxide.

17. The treadmill of claim 14, further comprising a sterilizing light provided below the vent to face the belt and separated from the deodorizer by a cover, the sterilizing light configured to emit ultraviolet radiation (UV) to the belt as the belt moves at a prescribed speed.

18. The treadmill of claim 14, further comprising a fragrance assembly provided behind the vent and adjacent to the blower, the fragrance assembly being configured to release at least one scent which is blown through the vent by the blower, wherein the deodorizer and the fragrance assembly are provided at opposite sides of the blower, and the fragrance assembly has an opening which is closed to prevent release of the scent when the deodorizer is operated.

19. The treadmill of claim 14, further comprising a thermoelectric assembly provided adjacent to the blower and configured to heat or cool air which is blown through the vent by the blower, wherein the thermoelectric assembly includes a Peltier device, at least one heat sink provided at at least one of above or below the Peltier device, and a fan provided under the Peltier device.

20. A treadmill for a pet, comprising:
a base having a plurality of vents;
first and second rollers provided below the vents and spaced apart from each other by a prescribed distance;
third and fourth rollers provided below the vents and spaced apart from each other by the prescribed distance;
a first belt wrapped around the first and second rollers to form a first closed loop, a section of the first closed loop being exposed and being adjacent to a first side of the vents;
a second belt wrapped around the third and fourth rollers to form a second closed loop, a section of the second closed loop being exposed and being adjacent to a first side of the vents;
a deodorizer provided in the base at a second side of the vents and configured to release ions; and
a blower provided adjacent to the deodorizer to blow the ions from the first side to the second side of the vents to break apart pollutants in the air at least above the sections of the first and second closed loops.

* * * * *